US012797178B2

(12) United States Patent
Opie et al.

(10) Patent No.: US 12,797,178 B2
(45) Date of Patent: Nov. 17, 2026

(54) ENDOVASCULAR DEVICE FOR SENSING AND OR STIMULATING TISSUE

(71) Applicant: The University of Melbourne, Parkville (AU)

(72) Inventors: Nicholas Lachlan Opie, Parkville (AU); Thomas James Oxley, New York, NY (US); Gil Simon Rind, Parkville (AU); Stephen Michael Ronayne, Parkville (AU); Sam Emmanuel John, Parkville (AU)

( * ) Notice: Subject to any disclaimer, the term of this patent is extended or adjusted under 35 U.S.C. 154(b) by 346 days.

(21) Appl. No.: 18/528,484

(22) Filed: Dec. 4, 2023

(65) Prior Publication Data

US 2024/0099825 A1 Mar. 28, 2024

Related U.S. Application Data

(63) Continuation of application No. 16/943,883, filed on Jul. 30, 2020, now Pat. No. 11,938,016, which is a (Continued)

(30) Foreign Application Priority Data

Oct. 20, 2015 (AU) ................................ 2015904302
Dec. 4, 2015 (AU) ................................ 2015905045

(51) Int. Cl.
*A61B 5/293* (2021.01)
*A61B 5/00* (2006.01)
(Continued)

(52) U.S. Cl.
CPC .................. *A61F 2/06* (2013.01); *A61B 5/24* (2021.01); *A61B 5/283* (2021.01); *A61B 5/291* (2021.01); *A61B 5/4052* (2013.01); *A61B 5/4064* (2013.01); *A61B 5/6862* (2013.01); *A61F 2/90* (2013.01); *A61N 1/0529* (2013.01);
(Continued)

(58) Field of Classification Search
CPC ........ A61N 1/05; A61N 1/059; A61N 1/0556; A61N 1/0534
See application file for complete search history.

(56) References Cited

U.S. PATENT DOCUMENTS 6,018,682 A 1/2000 Rise
6,171,239 B1 1/2001 Humphrey
(Continued)

FOREIGN PATENT DOCUMENTS

CN 101052343 10/2007
CN 101137977 3/2008
(Continued)

OTHER PUBLICATIONS

Oxley, T. et al. "Minimally invasive endovascular stent-electrode array for high-fidelity, chronic recordings of cortical neural activity," Nature Biotechnology, 34(3):320-327, Feb. 8, 2016.

*Primary Examiner* — Eun Hwa Kim
(74) *Attorney, Agent, or Firm* — Holland & Hart LLP

(57) ABSTRACT

Devices, methods and systems for transmitting signals through a device located in a blood vessel of an animal, for stimulating and/or sensing activity of media proximal to the device, wherein the media includes tissue and/or fluid.

17 Claims, 72 Drawing Sheets

Related U.S. Application Data continuation of application No. 15/955,412, filed on Apr. 17, 2018, now Pat. No. 10,729,530, which is a continuation-in-part of application No. PCT/US2016/057768, filed on Oct. 19, 2016.

(60) Provisional application No. 62/486,851, filed on Apr. 18, 2017, provisional application No. 62/379,625, filed on Aug. 25, 2016.

(51) Int. Cl.

| | |
|---|---|
| ***A61B 5/24*** | (2021.01) |
| ***A61B 5/283*** | (2021.01) |
| ***A61B 5/291*** | (2021.01) |
| ***A61F 2/06*** | (2013.01) |
| ***A61F 2/90*** | (2013.01) |
| ***A61N 1/05*** | (2006.01) |
| *A61B 5/0215* | (2006.01) |
| *A61F 2/88* | (2006.01) |

(52) U.S. Cl.

CPC ........... *A61B 5/0215* (2013.01); *A61B 5/4836* (2013.01); *A61B 5/7207* (2013.01); *A61B 2505/09* (2013.01); *A61F 2/88* (2013.01); *A61F 2230/0067* (2013.01); *A61F 2250/0001* (2013.01)

(56) References Cited

U.S. PATENT DOCUMENTS

| | | | |
|---|---|---|---|
| 6,442,413 | B1 | 8/2002 | Silver |
| 6,537,310 | B1 | 3/2003 | Palmaz et al. |
| 6,820,676 | B2 | 11/2004 | Palmaz et al. |
| 7,190,998 | B2 | 3/2007 | Shalev et al. |
| 7,647,097 | B2 | 1/2010 | Flaherty et al. |
| 7,751,877 | B2 | 7/2010 | Flaherty et al. |
| 7,881,780 | B2 | 2/2011 | Flaherty |
| 7,901,368 | B2 | 3/2011 | Flaherty et al. |
| 7,991,461 | B2 | 8/2011 | Flaherty et al. |
| 8,060,194 | B2 | 11/2011 | Flaherty |
| 8,095,209 | B2 | 1/2012 | Flaherty |
| 8,386,050 | B2 | 2/2013 | Donoghue et al. |
| 8,489,192 | B1 | 7/2013 | Hlavka et al. |
| 8,560,041 | B2 | 10/2013 | Flaherty et al. |
| 8,812,096 | B2 | 8/2014 | Flaherty et al. |
| 9,220,899 | B2 | 12/2015 | Cattaneo et al. |
| 9,375,330 | B2 | 6/2016 | Sims et al. |
| 9,409,012 | B2 | 8/2016 | Eidenschink et al. |
| 9,821,154 | B2 | 11/2017 | Muessig et al. |
| 10,485,968 | B2 | 11/2019 | Opie et al. |
| 10,575,783 | B2 | 3/2020 | Oxley |
| 10,729,530 | B2 | 8/2020 | Opie et al. |
| 11,141,584 | B2 | 10/2021 | Opie et al. |
| 12,396,838 | B2 | 8/2025 | Opie et al. |
| 12,397,153 | B2 | 8/2025 | Opie et al. |
| 2004/0249302 | A1 | 12/2004 | Donoghue et al. |
| 2005/0113744 | A1 | 5/2005 | Donoghue et al. |
| 2005/0137646 | A1 | 6/2005 | Wallace et al. |
| 2005/0137647 | A1 | 6/2005 | Wallace et al. |
| 2005/0143589 | A1 | 6/2005 | Donoghue et al. |
| 2005/0203366 | A1 | 9/2005 | Donoghue et al. |
| 2005/0251238 | A1 | 11/2005 | Wallace et al. |
| 2005/0251239 | A1 | 11/2005 | Wallace et al. |
| 2005/0267597 | A1 | 12/2005 | Flaherty et al. |
| 2005/0272974 | A1 | 12/2005 | Gavriel |
| 2005/0273890 | A1 | 12/2005 | Flaherty et al. |
| 2006/0049957 | A1 | 3/2006 | Surgenor et al. |
| 2006/0058627 | A1 | 3/2006 | Flaherty et al. |
| 2006/0058854 | A1 | 3/2006 | Abrams et al. |
| 2006/0089709 | A1* | 4/2006 | Helmus .................. A61F 2/915 623/1.44 |
| 2006/0167564 | A1 | 7/2006 | Flaherty et al. |
| 2006/0189901 | A1 | 8/2006 | Flaherty et al. |
| 2006/0206167 | A1 | 9/2006 | Flaherty et al. |
| 2006/0241356 | A1 | 10/2006 | Flaherty |
| 2006/0253166 | A1 | 11/2006 | Flaherty et al. |
| 2006/0259107 | A1 | 11/2006 | Caparso et al. |
| 2007/0032738 | A1 | 2/2007 | Flaherty et al. |
| 2007/0106143 | A1 | 5/2007 | Flaherty |
| 2007/0142871 | A1 | 6/2007 | Libbus et al. |
| 2007/0156126 | A1 | 7/2007 | Flaherty |
| 2007/0239256 | A1 | 10/2007 | Weber et al. |
| 2008/0009914 | A1 | 1/2008 | Buysman et al. |
| 2008/0015459 | A1 | 1/2008 | Llinas |
| 2008/0027346 | A1 | 1/2008 | Litt et al. |
| 2008/0118546 | A1 | 5/2008 | Thatcher et al. |
| 2008/0119911 | A1 | 5/2008 | Rosero |
| 2008/0183253 | A1 | 7/2008 | Bly |
| 2009/0131873 | A1 | 5/2009 | Spear et al. |
| 2009/0155336 | A1 | 6/2009 | Rezai |
| 2009/0221896 | A1 | 9/2009 | Rickert et al. |
| 2010/0023021 | A1 | 1/2010 | Flaherty |
| 2010/0063411 | A1 | 3/2010 | Donoghue et al. |
| 2010/0106259 | A1 | 4/2010 | Llinas et al. |
| 2010/0114195 | A1 | 5/2010 | Burnes et al. |
| 2010/0152812 | A1 | 6/2010 | Flaherty et al. |
| 2010/0292602 | A1 | 11/2010 | Worrell et al. |
| 2010/0305476 | A1 | 12/2010 | Thornton et al. |
| 2013/0090651 | A1 | 4/2013 | Smith |
| 2013/0096648 | A1 | 4/2013 | Benson |
| 2013/0184789 | A1 | 7/2013 | Stett et al. |
| 2013/0206454 | A1* | 8/2013 | Cattaneo .............. A61N 1/0551 174/126.1 |
| 2013/0226272 | A1* | 8/2013 | Cattaneo ............ A61N 1/36114 607/116 |
| 2013/0231658 | A1* | 9/2013 | Wang ................. A61B 18/1492 606/41 |
| 2013/0282084 | A1 | 10/2013 | Mathur et al. |
| 2014/0025069 | A1 | 1/2014 | Willard |
| 2014/0058528 | A1 | 2/2014 | Contreras-Vidal et al. |
| 2014/0142570 | A1 | 5/2014 | Bakczewitz et al. |
| 2014/0180391 | A1 | 6/2014 | Dagan et al. |
| 2014/0288667 | A1* | 9/2014 | Oxley .................. A61B 5/6862 607/45 |
| 2015/0105772 | A1* | 4/2015 | Hill .................... A61B 18/1492 606/41 |
| 2015/0230742 | A1 | 8/2015 | Silver |
| 2016/0067474 | A1* | 3/2016 | Muessig .................. A61N 1/05 607/116 |
| 2018/0236221 | A1 | 8/2018 | Opie et al. |
| 2018/0303595 | A1 | 10/2018 | Opie et al. |
| 2019/0046119 | A1 | 2/2019 | Oxley |
| 2019/0358445 | A1 | 11/2019 | Opie et al. |
| 2020/0352697 | A1 | 11/2020 | Opie et al. |
| 2021/0378595 | A1 | 12/2021 | Oxley |
| 2021/0393948 | A1 | 12/2021 | Opie et al. |
| 2024/0207034 | A1 | 6/2024 | Opie et al. |
| 2025/0281122 | A1 | 9/2025 | Oxley |
| 2025/0352785 | A1 | 11/2025 | Opie et al. |

FOREIGN PATENT DOCUMENTS

| | | |
|---|---|---|
| JP | 1998-340747 | 12/1998 |
| JP | 2007-520254 | 7/2007 |
| JP | 2007-535984 | 12/2007 |
| JP | 2008-538517 | 10/2008 |
| JP | 2009-519807 | 5/2009 |
| JP | 2009-527303 | 7/2009 |
| JP | 2009-531157 | 9/2009 |
| JP | 2010-516384 | 5/2010 |
| JP | 2010-516405 | 5/2010 |
| JP | 2013-514860 | 5/2013 |
| JP | 2013-157275 | 8/2013 |
| JP | 2016-202820 | 12/2016 |
| JP | 2019-514444 | 6/2019 |
| WO | WO 2003/101532 | 12/2003 |
| WO | WO 2005/001707 | 1/2005 |
| WO | WO 2005/046469 | 5/2005 |
| WO | WO 2005/051167 | 6/2005 |
| WO | WO 2005/051189 | 6/2005 |
| WO | WO 2005/065738 | 7/2005 |

(56) References Cited

FOREIGN PATENT DOCUMENTS

| | | |
|---|---|---|
| WO | WO 2005/092183 | 10/2005 |
| WO | WO 2005/107852 | 11/2005 |
| WO | WO 2005/110528 | 11/2005 |
| WO | WO 2006/015002 | 2/2006 |
| WO | WO 2006/020794 | 2/2006 |
| WO | WO 2006/041738 | 4/2006 |
| WO | WO 2006/073915 | 7/2006 |
| WO | WO 2006/074029 | 7/2006 |
| WO | WO 2006/076164 | 7/2006 |
| WO | WO 2006/076175 | 7/2006 |
| WO | WO 2006/078432 | 7/2006 |
| WO | WO 2006/086086 | 8/2006 |
| WO | WO 2006/105478 | 10/2006 |
| WO | WO 2007/058950 | 5/2007 |
| WO | WO 2007/078410 | 7/2007 |
| WO | WO 2007/146060 | 12/2007 |
| WO | WO 2008/019384 | 2/2008 |
| WO | WO 2008/094345 | 8/2008 |
| WO | WO 2008/094789 | 8/2008 |
| WO | WO 2009/135075 | 11/2009 |
| WO | WO 2010/078175 | 7/2010 |
| WO | WO 2013/049887 | 4/2013 |
| WO | WO 2017/070252 | 4/2017 |
| WO | WO 2018/195083 | 10/2018 |

* cited by examiner

ENDOVASCULAR DEVICE FOR SENSING AND OR STIMULATING TISSUE

CROSS-REFERENCE TO RELATED APPLICATIONS

This application is a continuation of U.S. patent application Ser. No. 16/943,883 filed Jul. 30, 2020, which is a continuation of U.S. patent application Ser. No. 15/955,412 filed Apr. 17, 2018, now U.S. Pat. No. 10,729,530, which claims the benefit of priority to U.S. Provisional Application No. 62/486,851 filed Apr. 18, 2017, which is incorporated herein by reference in its entirety for all purposes. U.S. patent application Ser. No. 15/955,412 is also a continuation-in-part of International Patent Application No. PCT/US2016/057768 filed Oct. 19, 2016, now published as WO2017/070252, which is a non-provisional application of Australian Provisional Application 2015904302 filed Oct. 20, 2015, of Australian Provisional Application 2015905045 filed Dec. 4, 2015, and of U.S. Provisional Application No. 62/379,625 filed Aug. 25, 2016, the contents of which are incorporated herein by reference in their entirety for all purposes.

TECHNICAL FIELD OF THE INVENTION

The present invention relates to a medical device for implantation into a blood vessel of an animal.

BACKGROUND OF THE INVENTION

Any discussion of document, devices, acts or knowledge in this specification is included to explain the context of the invention. It should not be taken as an admission that any of the material forms a part of the prior art base or the common general knowledge in the relevant art in Australia or elsewhere on or before the priority date of the disclosure and broad consistory statements herein.

In the United States alone, nearly two million people suffer from various neuromuscular disorders where control of limbs is severely impaired. In many of these patients, however, the portion of the brain responsible for movement remains intact, and it is disease and trauma to the spinal cord, nerves and muscles that limit mobility, function and independence. For these people, the ability to restore lost control at even a rudimentary level could lead to a greatly improved quality of life.

At present, there are two primary options for restoring function. One option is to increase the capabilities of the remaining pathways, substituting paralyzed or amputated muscles with those under voluntary control. While this method has been highly successful for amputees by re-innervating forearm nerves into abdominal muscles which control a bionic arm, the restored function greatly depends on the site of damage or condition, with people paralyzed by brainstem or high cervical injuries only able to achieve minor functional improvement. A second option is to provide the brain with a new communication and control channel to convey messages to the external world. Currently, these brain controlled interfaces (BCIs) measure electroencephalographic or other electrophysiological activity via surgically implanted epidural, subdural, and intracortical electrodes. While cortical measurements performed with electrodes placed on the scalp enable non-invasive neuronal measurements, they require daily application and are prone to noise and movement related artefacts. Penetrating and non-penetrating intracranial electrodes, implanted after a craniotomy directly onto the surface of a cortical area, have much better signal to noise ratios (relative to scalp electrodes) and have been shown to enable rudimentary prosthetic hand operation. These methods, however, require invasive surgery and carry a relatively high risk of complication, which can involve infections and bleeding. Furthermore, craniotomies are limited in access to the central nervous system, with many motor and sensory cortex areas hidden and inaccessible within cortical folds. These approaches are restricted in position and cannot be relocated once implanted and are subject to signal deterioration due to glial scar formation surrounding penetrating electrodes.

Thus, there remains a need to record and stimulate from cortical tissue in a method which is minimally invasive whilst also ensuring longevity and efficacy of recorded and induced signals.

By using blood vessels as a conduit to the brain, the risks associated with craniotomies, and the invasive creation of a burr hole in the skull of the patient is removed whilst also removing current noise and movement related artefacts observed with non-invasive scalp electrodes. Despite the minimally invasive benefits provided by these types of procedures, it is preferable that thrombus formation caused by the blockage of blood flow through a vessel is prevented. It is also preferable that the electrical energy delivered to the electrodes be as efficient as possible, which will reduce the burden placed on the electrical circuitry. Optimization of wireless telemetry aimed to send power and data directly through the body to the implanted device, will enhance device functionality and negate the risk of infection caused through lead wires creating a direct passage between the vessel and the external environment. The ability to implant coils inside blood vessels will similarly reduce surgical risks associated with perforated vasculature.

Thus, there remains a need to provide improved intravascular electrodes, telemetry circuitry and implantation positions that are capable of more efficiently transmitting and receiving electrical energy between vessels and external circuitry, while minimizing the occlusion of blood flow.

It is generally desirable to overcome or ameliorate one or more of the above mentioned difficulties, or at least provide a useful alternative.

SUMMARY OF THE INVENTION

According to the present invention, there is provided a medical device for implantation into a blood vessel of an animal, including: (a) a stent movable between a collapsed condition of use for insertion into said vessel and an expanded condition of use for resiliently bearing against a wall of said vessel; (b) one or more electrodes coupled to the stent for stimulating and/or sensing activity of media proximal to the device, wherein the media includes tissue and/or fluid. The term stent is meant to include any support structure that maintains, carries, supports or incorporates the one or more electrodes within the tissue and/or fluid. The term stent can include conventionally designed medical stents, alternatively, the term stent can include any mechanical framework or scaffolding that positions electrode elements within a body lumen, such as a vessel, and facilitates electrical coupling of the electrode element(s) to a lead or other conductive structure. In certain variations, portions of the support structure itself can function as electrodes.

According to the present invention, there is also provided a method of recording of neural information or stimulation of neurons from the superior sagittal sinus or branching cortical veins of a patient using the above described device, including the steps of: (a) implanting the device in either the superior sagittal sinus or branching cortical veins; (b) receiving activity; and (c) generating data representing said activity; and (d) transmitting said data to a control unit.

According to the present invention, there is also provided a method of for stimulation and recording neural information or stimulation of neurons from the visual cortex of a patient using the above-described device, including the steps of: (a) implanting the device in a vessel in the visual cortex of the patient; and (b) recording neural information associated with the vessel or stimulating neurons in accordance with received stimulation data.

According to the present invention, there is also provided a system for controlling use of apparatus coupled to an animal or human, including: (a) the above-described device, said device being adapted for placement within a vessel of an animal or human to stimulate and/or sense the activity of media proximal to the device; (b) a control unit adapted for communication with the device; (c) apparatus coupleable to the animal or human, said apparatus adapted for in communication with the control unit, wherein the control unit is adapted to perform the steps of: (i) receiving data from the device representing activity of media proximal to the device; (ii) generating control signals for the apparatus; and (iii) sending said control signals to said apparatus.

According to the present invention, there is also provided a control unit for controlling operation of apparatus coupled to an animal or a human, said control unit being adapted to perform the steps of: (a) receiving data from the above-described device, said data representing activity of media proximal to a vessel within which the device is placed; (b) generating control signals for controlling operation of the apparatus; and (c) sending said control signals to the apparatus.

The present disclosure further includes a medical device for use within a tubular body having a lumen, the medical device comprising: a frame structure forming a plurality of struts, where the frame structure is moveable between a reduce profile and an expanded profile in which a diameter of the frame structure increases; where at least one of the plurality of struts forming the frame structure comprises an electrically conductive material on a support material, the electrically conductive material extending along at least a portion of the strut and being covered with a non-conductive material; at least one electrode formed by an opening in the non-conductive material on the portion of the strut; and a lead located at an end of the frame structure and configured to be in electrical communication with the electrically conductive portion, the lead extending from the frame structure.

The medical device can further include a connector block configured to electrically couple the medical device to an external device, where the lead extends from the frame structure to the connector block.

In another variation, the present disclosure includes a method of recording of neural information or stimulation of neurons a patient the method comprising: receiving a signal representative of neural activity from a device positioned in a vessel of the patient; generating data representing said activity using the signal; and transmitting said data to a control unit; generating a control signal from the control unit; and transmitting the control signal to an apparatus coupled to the patient.

The present disclosure also includes a system for controlling an apparatus coupled to an animal or human. In one example, the system comprises a device adapted for placement within a vessel of the animal or human to stimulate and/or sense the activity of media proximal to the device; a control unit adapted for communication with the device, wherein the control unit is adapted to: (i) receive data from the device representing activity of media proximal to the device; (ii) generate a control signal; and (iii) transmit the control signal to said apparatus.

The system can include an apparatus selected from or more of the following: an exoskeleton; a prosthetic limb; a wheelchair; a computer; and/or an electrical or electro-mechanical device.

BRIEF DESCRIPTION OF THE DRAWINGS

Variations of the present invention are hereafter described, by way of non-limiting example only, with reference to the accompanying drawing. Like reference numerals in the drawings indicate identical or functionally similar features/elements throughout.

DETAILED DESCRIPTION

Figure 1:
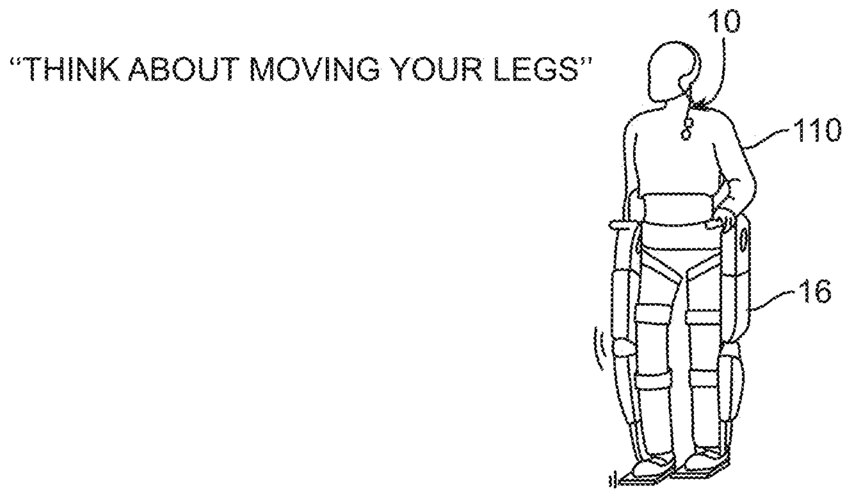
FIG. 1 is a diagrammatic illustration of a system for controlling use of apparatus coupled to an animal or a human.

The system 10 shown in FIGS. 1 to 4 includes: 1) a medical device 100 designed for placement within a vessel 103 of an animal or human 110 to stimulate and/or sense the activity of media (tissue and fluids) proximal (adjacent or touching) to the device 100, whether this be located inside or outside the vessel 103; 2) a control unit 12 (also referred to as a connector block and telemetry system) adapted for communication with the device; 3) a communication conduit 14 for facilitating communications between the device 100 and the control unit 12; and 4) apparatus 16 coupleable to the animal or human 110, the apparatus 16 adapted for communication with the control unit.

The control unit 12 can be adapted to perform the steps of: (a) receiving data from the device 100 representing activity of media proximal to the device 100; (b) generating control signals for the apparatus 16; and (c) sending the control signals to the apparatus 16. In some variations, the system includes connector block (illustrated by element 12) that functions as connector and acts as an extension of the communication conduit. In variations of the system, the control unit/connector block: is hermetically sealed and insulates the leads from the device to the control unit; can be inserted using zero-contact force attachments or attachments that do not require excessive force to insert (i.e., using balseal spring contacts); has a portion of the lead that is made from a stiffer silicone or similar material for handling and insertion into the connector. Variations of the device can include markers to identify portions of the leads that are stiffer (and can be handled) to distinguish from leads that cannot be handled. Such markers can include line-style markers, different colours or other indicators to clearly identify the regions. Variations of the connector block can have a fitting (e.g., clasp) such that multiple connectors can be inserted (i.e., two contact connectors (with 8 contacts each) for a 16 electrode Stentrode lead). The fitting can ensure securing of the contacts, alignment and prevention of water ingress When the medical device 100 is inserted adjacent to the motor cortex in the manner shown in FIGS. 2A, 2B, and 3, the system 10 can be used, for example, to control operation of an exoskeleton, and/or an artificial limb in the manner shown in FIG. 1.

This device 100 is implanted into blood vessels 103, from which, it will utilise electrodes mounted on a self-expanding member 101 to record or stimulate neighbouring tissue. Information is to be passed from or to the electrodes through the communication conduit 14, inside of the blood vessel 103, to a telemetry system 12 that, in turn, passes information (using wires or wirelessly) to or from an external apparatus 16, which includes (but is not limited to) one or more of the following:

(a) an exoskeleton; (b) wheelchair; (c) computer; and/or (d) other electrical or electro-mechanical device.

As such, in one specific application, the implanted medical device 100 has the capability to enable a paralysed patient 110 to use their thoughts directly to command and control a gait aid such as an exoskeleton or robotic legs 16.

Other applications for the implantable medical device 100 include (but are not limited to): (a) detection and prevention of seizures; (b) detection and prevention of involuntary muscular or neural control (for example to alleviate symptoms associated with: (i) multiple sclerosis; (ii) muscular dystrophy; (iii) cerebral palsy; (iv) paralysis and (v) Parkinsons'; (c) detection and therapeutic alleviation of neurological conditions, such as: (i) post-traumatic stress disorder; (ii) obsessive compulsive disorder; (iii) depression; and (iv) obesity; (d) direct brain control of computers and equipment, such as: (i) vehicles; (ii) wheelchairs; (iii) gait aids; robotic limbs; (e) direct input for sensory stimulation for: (i) blindness (connection to a camera); (ii) deafness (connection to microphone); (iiii) proprioception (connection to touch-sensitive robotic and computer systems); (f) internal assessment of personal health and wellbeing: (i) heart rate; (ii) respiration rate; (iii) temperature; (iv) environmental conditions; (v) blood sugar levels; and (vi) other biochemical and neurological markers; (g) internal communication (telepathy) between implanted groups of people utilising the device for information transmission, auditory, visual and proprioceptive feedback (for example, real time communication of what the implantee sees or hears); and (h) augmentation and optimisation of musculskeletal control and dexterity (for performance enhancement or rehabilitation).

Figure 2A:
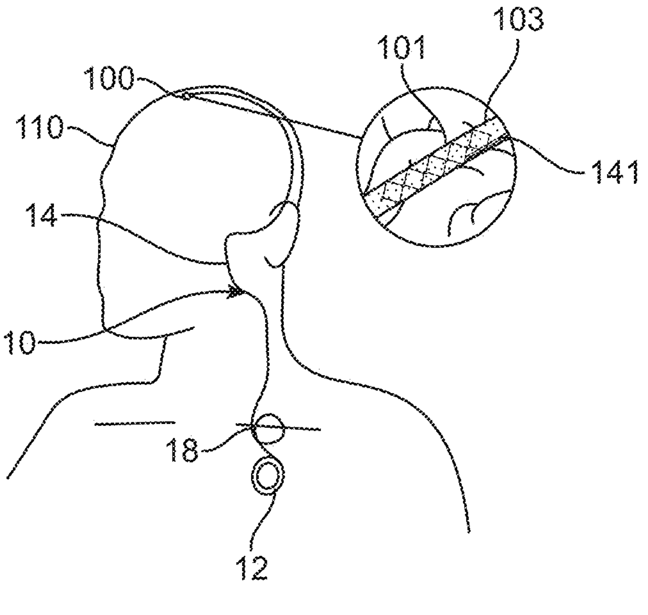
FIG. 2A is a diagrammatic illustration showing parts of the system shown in FIG. 1.
Figure 2B:
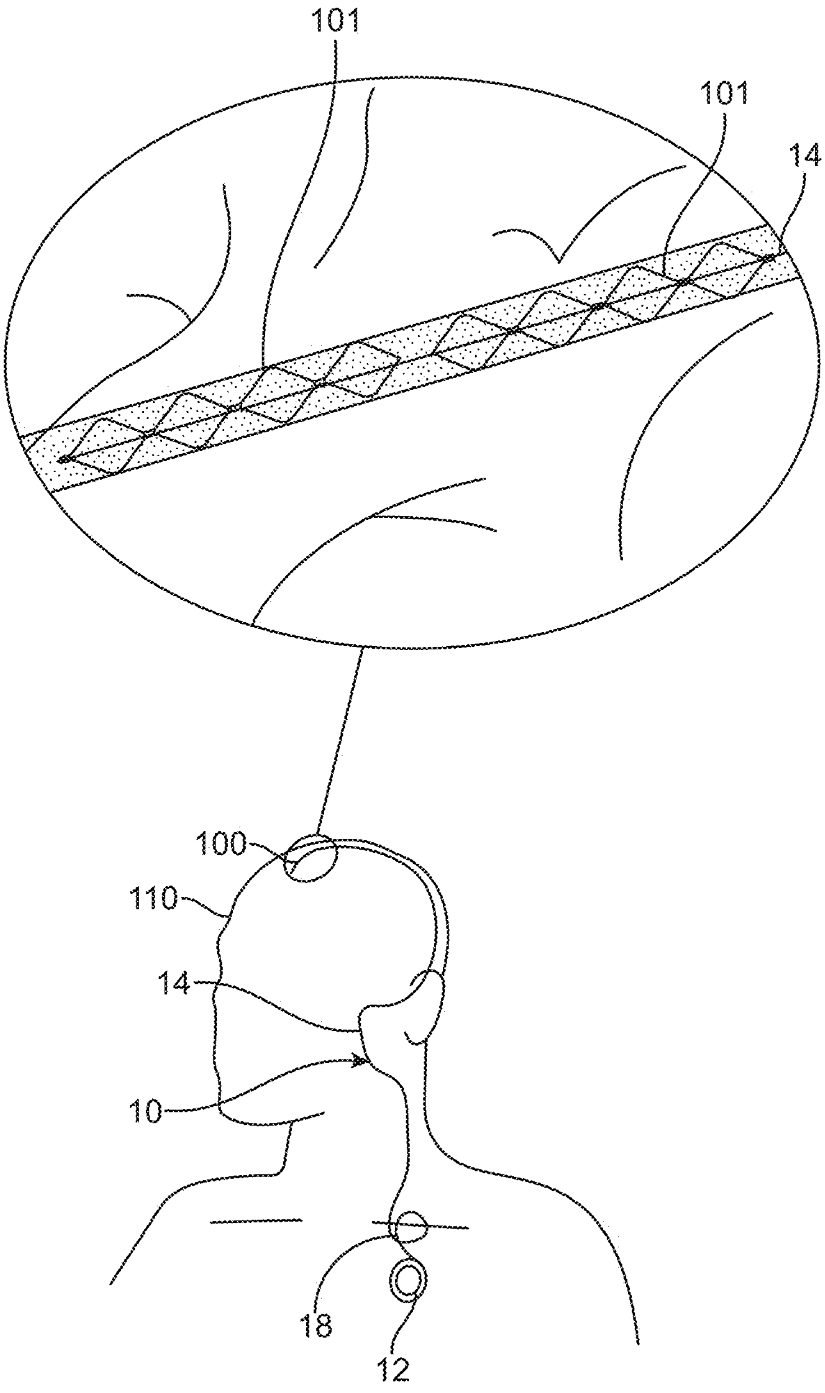
FIG. 2B is a diagrammatic illustration showing of an additional variation of the system comprising two or more stents.
Figure 3:
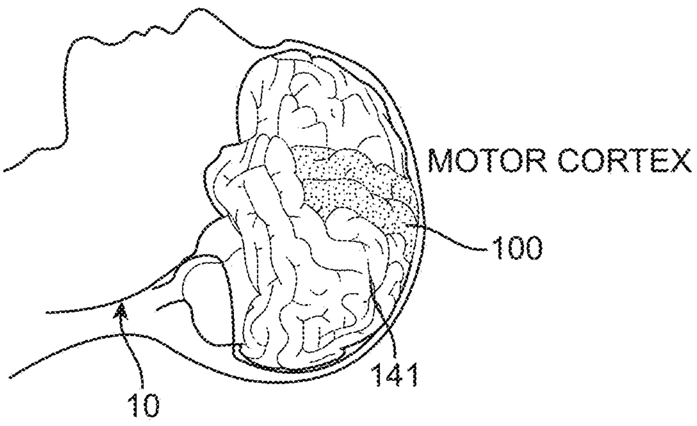
FIG. 3 a diagrammatic illustration showing parts of the system shown in FIG. 1.
Figure 4:
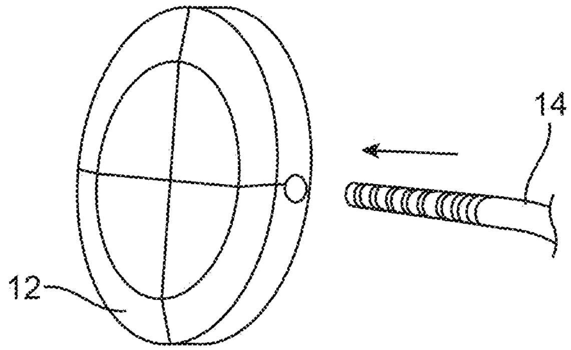
FIG. 4 is a diagrammatic illustration of a control unit of the system shown in FIG. 1.

FIG. 2B illustrates a two-stent 101 system. For purposes of illustration, the stents are positioned in a single vessel. However, the stents can be configured such that they can be positioned in separate vessels. The stents 101 can be joined by non-conductive material to form a power receiver and transmitting antenna. Alternatively, the stents can be coupled by one or more wires or conductive elements. Moreover, the system can include active electronics between the stents 101.

The devices described herein can be positioned in any number of areas of brain structures depending upon the desired outcome. For example, as discussed in Teplitzky, Benjamin A., et al. "Computational modeling of an endovascular approach to deep brain stimulation." *Journal of Neural Engineering* 11.2 (2014): 026011.stents can be positioned as follows: Internal capsule for depression and obsessive compulsive disorder (OCD); thalamus for epilepsy (E), Parkinsons' Disease, essential tremor, Tourette syndrome, consciousness disorder, chronic pain, obsessive compulsive behavior; fornix for Alzheimer's disease; globus pallidus internus for dystonia, depression, Tourette syndrome; hippocampus for epilepsy; hypothalamus for obesity, anorexia mentosa; inferior thalamic pduncle for depression and obsessive compulsive disorder; lateral habenula for depression, obesity, anorexia mentosa; nucleus accumbens for depression, obsessive compulsive disorder, addiction, obesity, anorexia mentosa; periaqueductal /periventricular for chronic pain; subgenal cingulate white matter for depression; subthalamic nucleus for Parkinson's Disease, dystonia, depression, obsessive compulsive disorder, epilepsy; and ventral capsule for obsessive compulsive disorder.

1. Medical Device

As shown in FIGS. 5*a*, 5*b*, 5*d* and 6, the medical device 100 generally includes: a. a collapsible and expandable stent 101; b. a plurality of electrodes 131 coupled to the stent 101; c. electrode lead wires 141 electrically coupled to electrodes 131; d. an olive 112 coupled to the stent 101 by an olive wire 114 for preventing perforation of vessels during implantation; e. implanted chips; f. contacts 151 couple to the lead wires 141 to enable communication between the device 100 to the control unit 12; and g. a stent shaft 121 is used to deploy the device 100.

Electrode lead wires 141 can be electrically connected to at least one electrode and will be wound around the stent strut lattice 108 such that mechanical compression and extension is not interfered with. Electrode wires 141 may be wound around the stent shaft 121, thread through a stylet shaft or may form part of the stent shaft directly. Lead wires 141 will form connections with electrode contacts 151 on the opposite end of the stent shaft to the stent, whereby electrical contact a connector block mechanism 12 enables the connection path with external equipment 16, which included but is not limited to computers, wheelchairs, exoskeletons, robotic prosthesis, cameras, vehicles and other electrical stimulation, diagnostic and measurement hardware and software.

The term electrode 131 is used in this specification to refer to any electrical conductor used to make contact with media in and/or around a blood vessel 103.

A detailed description of the operation of each of these components is set out below.

The Stent

The stent 101 includes a plurality of struts 108 coupled together with strut crosslinks 109.

Figure 7A:
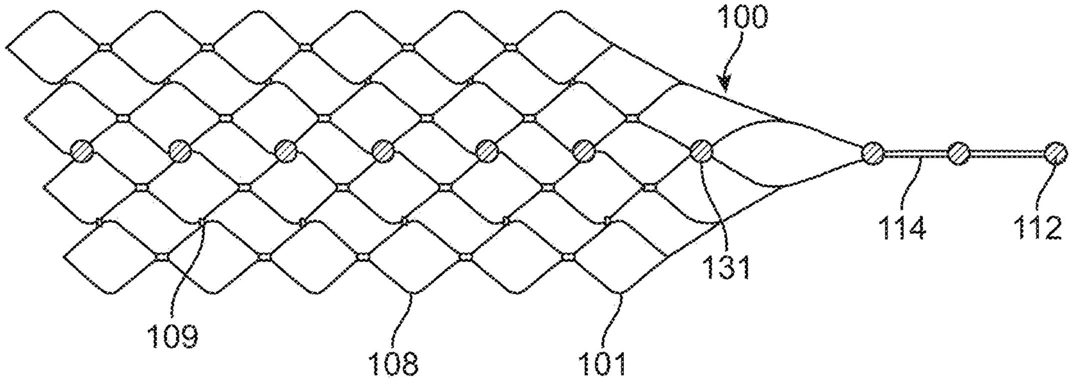
FIGS. 7A to 7E are diagrammatic illustrations of medical device of the system shown in FIG. 1.

In the arrangement shown in FIG. 7*a*, the device 100 includes nine electrodes coupled to the stent 101 in a linear pattern. As shown, the stent 101 appears flat. The top of the stent 101 may be directly joined to the bottom of the stent 101 or will curve around to meet (without permanent attachment) the bottom of the stent 101.

Figure 7B:
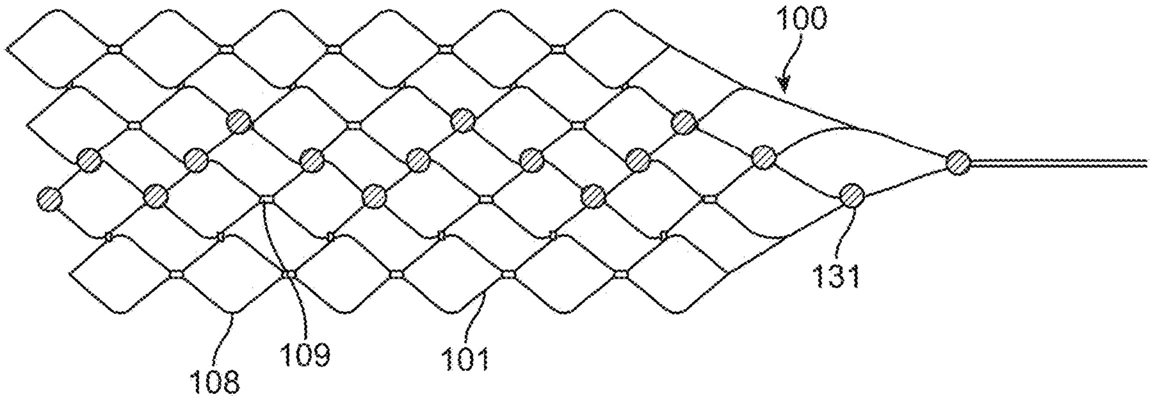
Figure 7C:
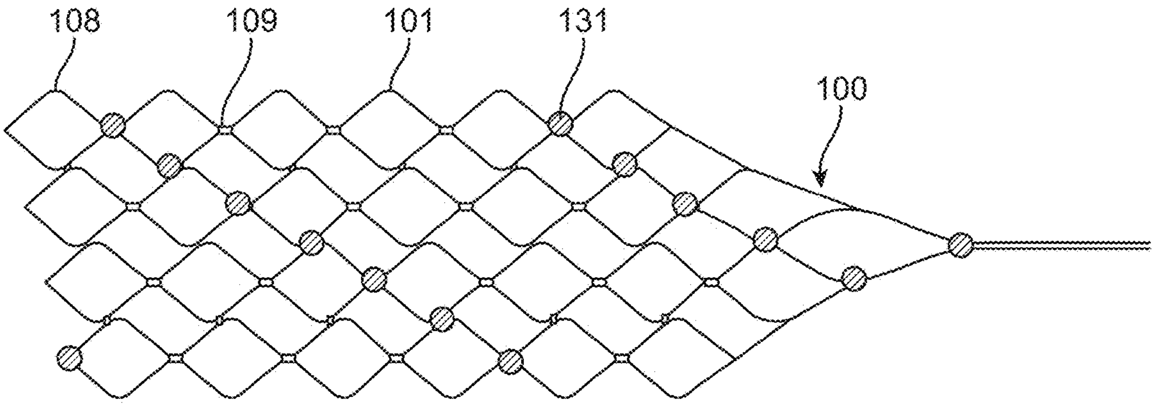
Figure 7D:
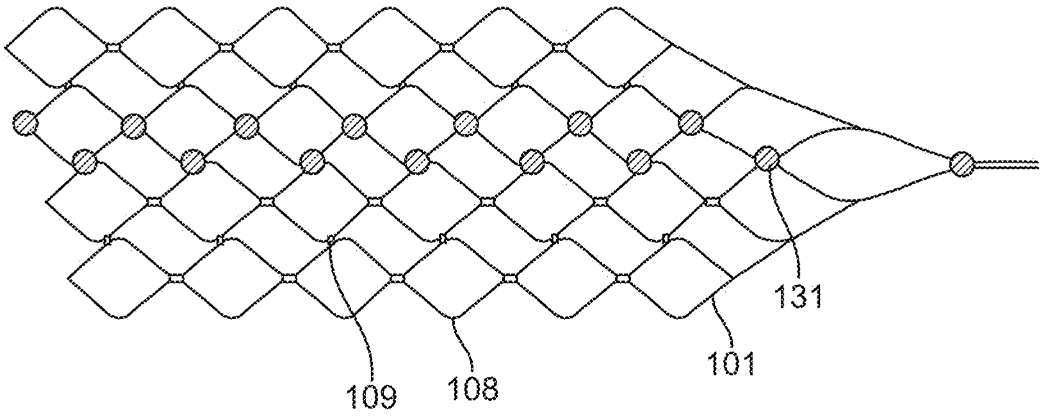
Figure 7E:
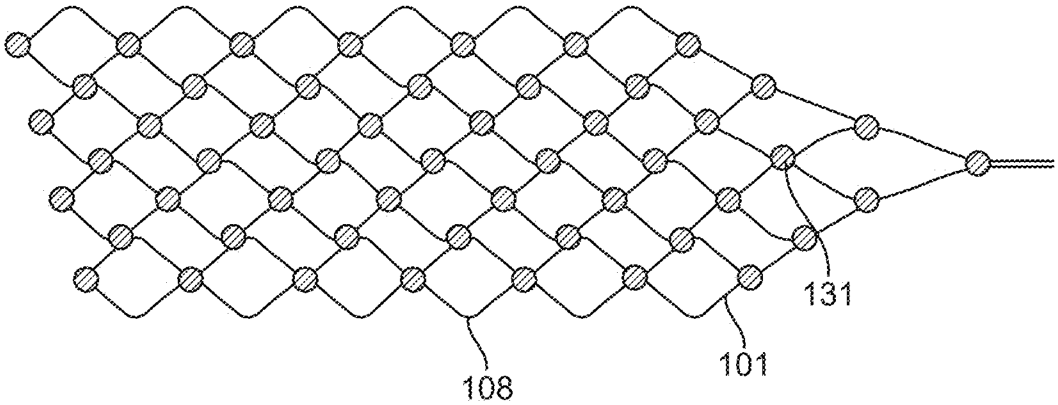
Figure 8A:
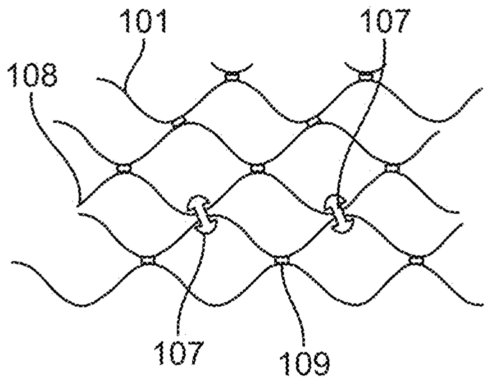
FIG. 8A is a diagrammatic illustration showing electrode mounting platforms of a medical device of the system shown in FIG. 1.
Figure 8B:
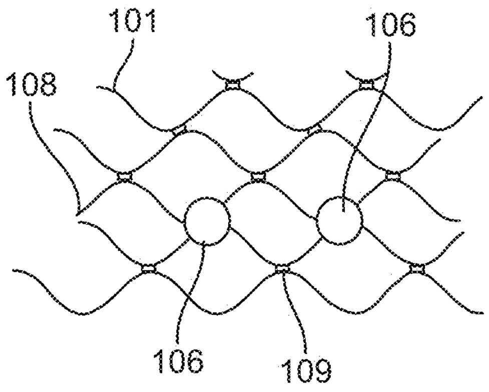
FIG. 8B is a diagrammatic illustration showing placements of a medical device of the system shown in FIG. 1.

Alternatively, the device 100 includes a stent with any suitable number of electrodes 131 arranged in any suitable configuration. For example, the electrodes can be configured as follows: the sinusoidal arrangement of electrodes 131 shown in FIG. 7*b*; the spiral arrangement of electrodes 131 shown in FIG. 7*c* to enable 360 degree contact of an electrode to the vessel wall once deployed; the reduced amplitude sinusoidal arrangement of electrodes 131 shown in FIG. 7*d* for increased coverage whilst still ensuring only one stent is at each vertical segment; and the dense arrangement of electrodes shown in FIG. 7*e* for increased coverage. The stent 101 is laser cut or woven in a manner such that there is additional material or markers where the electrodes 131 are to be placed to assist with attachment of electrodes and uniformity of electrode locations. For example, if a stent 101 was fabricated by laser cutting material away from a cylindrical tube (original form of stent), and, for example, electrodes are to be located at 5 mm intervals on the one axis, then electrode mounting platforms 107, 108 can be created by not cutting these areas from the tube. Similarly, if the stent is made by wire wrapping, then additional material 107, 108 can be welded or attached to the stent wires providing a platform on which to attach the electrodes. Alternatively, stents can be manufactured using thin-film technology, whereby material (Nitinol and or platinum and or other materials or combinations of) is deposited in specific locations to grow or build a stent structure and/or electrode array Electrodes As particularly shown in FIGS. 8*a*, the device 100 includes electrode placements 107 coupled to strut cross-links 109. The placements 107 are used to coupled the electrodes 131 to the stent. An alternative embodiment of the placements 106 is shown in FIG. 8*b*. In this embodiment, the placements are circular.

As shown, the electrodes 131 are located on or at the stent crosslinks 109. Locating the electrodes in these positions allows for changes in shape of the stent 101 (i.e expanding and collapsing) without significantly affecting the integrity of the electrodes. Alternatively, may also be located in between the stent strut crosslinks (not depicted).

Figure 9:
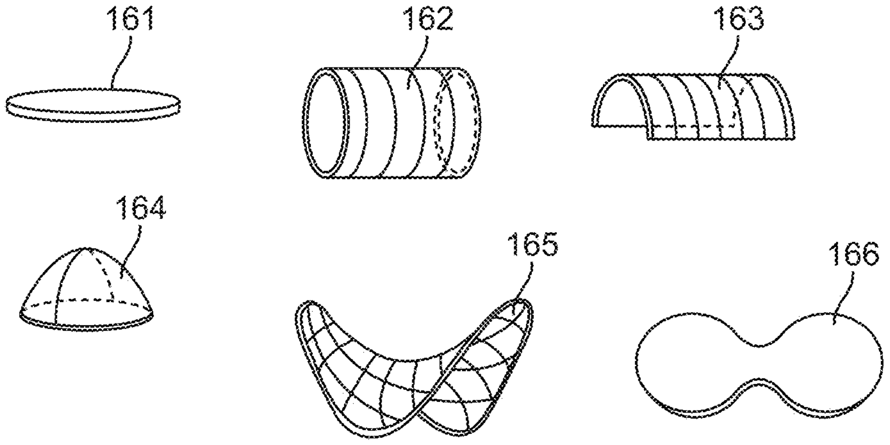
FIG. 9 shows diagrammatic illustrations of different electrode configurations.

FIG. 9 depicts different electrode geometries which include but are not limited to: flat discs 161; cylinders or rings 162; half-cylinders or rings 163; spheres, domes or hemispheres 164; hyperbolic parabaloids 165; and double electrodes or electrodes whereby they are longer along one axis 166.

Figure 10:
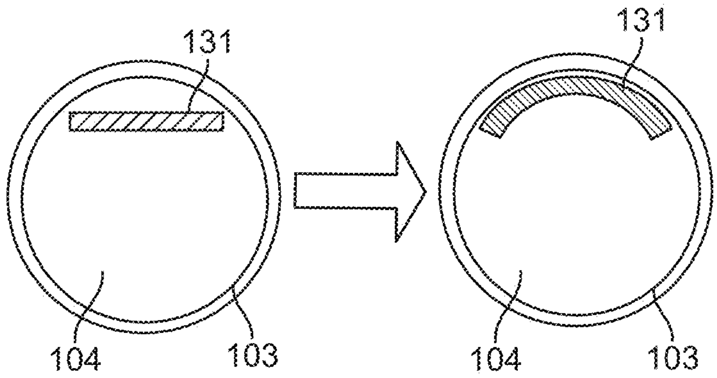
FIG. 10 shows diagrammatic illustrations of different electrode configurations.

As shown in FIG. 10, the electrodes 131 can include shape memory material and hence the electrodes 131 may be uninsulated sections of the device 100. As shown, the electrode 131 inside a patient and the vessel 104 is unobstructed. After activation of shape memory, the electrode 131 conforms to better fit the vessel wall 103.

To enhance contact and functionality of the device 100, electrodes 131 include the attachment of additional material (shape memory alloy or other conducting material) through soldering, welding, chemical deposition and other attachment methods to the stent 101 including but not limited to: directly on or between the stent struts 108; to lead wires 14 passing from the electrodes 131 to wireless telemetry links or circuitry; and directly to an olive 112 placed on the distal aspect of the device 100 to or stent shafts.

To further enhance the device 100 performance, there may be one or more electrodes 131 per wire strand 141 and there may be one or more strands 141 utilised per device 100. These strands 141 may be grouped to form a bundle 144, which may be woven in alternate sinusoidal paths around the stent struts 108 in the manner shown in FIG. 11. Similarly, there may be one or more wires 141 designated to each electrode 131 and hence there may be one or more electrodes 131 per device 100. Thus, multiple electrodes 131 may be used simultaneously.

To optimise the ability of the electrodes 131 to stimulate or record from medium (including but not limited to neural tissue, vascular tissue, blood, bone, muscle, cerebrospinal fluid), the electrodes 131 may be positioned at pre-determined intervals based on the diameter of the target vessel 103 to allow each of the electrodes 131 to be in contact with the vessel 103 in the same orientation (ie, all electrodes facing to and in contact with the left vessel wall upon deposition). Electrodes 131 may be mounted such that recordings or stimulation can be directed to all 360 degrees of the vessel simultaneously Similarly, to enhance the recording and stimulation parameters of the electrodes 131, the electrode sizes may be varied, with larger electrodes 131 used to assess greater areas of neighbouring medium with smaller electrodes 131 utilised for localisation specificity.

Alternatively, the electrodes 131 are made from electrically conductive material and attached to one or more stents, which form the device 100 and allow for multiple positions. In this embodiment, the electrodes 131 are made from common electrically active materials such as platinum, platinum-iridium, nickel-cobalt alloys, or gold, and may be attached by soldering, welding, chemical deposition and other attachment methods to one or more lead wires 141, which may be directly attached to the shape memory shaft(s). The electrodes 131 can be one or more exposed sections on the insulated lead wire 141 and the electrode lead wires may be wrapped around one or more shape memory backbones. There may be one or more electrodes and lead wires wrapped around a single shape memory backbone, and, where multiple shape memory backbones are used in the one device, the backbones may have different initial insertion and secondary deposition positions. Thus, they may be used for targeting multiple vessels simultaneously.

Figure 12:
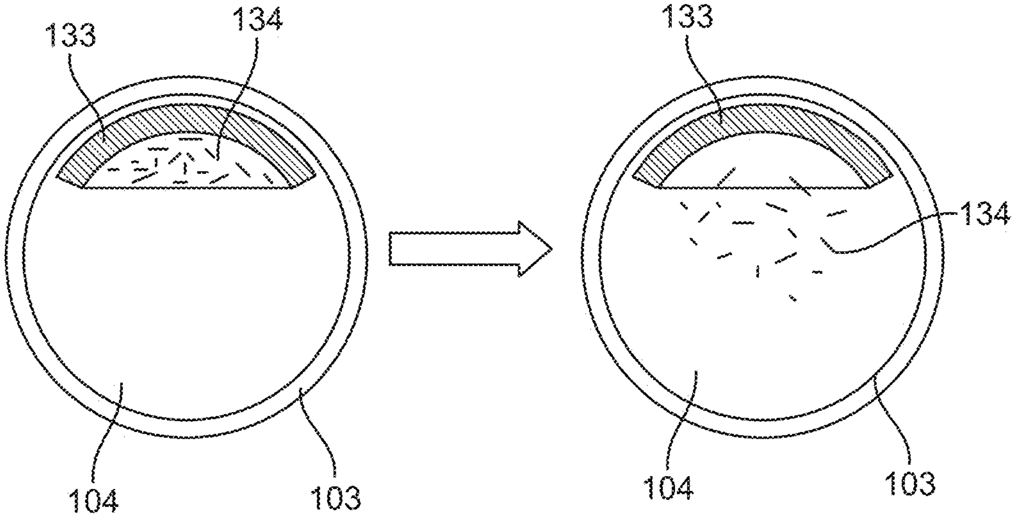
FIG. 12 shows diagrammatic illustrations of different electrode configurations.

As shown in FIG. 12, the electrodes 131 can be designed such that they are carriers of substances 134 and solutions such as therapeutic drugs, including but not limited to anti-thrombogenic, and materials. In this embodiment, the electrodes 131 are designed to release the drugs, either passively through diffusion or through control by an implanted electrical clock or manually through electrical stimulation of the electrodes 131. In this embodiment, the electrodes 131 are made from materials that have portions of the electrodes 131 that are not electrically conductive.

The drug 134 can be released into the vessel 104 upon timed, natural, electrical or otherwise activation, or into the vessel wall 103.

Electrode Wires

Figure 13A:
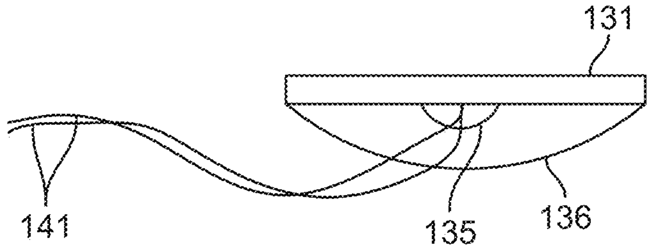
FIG. 13*a* is a diagrammatic illustration showing wire attachments to an electrode.

The electrode wires 141 are electrically coupled to respective electrodes in the manner shown in FIG. 13*a*. As shown, the electrical attachment 135 and the back face of the electrode is covered in a non-conductive substance 136.

The lead wires 141 can be wrapped around the stent 101 and along a shaft 121.

Figure 5A:
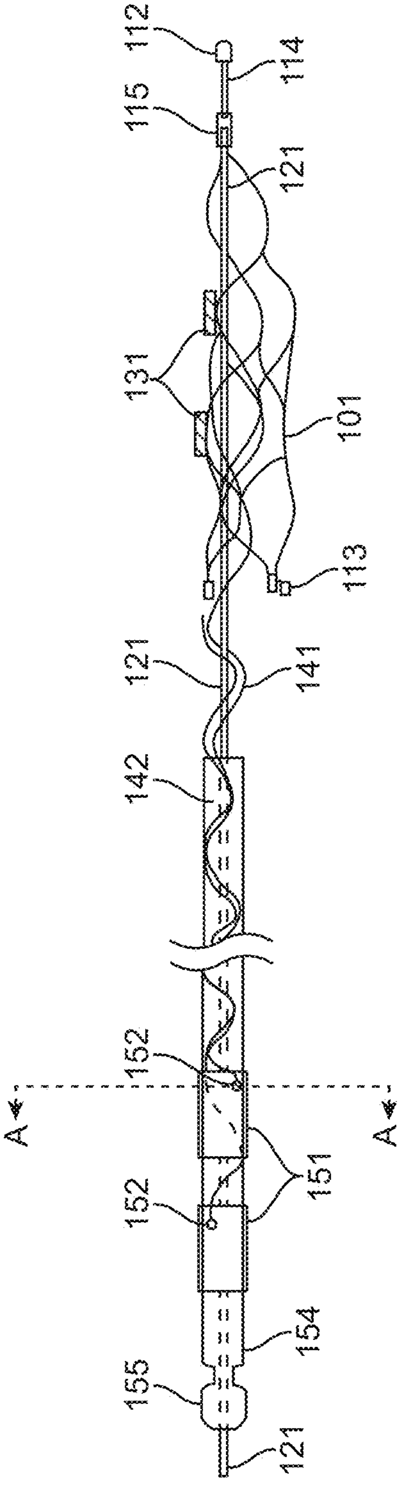
FIG. 5A is a diagrammatic illustration of a medical device of the system shown in FIG. 1.
Figure 5B:
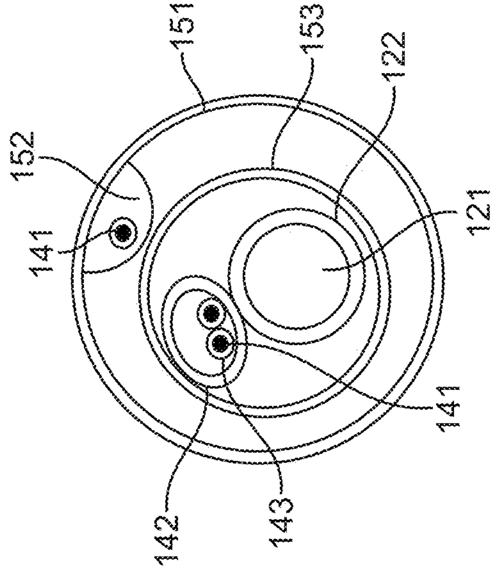
FIG. 5B is a cross-section view through the line A-A of the device shown in FIG. 5*a*.
Figure 13B:
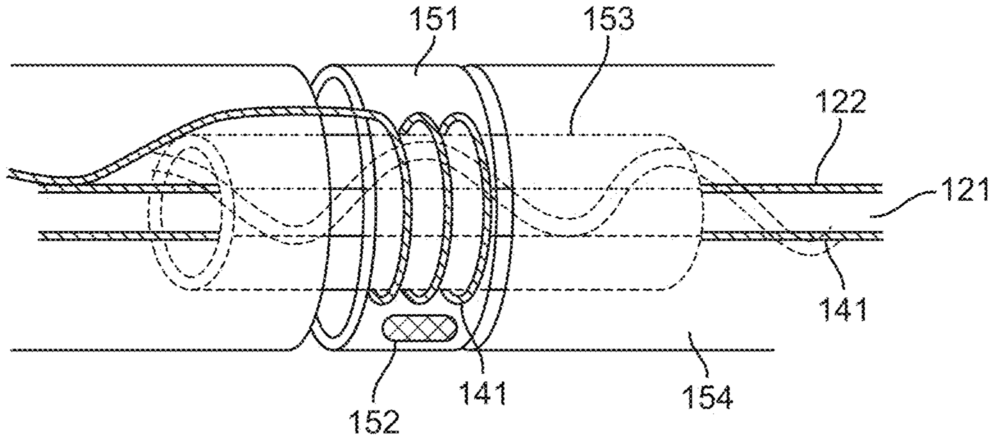
FIG. 13*b* is a diagrammatic illustration showing electrode lead wires wrapped around a shaft and covered in insulation forming a wire bundle or cable.

As shown in FIGS. 5*a*, 5*b* and 13*b*, the electrode lead wires 141 are wrapped around the shaft 121 and covered in insulation 122 forming a wire bundle or cable. A sleeve 153 wraps around the wire bundle at the location of the contact 151, whereby at least one wire 141 is wrapped around the sleeve 153 and connected to the contact 151 at a connection weld point 152. The over-molding 154 ensures a uniform diameter is present between contacts.

The sleeve 153 covers the wire bundle 142 with an exposed section of wire 141 attached 152 to a contact 151.

Distal electrodes and/or markers and/or buffers are also depicted 112 attached via a wire 114 to the stent 101. The shaft 121 is attached at the end of the stent at the attachment/detachment zone 115 and is shown passing through the sleeve 142 and electrode contacts 151 to exit behind past the connector securement point 155.

The lead wires 141 shown to be inside the sleeve 142 where they are wrapped around the shaft 121 where they make electrical contact at a contact weld 152 to the electrode contacts 151. An overcoat 154 is shown to ensure uniform diameter of the device between the contacts. The shaft 121 may be detached at the detachment zone 115 and removed following deployment in a vessel.

As shown in FIG. 13*b*, lead wires 141 are connected to electrode contacts 151. Electrode lead wires 141 are initially wrapped around a shaft 121 covered in insulation 122 forming a wire bundle or cable. A sleeve 153 is placed around the wire bundle at the location of the contact, whereby at least one wire 141 is wrapped around the sleeve and connected to the contact 151 at a connection weld point 152. Over-molding 154 may be used to ensure a uniform diameter is present between contacts.

As particularly shown in FIG. 5*b*, the stent shaft 121 is coated in an insulative layer 122, has a plurality of wires 141 that are insulated 143 and grouped in an insulated bundle 142 wrapped around it. A sleeve 153 covers the wire bundle 142 with an exposed section of wire 141 attached 152 to a contact 141.

The wires 141 are made from electrically conductive materials including but not limited to Platinum, Platinum/Tungsten, Stainless Steel, Nitinol, Platinum/Iridium, Nickel-Cobalt Alloys, or other conductive and biocompatible materials.

The wires 141 are between 10 um and 100 um thick (diameter), stranded cable or monofilament, and connect the electrodes 131 to the contacts 151. Alternatively, the wires 141 connect the electrode 131 to wireless circuitry retained on the stent or shaft.

Figure 11:
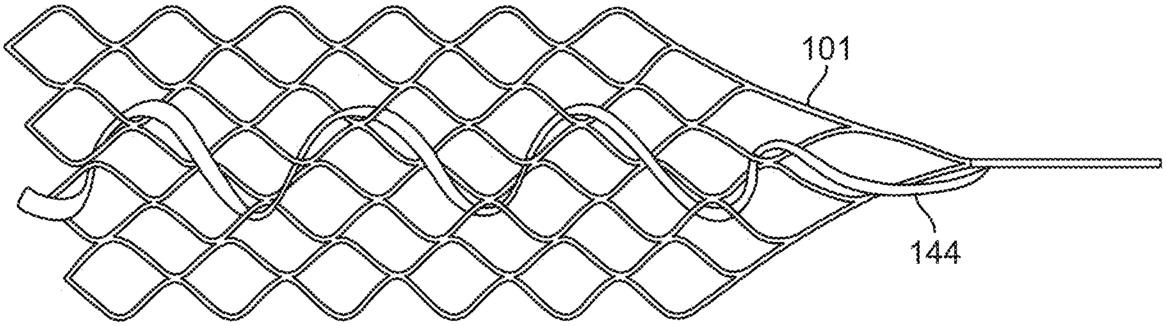
FIG. 11 is a diagrammatic illustration of a medical device of the system shown in FIG. 1.

The wires 141 are insulated with non-conductive material (ie, Teflon or polyimide). The wires 141 are wrapped around the stent struts in a sinusoidal pattern as shown in FIG. 11. Alternatively, the wires 141 are wrapped in a helical tube or wire bundle or cable, with the wire or bundle between 300 um and 2 mm in diameter (thickness)

The wires 141 are connected to contacts 151 using wire wrapping, conductive epoxy, welding, or other electrically conductive adhesion or connection means.

Olive

In the embodiment shown in FIG. 5*a*, the device 100 includes an olive 112 mounted at the distal tip to reduce risk of perforation and to improve device 100 safety during the implantation and deposition phase. In this arrangement, the olive 112 is directly connected to the front of the device 100 and act as a buffer, which is the first aspect of the device that comes in contact with the deployment catheter or the vessel during deployment. The olive 112 can additionally be used as a radiopaque distal marker. The olive 112 can be configured and attached to the stent 101 in many different forms including, but not limited to, the following:

i. Flexible Cord

As shown in FIG. 5*a*, the olive 112 is placed at a distance from the front of the stent 101, connecting with the stent 101 via a flexible cord 114.

ii. Spring Olive

Figure 14:
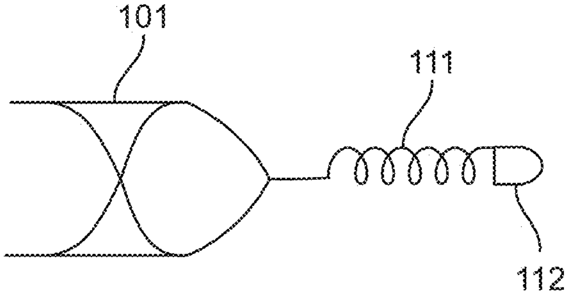
FIGS. 14 to 20 are diagrammatic illustrations showing different embodiments of the stent.

FIG. 14 depicts an olive placed on the distal end of a stent 101 whereby the olive is comprised of a buffer which may or may not be electrically active and function as an electrode 112 connected to the stent 101 by a flexible spring or helically wound wire 111.

iii. Multiple Olives

Figure 15:
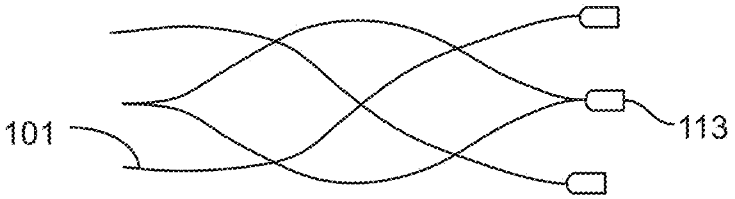

FIG. 15 depicts a plurality of olives placed on the distal end of a stent 101 whereby the olive is comprised of a plurality of buffers which may or may not be electrically active and function as an electrode 113.

iv. Short Olive

Figure 16:
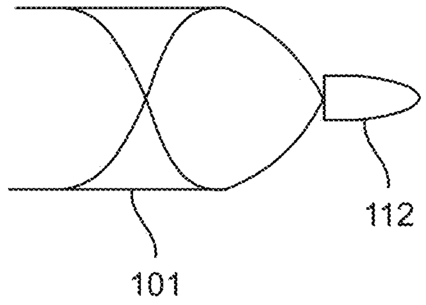

FIG. 16 depicts an olive placed on the distal end of a stent 101 whereby the olive is connected directly to the end of the stent which may or may not be electrically active and function as an electrode 112.

v. Shaped Wire Olive

Figure 17:
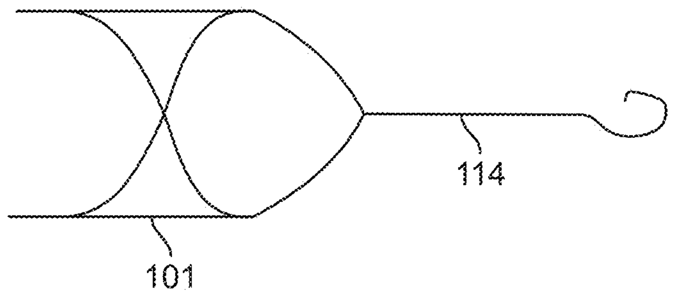

FIG. 17 depicts an olive placed on the distal end of a stent 101 whereby the olive is a flexible wire which may or may not be electrically active and function as an electrode and may or may not be shaped as a shepherds crook 114.

vi. Wire Olive

Figure 18:
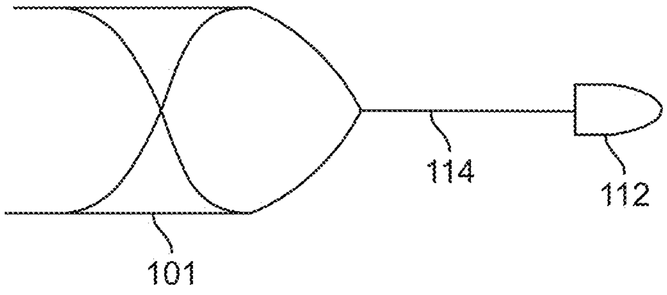

FIG. 18 depicts an olive placed on the distal end of a stent 101 whereby the olive is comprised of a buffer which may or may not be electrically active and function as an electrode 112 connected to the stent 101 by a flexible wire 114.

vii. Olive with Detachment Zone

Figure 19:
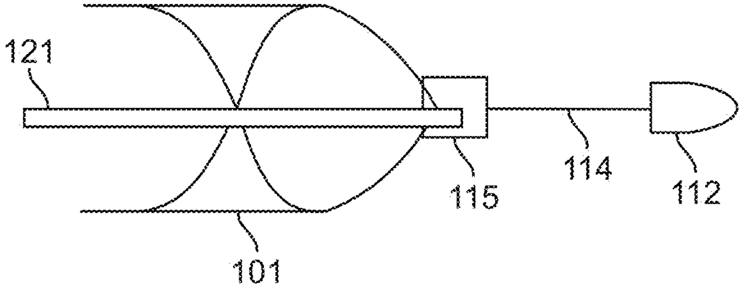

FIG. 19 depicts an olive placed on the distal end of a stent 101 whereby the olive is comprised of a buffer which may or may not be electrically active and function as an electrode 112 connected to the stent 101 by a flexible wire 114. This figure further depicts a shaft 121 that is connected to the stent 101 via an attachment and/or detachment zone 115.

Figure 20:
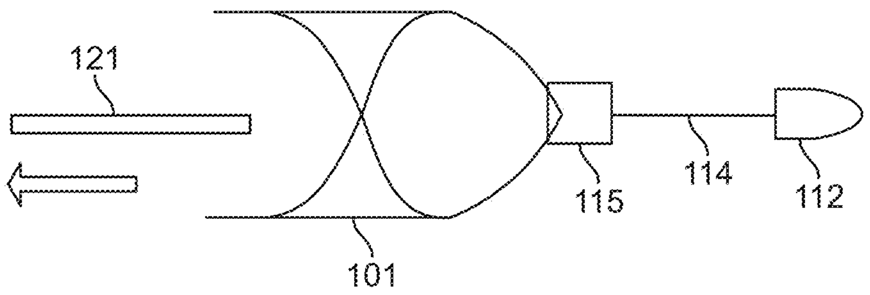

FIG. 20 further depicts the shaft 121 that is detached from the stent 101 via the attachment and/or detachment zone 115.

The flexible wire 114 includes but is not limited to electrically conductive and electrically insulating wires, springs, helical leads and tubes which may have a buffer at the front. Alternatively, the buffer is electrically conductive and acts as an electrode, comprising all the features of stent-mounted electrodes.

Implanted Chips

Implanted electrical circuitry (chips) can be used to control the stimulation and measurement of the electrodes 131. The chip can be implanted in place of an electrode (or elsewhere mounted on the stent), where the chip has the capacity to transmit the signals. The chip includes circuitry for: (a) signal amplification; (b) signal multiplexing; and (c) transmission of power and data.

The electrodes 131 are attached to one or more electrical chips (whereby the chip is defined as the electrical circuitry as well as the substrate which the chip is built on). Miniaturised chips are mounted on the stent 101 in a similar manner and position to the electrodes 131.

Alternatively, these chips may be attached at a distance from the neural recording or stimulation site such as the neck or pectoral region, or the chip may connect directly to external hardware, such as current sources, recording equipment or prostheses.

The chips can include circuitry for stimulation of neural tissue (current and/or voltage sources, batteries and/or capacitors or charge/energy storing components and switch matrices, etc) and circuitry for the recording of neural activity (amplifiers, power sources, switch matrices, etc) and blood composition (such as pH meters, salts and saline composition, glucose etc).

Further, chips may have circuitry required for the transmission of power and data through telemetry coils and self-monitoring hardware such as thermal sensors.

Figure 5C:
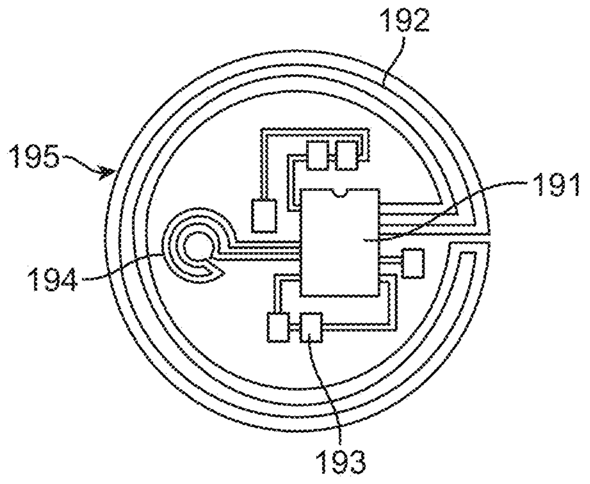
FIG. 5C is a schematic diagram of a wireless chip.
Figure 5D:
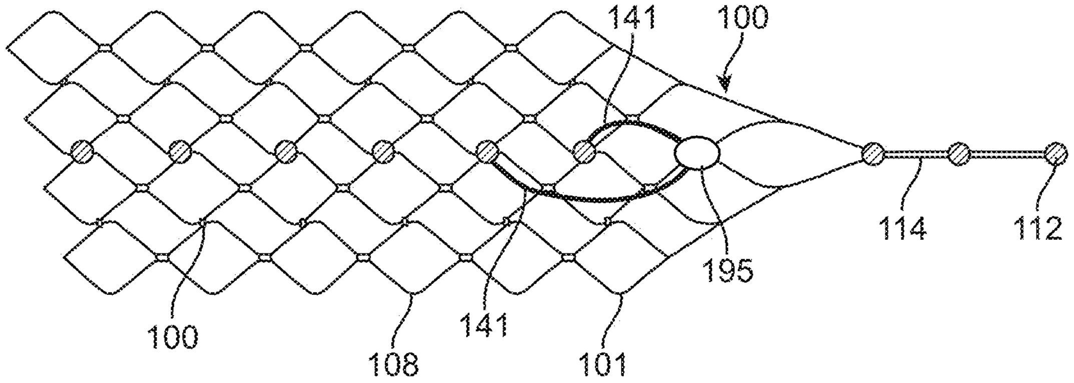
FIG. 5D is a diagrammatic illustration of a medical device of the system shown in FIG. 1.

The depiction of the wireless chip 195 shown in FIG. 5*c*, whereby the microprocessor 191 is shown as well as other components 193 (eg, capacitors, multiplexors, clocks, wireless transmitters, receivers etc). This depiction has two coils that can be used for transmission and receiving of both power and data, shown as a large coil 192 and a small coil 194.

The chip itself may contain a telemetry coil for the transmitting and receiving power and data and may contain a magnet to enable alignment with adjacent chips and telemetry coils or may be attached to shape memory alloys or other materials in which the telemetry coils are comprised.

The chip can be flexible, and may be pre-curved to the diameter of the vessel to allow for the deposition of the chip within a vessel. Thus, the chip may contain shape memory alloys or polymers to conform the chip to the curvature of the vessel during the deposition phase. The chip may also be mounted on a bioabsorbable or biodegradable substrate to allow for integration within a vessel. Multiple chips may be used simultaneously.

f. Contacts

As particularly shown in FIGS. 5*a* and 5*b*, electrode contacts 151 are required to enable connection of the device 100 to external equipment in the situation where wireless circuitry is not employed. The electrode contacts 151 can be made from materials similar to those used by the electrodes and will be of similar diameters. The contacts 151 are electrically insulated from each other and will be connected to the electrode lead wires 141 by (but not limited to) conductive epoxy, laser or resistance welding, soldering, crimping and/or wire wrapping.

The contacts 151 are platinum rings or rings of other conductive, biocompatible materials. The contacts can be made from or contain magnetic materials (ie, Neodinium).

The contacts 151 can be: (a) between 500 um and 2 mm in diameter; (b) between 500 um and 5 mm in length; and (c) between 10 um and 100 um in thickness.

The contacts 151 are shaped as discs, tubes, parabaloids or other shapes similar to those used for the electrodes 131.

The contacts are placed over non-conducting sleeve (including but not limited to a silicone tube, heat shrink, polymer coating) to assist with electrical insulation of other lead wires and electrode and stent wire, and to assist in retaining shape tubular shape whilst allowing some flexibility.

The contacts 151 can have a contact to contact separation of between 100 um and 10 mm, for example, between 1.0 mm and 3.0 mm (e.g., 2 mm or 2.46 mm) Other contact separation dimensions, more or less, as well as other ranges, narrower or wider, are also appreciated.

The contacts 151 are formed through wire wrapping of the wires 141.

At least one contact 151 can be a dummy connector (including but not limited to a metal ring, magnetic ring, plastic tube). A dummy connector in this instance is a connector that is not in electrical contact with an electrode, instead, the purpose is to enable a connection or securing point (ie, through a screw terminal) to the device in a desired location and such that the contacts (connected to electrodes) are not damaged.

The contacts 151 are separated by a non-conductive sleeve (including but not limited to a silicone tube, heat shrink, polymer coating) to reduce electrical noise and prevent contact between superficial lead wires 141.

g. Shaft

Figure 21A:
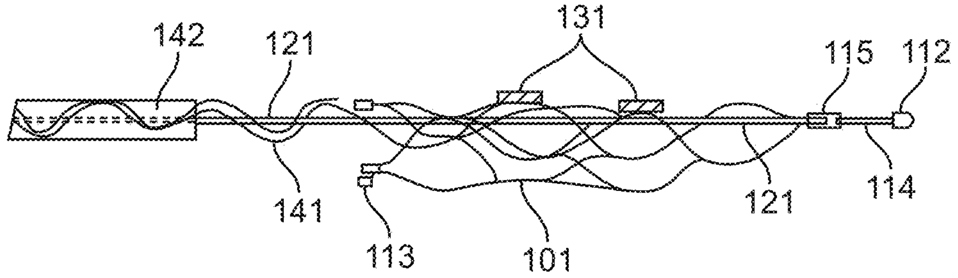
FIGS. 21*a* to 21*c* are diagrammatic illustrations showing deployment of different embodiments of the device.

As shown in FIG. 21*a*, to enable deployment, a flexible shaft 121 is connected to the device 100. In the example shown in FIG. 21*a*, the shaft 121 is connected at the distal end of the device 100 such that it acts to pull the device 100 from the front.

Figure 21B:
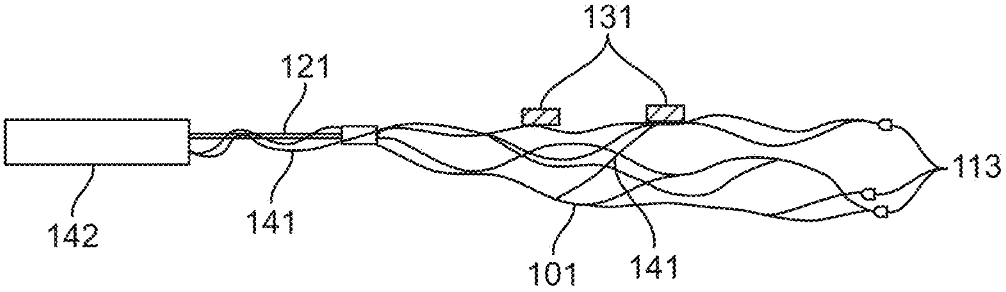

In the alternate embodiment shown in FIG. 21*b*, the shaft 121 is attached to the proximal end of the device 100 such that the shaft 121 pushes the device 100 from the back of the stent 101. In this embodiment, medical device 100 includes a plurality of electrodes 131 mounted to a stent 101 with electrode lead wires 141 wrapped around the stent 101 and the shaft 121 and covered in a sleeve 142. Distal electrodes and/or markers and/or buffers are also depicted 113 as is the stent detachment zone 105.

Figure 21C:
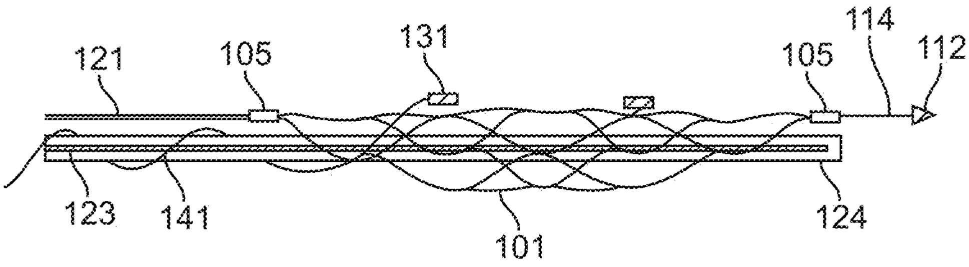

The further embodiment shown in FIG. 21*c* includes a double tapered stent 101 with mounted electrodes 131 and a stent shaft 121 attached to the stent 101 at the stent attachment/detachment zone 105. Another attachment/detachment zone 115 at the front of the stent 101 connects the stent 101 to the olive wire 114 and a stylet sleeve 124, through which, a removable stylet 123 is placed. Electrode wires 141 are shown as wrapped around the outside of the stylet sleeve 123 or as being fed through the centre.

There may be a plurality of wires, with both pushing and pulling abilities. The stent shafts 121 may be implanted permanently or may be designed to be detached and removed. In this embodiment, the attachment/detachment zone will be located at the junction of the stent shaft 121 and the stent 101. Detachment methods include, but are not limited to, electrochemical detachment, mechanical detachment and thermo-electrical detachment.

The stent shaft 121 can be used as a backbone for electrode lead wires 141, assisting the stability of the electrode lead wires 141 as they traverse from the electrodes 131 to the electrode contacts. In this embodiment, the electrode wires 141 are in a polymer 142, (including but not limited to shrink wrap, heat shrink, parylene, silicone, Teflon, etc) to provide additional mechanical support, assist in water retention and to enable coatings to be deposited onto the stent shaft where wires are present.

The stent shaft 121 may be a stylet that is removed following implantation and deposition of the device 100. In this embodiment, the stent shaft 121 may be a cylindrical tube such that the stylet 123 can be fed through the centre of the tube 121.

The wires 141 can be thread through the middle of a stylet sleeve.

The wires 141 can be wrapped around the stent shaft or stylet sleeve.

In a further embodiment, the electrode wires 141 that connect the electrodes 131 to the contacts 152 are wrapped in a wire bundle 144 and wrapped around an internal lumen tubing 145 in a helical form such that there is an internal lumen 147 whereby a removable stylet 148 can be thread during insertion and removed following deployment. This embodiment enabled removability of the stylet 148 and flexibility of the wire bundle 144 that is over coated in an external tubing 146.

Figure 21D:
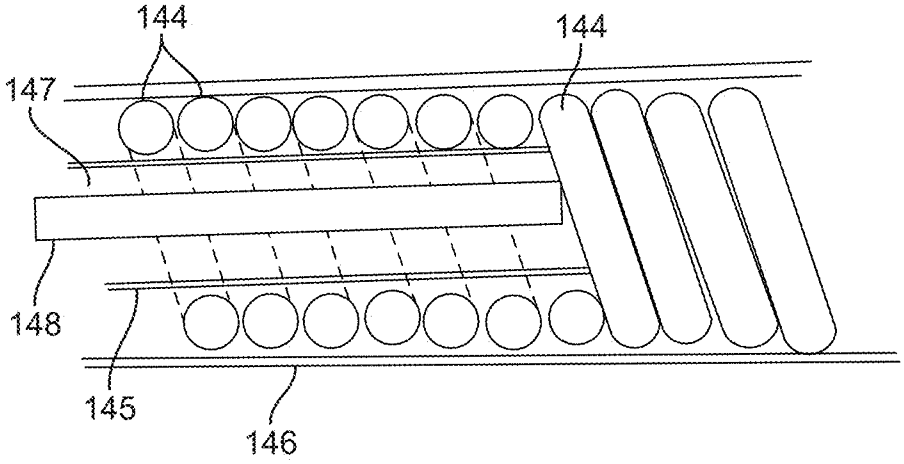
FIGS. 21*d* and 21*e* show additional information regarding a helical lead 114.
Figure 21E:
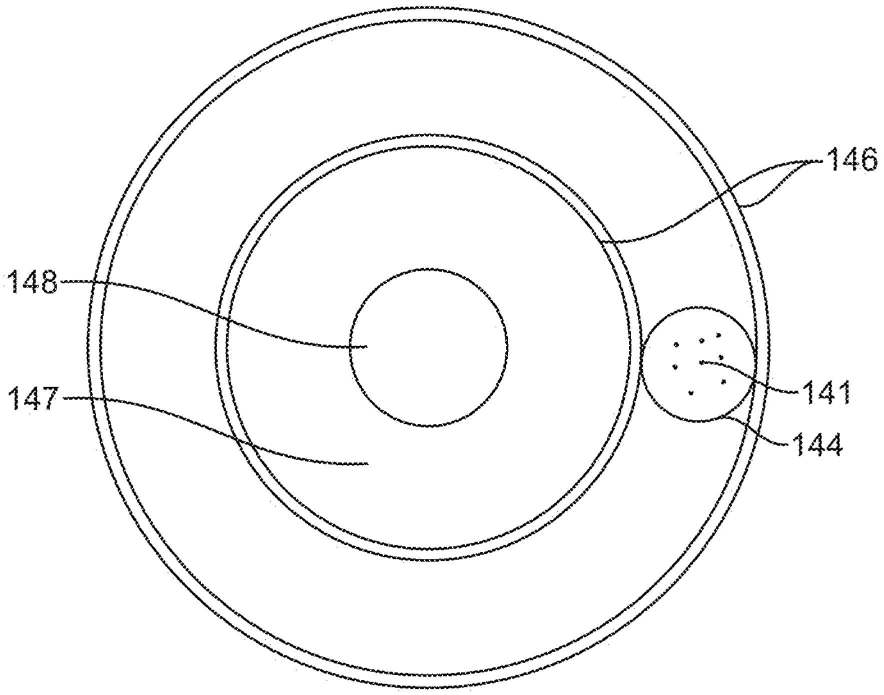

FIGS. 21*d* and 21*e* show additional information regarding a helical lead 114. As depicted, the helical 114 lead includes wire bundle 144 wrapped around an internal lumen tube 145. Through the internal lumen 147, a removable stylet 148 can be thread during delivery and removed following device placement Control Unit The control unit 12 shown in FIG. 2 is a wireless controller, relaying information and power through the skin wirelessly.

Figure 22:
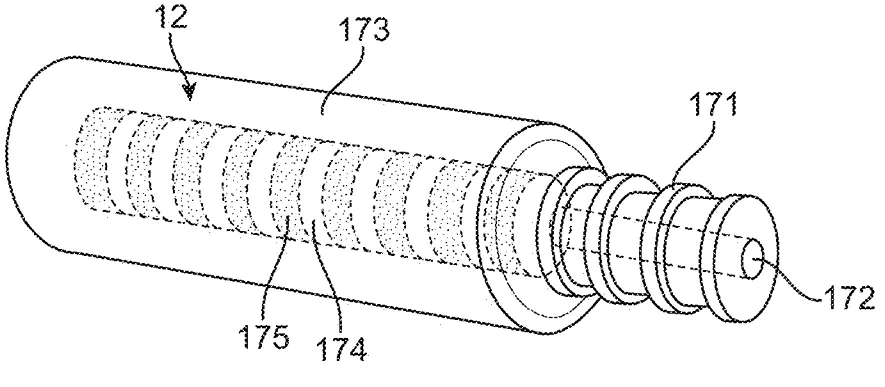
FIGS. 22 to 24 are diagrammatic illustrations of a control unit of the system shown in FIG. 1.
Figure 23:
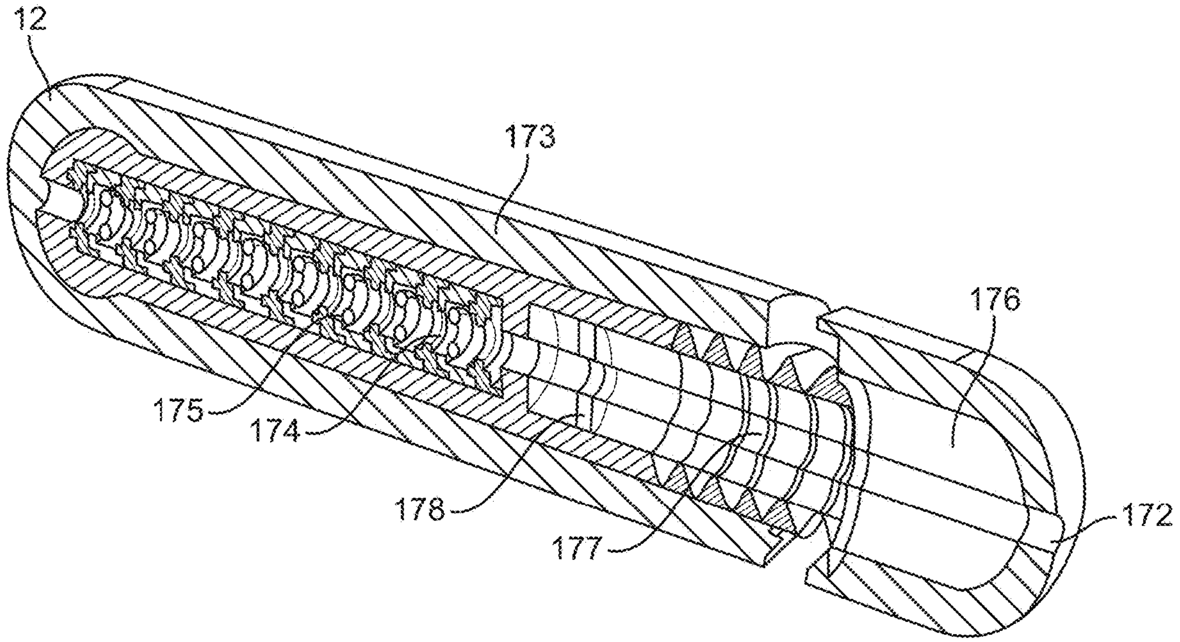
Figure 24:
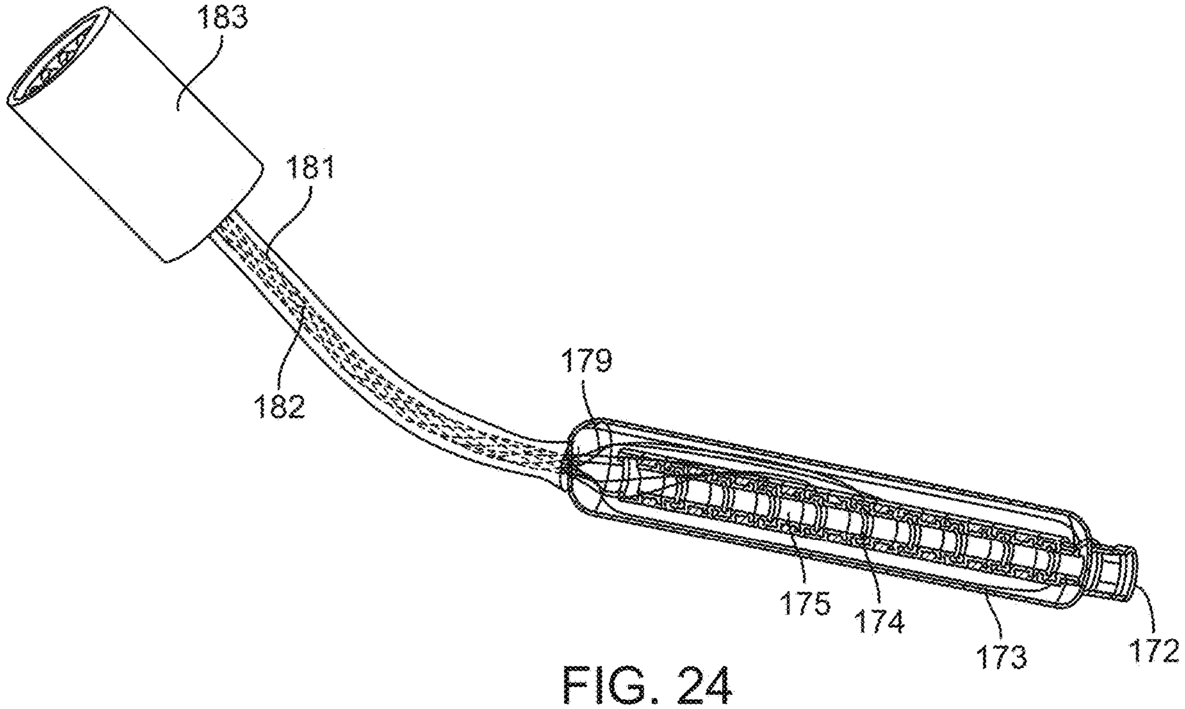

The connector block 12 in FIGS. 22, 23, and 24 are passive devices (ie, no circuitry). Essentially, it functions as an intermediate connection between the device 100 and external equipment. The device 100 is inserted into the connector block 12 whereby the device 100 contacts make electrical contact with internal contacts contained within the connector block 12. These internal contacts of the connector block 12 then form a thicker wire bundle which passes through the skin (the rest of the connector block is implanted) and can be connected to external equipment.

Essentially, as we are limited in space (the entire device must pass through a catheter as the catheter needs to be removed over the device after implantation) the connector block enables attachment of larger items to the thin device 100.

The embodiments shown in FIGS. 22, 23 and 24 are the same, although only FIG. 24 shows the wire that goes through the skin.

The control unit 12 shown in FIG. 22 is shaped to receive and make electrical connection with the lead 14. The control unit include contacts rings mounted on the inside. Here, the connector block 12 is secured and ensured water-tight through attachment of silicone and/or sutures at the grooved end.

The wireless system that is implanted on the stent directly is essentially the same (although a miniaturised version) of the wireless system 12 in FIG. 2.

As shown in FIG. 23, the electrode lead 14 is inserted and a silicone gasket is used to make a watertight seal following FIG. 24 depicts a connector block whereby the electrode lead 14 is thread through the connection opening 172 whereby the contacts connect with the electrically conductive connectors 175 inside the connector block body 173. Separation and electrical insulation and water-tightness is increased through silicone (or otherwise) separators 174. Contacts 175 are welded (or otherwise) to connector block wires 179 that may form a silicone or otherwise 181 encased bundle 181 to terminate at a wireless or direct electrical connection port 183.

Method of Using the System

Figure 25:
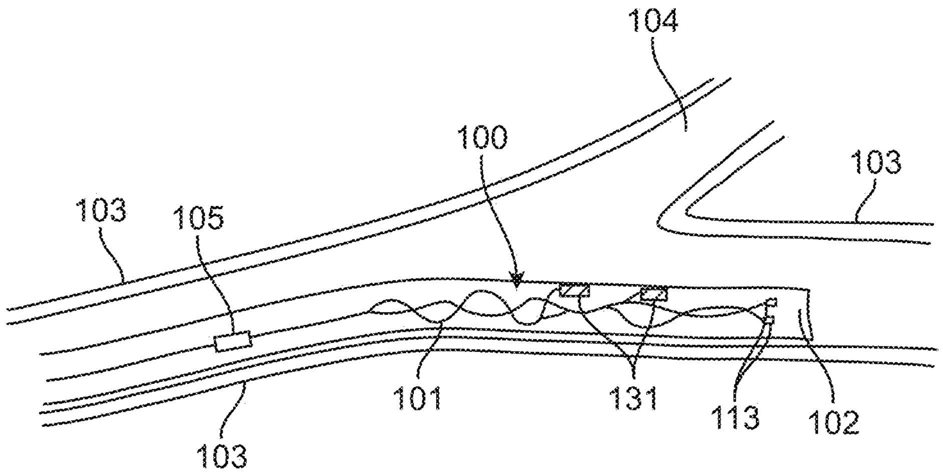
FIGS. 25 and 26 are diagrammatic illustrations showing different stages of deployment of the device.
Figure 26:
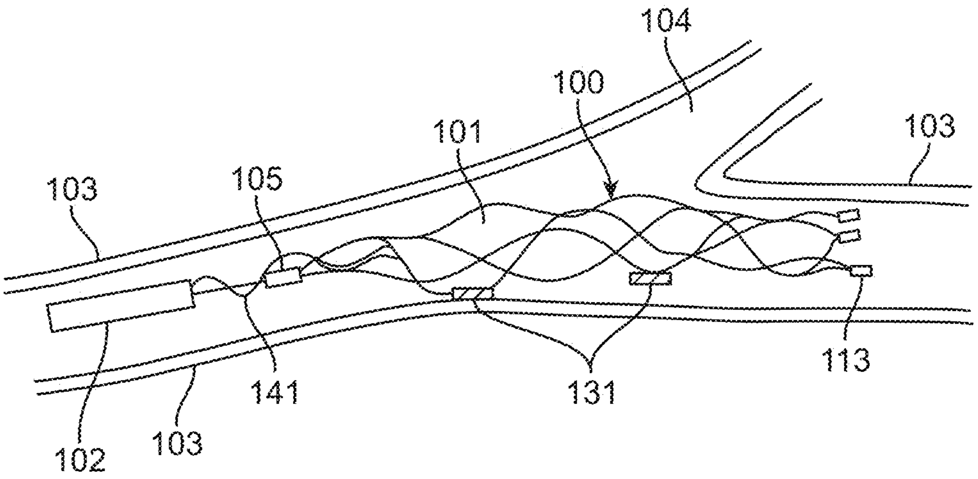

The device 100 is movable between an insertion position shown in FIG. 25 and the deposition or scaffolding position shown in FIG. 26.

In the insertion position, the device 100 is contracted and thus thin enough to be threaded through the vasculature pathway from within a catheter from an entry point (ie, the jugular vein) to a deposition point (eg, the motor cortex).

When arranged in the deposition or scaffolding position, the device 100 is in an expanded condition where scaffold electrodes mounted on the outside of the stent 101 as pressed against the vessel wall. This expanded position anchors the device 100 in its location within the vessel 103. Further, this deposition position is designed such that it has a minimal effect on blood flow integrity through the vessel 103 in which the device 100 is deposited. The scaffolding position may be synonymous to a spring, coil or helical strand, whereby the device 100 is in contact with the vessel wall only, reducing the effect on blood flow. Electrodes 131 may also be mounted on the inside of the stent 101 such that information from fluid flowing through the expanded stent 101 can be measured. For a stent 101 to be removed or relocated, additional shafts (other than that used for initial deployment) are required. These are explained in the context of this invention, with both single tapered and double tapered designs used.

To enable the device 100 to be arranged in multiple positions, the material used is such that multiple states are possible. These materials include, but are not limited to, Nitinol and other shape memory alloys and polymers. Further, to enhance the long term biocompatibility of the device 100, the polymers may be bioabsorbable or biodegradable, with a time of degradation similar to the time in which fibrosis occurs over the device 100. Hence, the electrodes 131 (which preferably are not designed to degrade, and may be made from Nitinol, shape memory alloys, conductive polymers, other non-shape memory alloys and inert and biocompatible metals such as platinum, iridium, stainless steel and gold) will be all that remains of the initial device 100 and will become embed inside the blood vessel 103, further enhancing the stability of the device 100 at the location of deposition Device in Blood Vessel (After Deployment)

Figure 6:
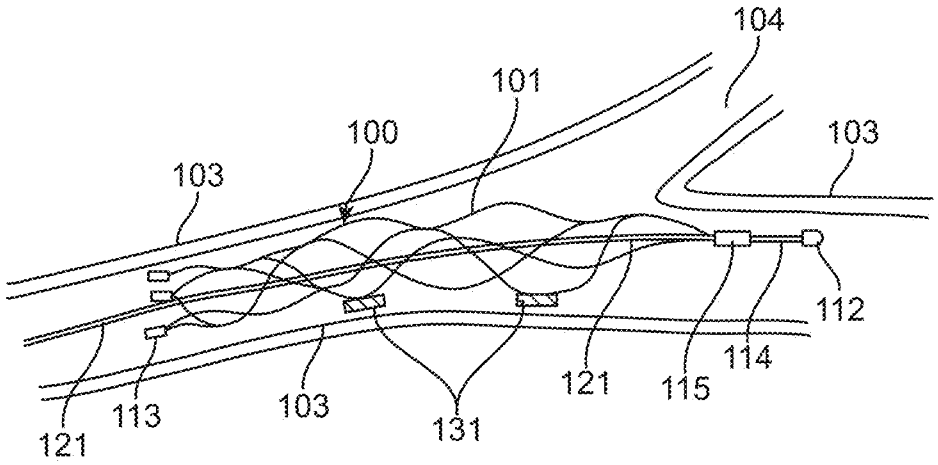
FIG. 6 is a diagrammatic illustration of a medical device located in a vessel.

FIG. 6 depicts a medical device 100 in the expanded or deposition or scaffolding position. The device 100 includes a stent 101, distal olives and/or proximity markers 112, a wire 114 attaching the stent 101 to the olive 112, a plurality of electrodes 131, and an attachment/detachment zone 115 whereby the shaft is connected to the stent 101 having been deployed in a blood vessel 104. Stent 101 mounted electrodes 131 are in direct apposition with the vessel wall 131 and are depicted as not interruptive of blood flow to any vessel (both the vessel the device is deployed in and other connected vessels). Here, the olive 112 can be used to direct the medical device into the desired vessel 104.

Device in Blood Vessel Pre-Deployment

FIG. 25 depicts a medical device 100 during implantation (surgical deployment phase) as it is being thread through vessels 104 inside a catheter 102. The stent 101, electrodes 131, stent detachment zone 105 and stent distal markers/electrodes/buffers 113 are shown, as are the vessel walls 103. Here, the catheter 102 is being used to select and direct the device into the desired vessel 104.

Device In Blood Vessel After Deployment

FIG. 26 depicts a medical device 100 in the expanded or deposition or scaffolding position comprising a stent 101, distal olives and/or proximity markers 113, a plurality of electrodes 131, lead wires 141 and a stent detachment zone 105 being deployed in a blood vessel 104 through a deposition catheter 102. Stent 101 mounted electrodes 131 are in direct apposition with the vessel wall 103 and are depicted as not interruptive of blood flow to any vessel (both the vessel the device is deployed in and other connected vessels).

Ground Electrode

Figure 27:
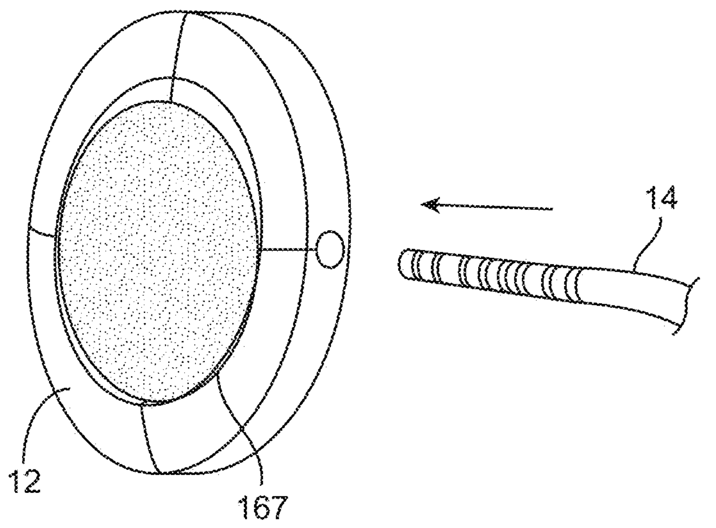
FIGS. 27 and 28 are diagrammatic illustrations of control units having ground electrodes attached thereto.

The system can include a ground electrode 167, configured in the manner shown in FIG. 27, which is used to assist and improve the quality of the recorded signals or to provide an electrical return path for stimulation applications. Here the ground electrode may be placed on the connector block provided it is implanted. Ground electrode 167 can be directly attached to the outside of the wireless controller 12.

Figure 28:
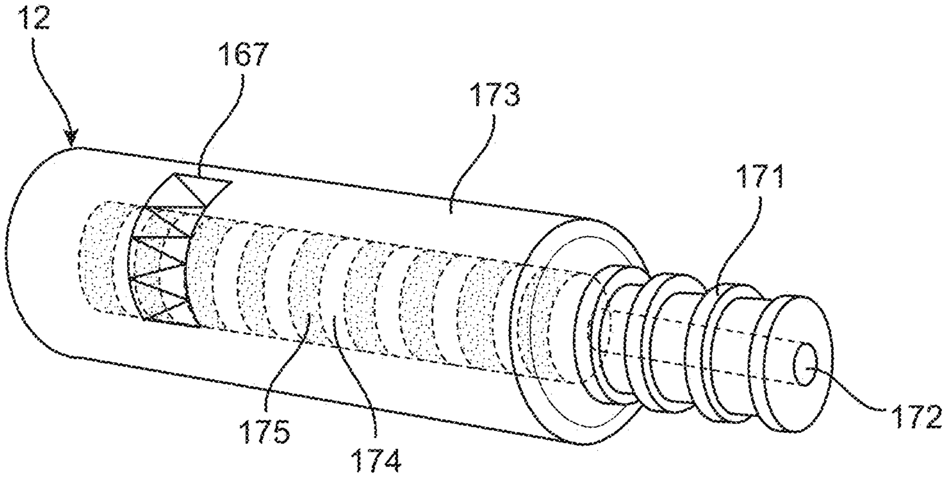

An alternative embodiment of the ground electrode 167 is shown in FIG. 28. Ground electrode 167 on the outside of the controller 12.

Figure 37:
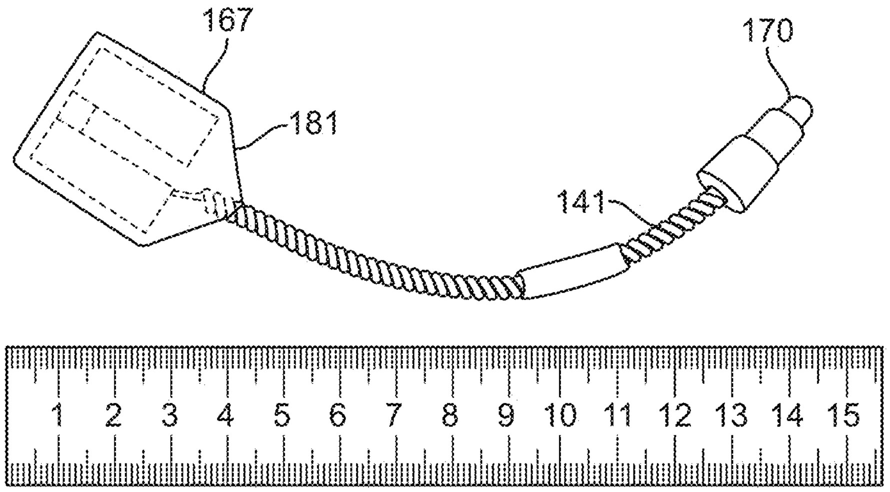
FIG. 37 is a photo of a C-shaped ground electrode.

The platinum C-shaped ground electrode 167 shown in FIG. 37 is embed in silicone 181 with a red helical lead wire 141 that is attached to a standard electrical terminal 169. Dacron mesh is used to assist secure the electrode and wire to tissue.

Figure 29:
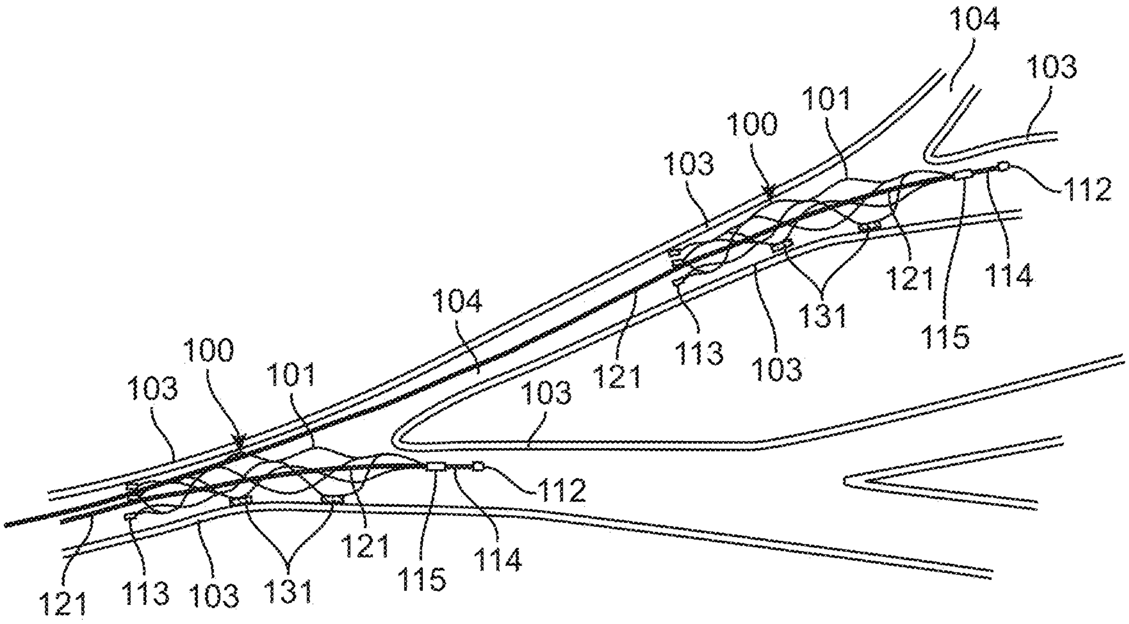
FIG. 29 is a diagrammatic illustration showing multiple vessels with multiple devices.

FIG. 29 shows a vessel with multiple devices 100 inserted in different vessels 104 to access different areas.

Figure 30:
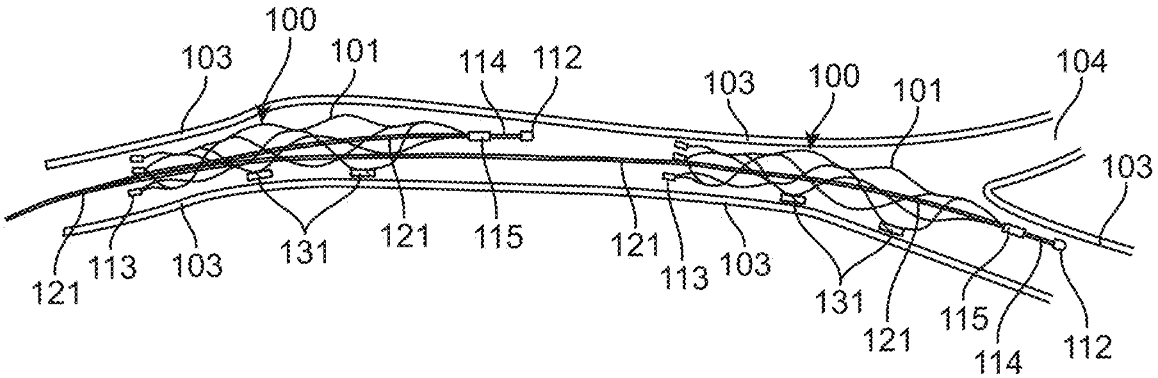
FIG. 30 is a diagrammatic illustration showing a single vessel with multiple devices.

FIG. 30 shows a single vessel 104 with multiple devices 100 implanted to cover a larger area.

Figure 31:
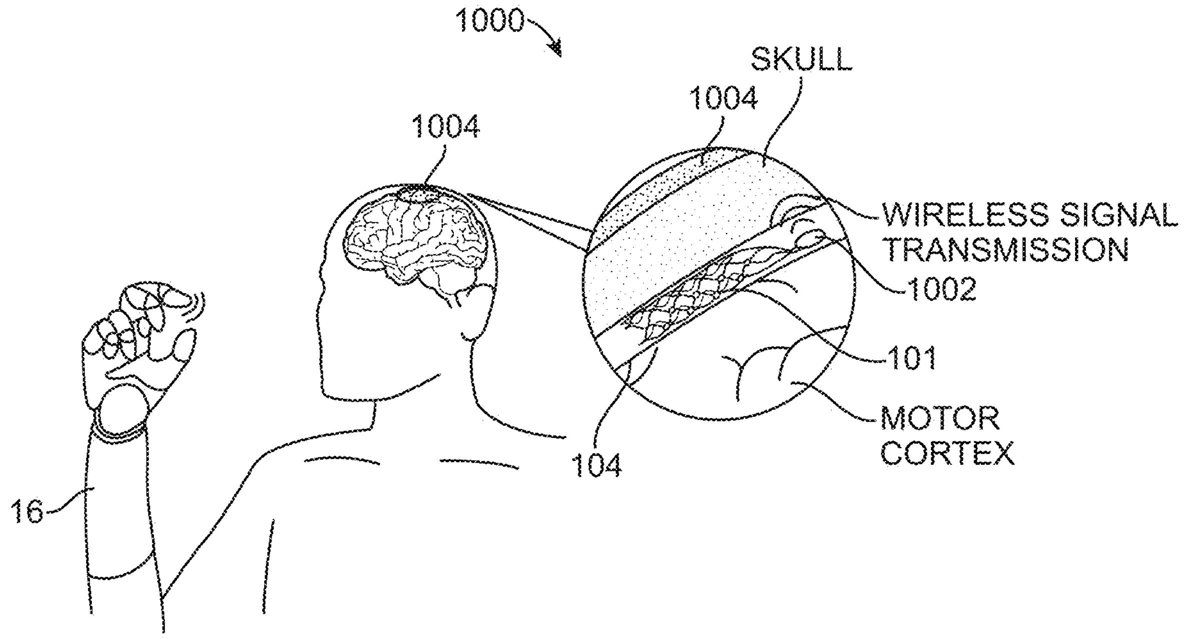
FIG. 31 is a diagrammatic illustration of a wireless electrode system.

FIG. 31 a wireless electrode system 1000 showing electrodes mounted on a stent 101 within a blood vessel 104 overlying the motor cortex in a human that are picking up neural information and relaying this information to a wireless transmitter 1002 located on the stent 101. Note the stent 101 has been deployed and the stylet has been removed (ie, only the stent 101, electrodes, electrode wires and wireless system 1002 remains). The information is wirelessly transmitted through the skull to a wireless received 1004 placed on the head, which in turn, decodes and transmits the acquired neural information to a prosthetic limb 16.

Figure 32:
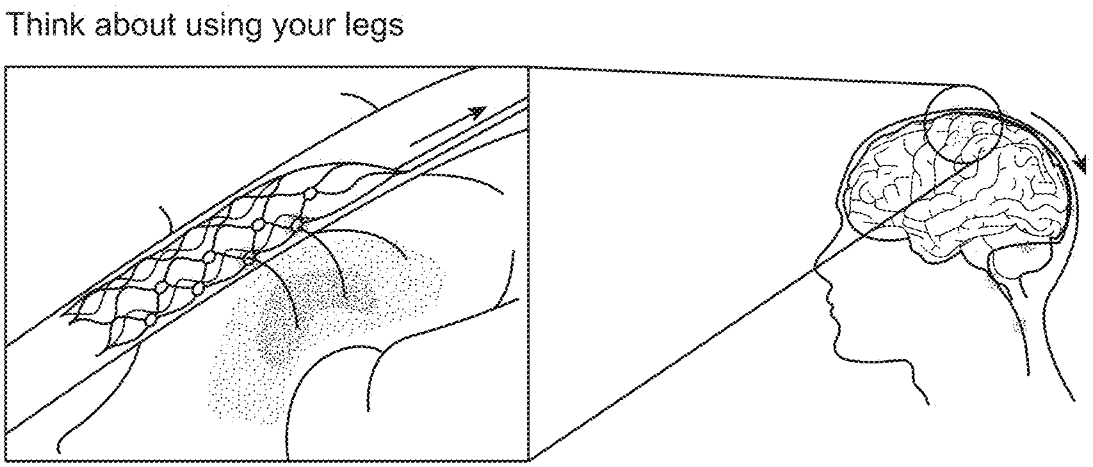
FIG. 32 is a diagrammatic illustration of the system being used to record neural information or stimulation of neurons from the superior sagittal sinus (SSS) or branching cortical veins of a patient using the device.

As shown in FIG. 32, the device 100 can be used to record neural information or stimulation of neurons from the superior sagittal sinus (SSS) or branching cortical veins of a patient using the device 100, including the steps of: (a) implanting the device in either the superior sagittal sinus or branching cortical veins; (b) receiving activity; and (c) generating data representing said activity; and (d) transmitting said data to a control unit. Stent 101 implanted in SSS over motor cortex acquiring (i.e. receives) signals that are fed through the wire to external equipment 12.

Figure 33:
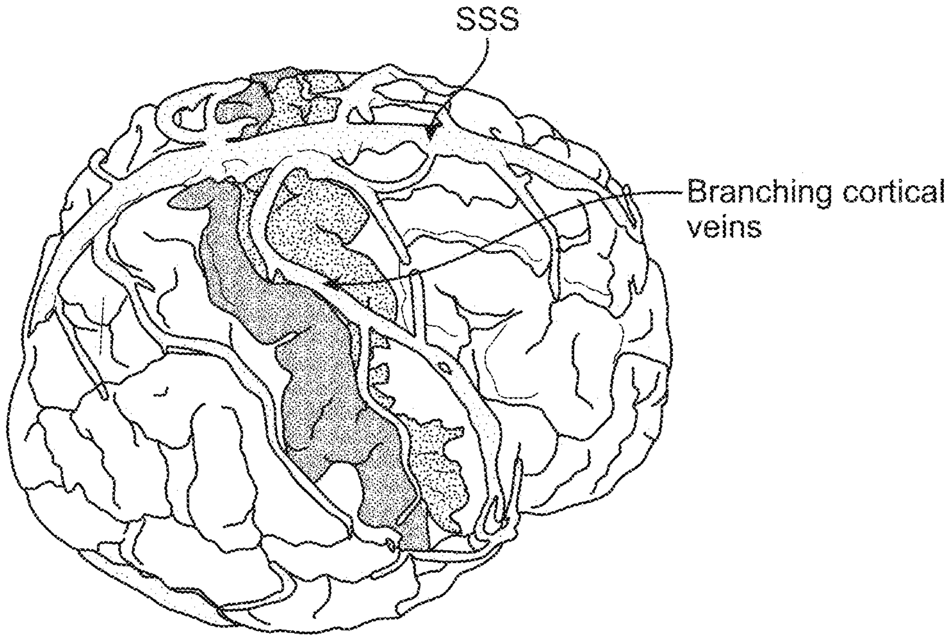
FIG. 33 shows an image reconstruction of a human brain (eyes facing left) demonstrating superior sagittal sinus and branching cortical veins near the motor cortex (red) and sensory cortex (yellow).

FIG. 33 shows an image reconstruction of a human brain (eyes facing left) demonstrating superior sagittal sinus and branching cortical veins near the motor cortex (red) and sensory cortex (yellow)

Figure 34:
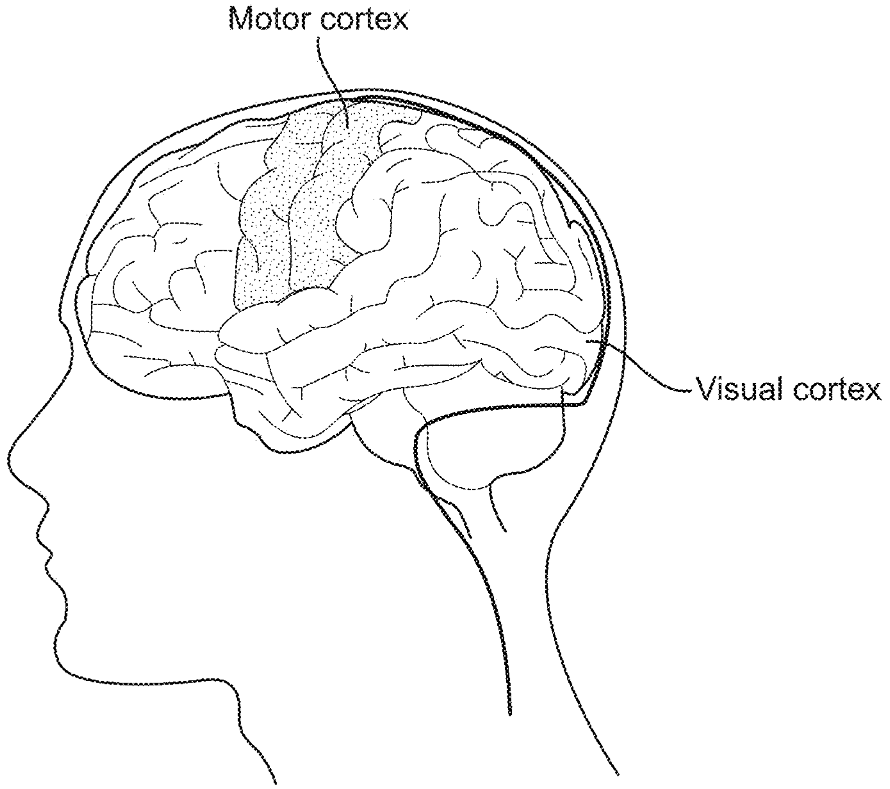
FIG. 34 is a diagrammatic illustration showing a method for stimulation and recording neural information or stimulation of neurons from the visual cortex of a patient using the device.

FIG. 34 shows a method of for stimulation and recording neural information or stimulation of neurons from the visual cortex of a patient using the device 100, including the steps of: (a) implanting the device in a vessel in the visual cortex of the patient; and (b) recording neural information associated with the vessel or stimulating neurons in accordance with received stimulation data.

Figure 35:
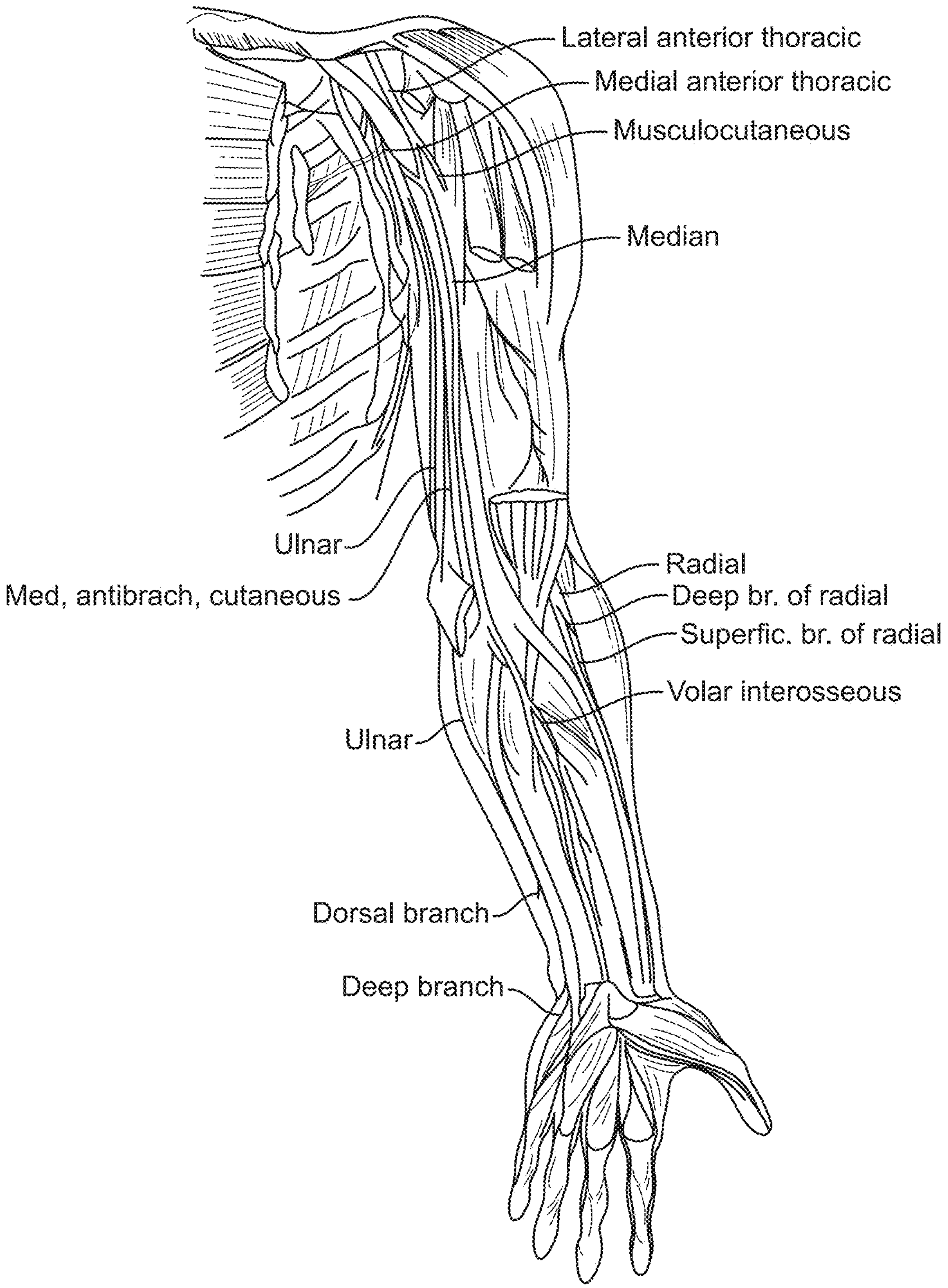
FIG. 35 is a diagrammatic illustration showing vessels and muscles in a human arm.

As particularly shown in FIG. 35, the device 100 is delivered through a vessel 104 deposited in a muscle for direct muscular stimulation or recording.

The device 100 can be delivered through a vessel adjacent to a peripheral nerve (such as shown in FIG. 35) for stimulation or recording.

Figure 36:
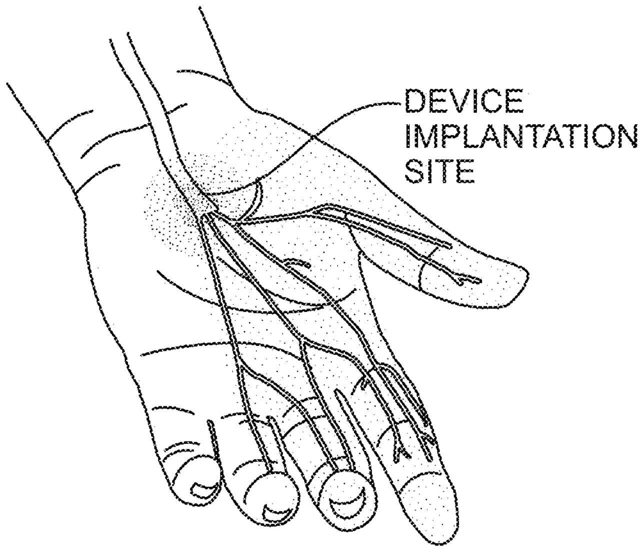
FIG. 36 is an illustration of a human hand showing possible implant location to enable neural stimulation or measurement.

The device is delivered through a vessel adjacent to a sympathetic or parasympathetic nerve for stimulation or ablation As shown in FIG. 36, one example of a peripheral nerve (the median nerve in this example) showing possible implant location to enable neural stimulation or measurement.

Figure 38A:
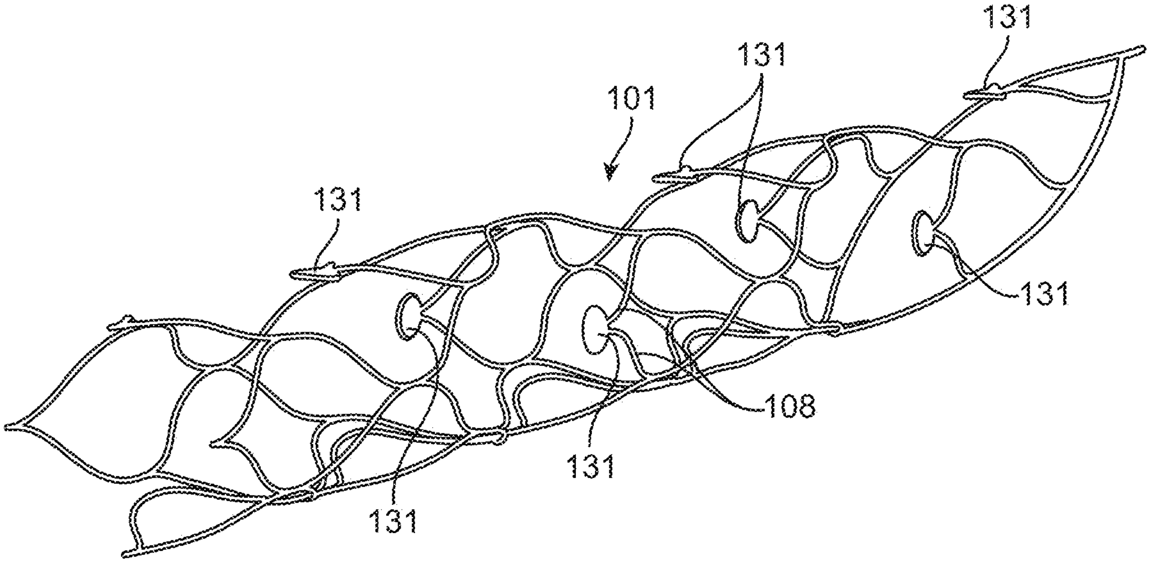
FIGS. 38A-38D illustrate examples of stents or scaffoldings having a plurality of electrodes disposed about the stent body.

FIG. 38A illustrates another example of a stent or scaffolding 101 having a plurality of electrodes 131 disposed about the stent 101 body. For purposes of illustration, the stent 101 is shown without any connecting structure that electrically couples the electrodes to leads or other such structure that allows electrical communication between the electrodes and control unit as described above. In the illustrated variation, the electrodes 131 are dispersed about the body of the stent 101 and are located at the joining or apex of joining struts 108. In such a configuration, where instead of having cells shaped like diamonds, the cells are shaped like a 'V'. This configuration can enhance the apposition between the electrodes 131 and the tissue or vessel wall.

FIG. 38A also illustrates a variation of a stent 101 that can be fabricated where stent structure comprises an integrated conductive layer that extends through a portion or more of the stent strut 108 and where the electrode 131 is formed through an exposed portion of the integrated conductive layer. Such a stent configuration, as described in detail below, permits a stent 101 electrode 131 assembly, which embeds electrodes and conductive electrode tracks into the stent lattice or strut itself. Such a construction reduces or eliminates the requirement to use fixation methods (i.e., adhesives, glues, fasteners, welds, etc.) to mount electrodes to the body of the stent. Such a construction further reduces or eliminates the need to further weld or electrically connect electrodes to wires. Another benefit is that conventional wire-connected-electrodes require accommodation of the wires about the stent struts and through the body of the stent.

Figure 38B:
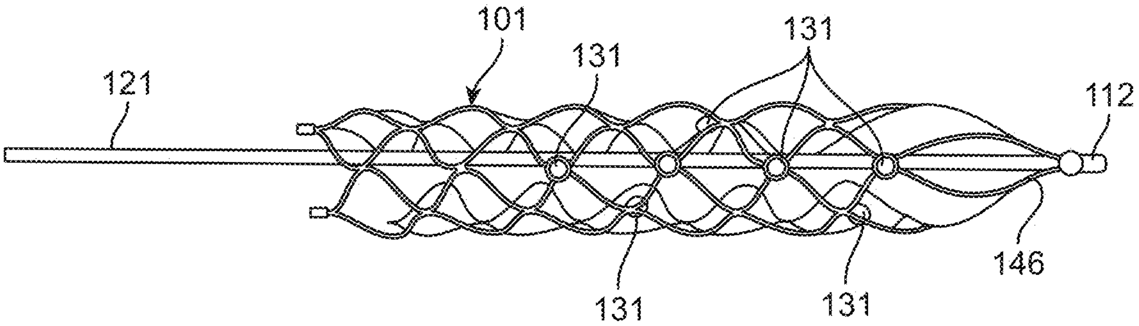
Figure 38C:
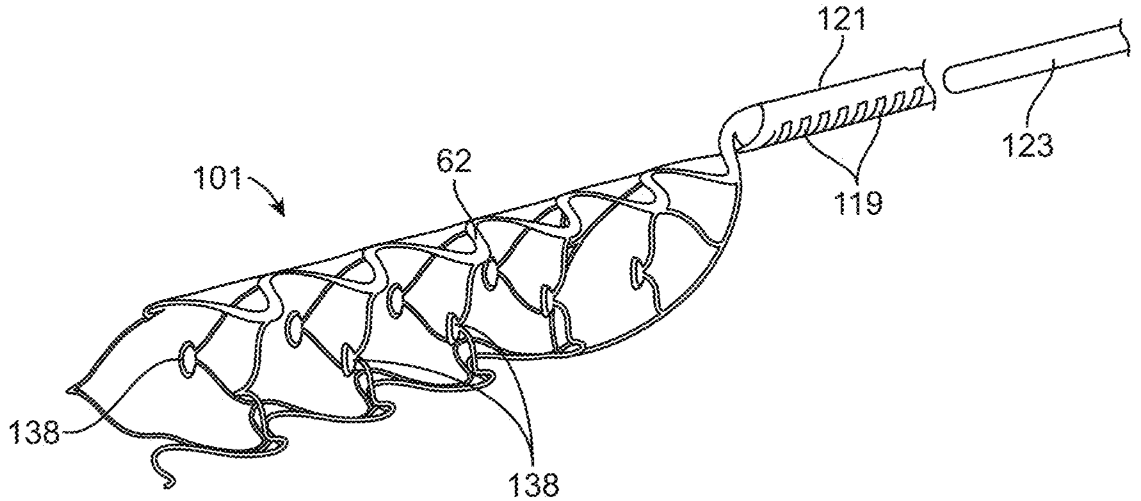
Figure 38D:
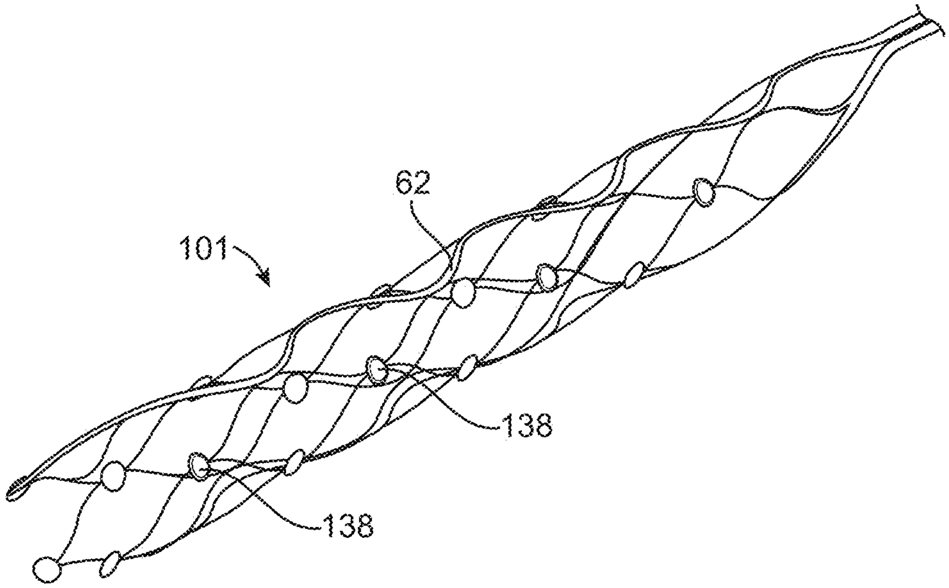

FIG. 38B illustrates a stent structure 101 with integrated electrodes 131, where the stent structure is coupled to a shaft 121 at a distal end 146. The shaft, as described herein, can electrically couple the electrodes 131 to one or more control units (not shown) as described herein. In one example, the shaft 121 can comprise a guidewire, push wire other tubular structure that contains wires or conductive members extending therein and are coupled to the conductive layer of the stent at the distal end 146. Alternatively, FIGS. 38C and 38D shows a variation of stents 101 that can be fabricated such that the shaft 121 is part of or integral with the stent structure, where the conductive layer extends through a portion or all of the stent to the shaft 121. Such a construction further eliminates the need for joining the shaft to the stent structure at the working end of the stent. Instead, the joining of the stent structure (forming the shaft) to a discrete shaft can be moved proximally along the device. Such a construction allows the working end of the stent and shaft to remain flexible. The stent structures shown in FIGS. 38C and 38D can also include an optional reinforced section 62 as discussed above. FIG. 38C further illustrates a hollow shaft 121, which allows insertion of a stylet 123 therethrough to assist in positioning of the device or permits coupling of wires or other conductive members therethrough. Furthermore, the shaft 121 can include any number of features 119 that improve flexibility or pushability of the shaft through the vasculature.

The electrical connection of the electrodes 131 to leads extending through the device can be accomplished by the construction of one or more connection pads (similar in construction to the electrodes described below) where the size of the pads ensures sufficient contact with the wire/lead, the type of pads ensures robustness and reduces track fatigue when crimped and attached. The section containing the pads can be compressed into a tube at, for example, distal section 146 to enable insertion of a cable 121.

In certain variations, the connection pads should be able to feed through the catheter. Furthermore, the connection pads 132 can include one or more holes or openings that enable visual confirmation that the pads are aligned with contacts on the lead. These holes/openings also enables direct/laser welding or adhesion of the contact leads (inside tube 121) and the contact pads (on the inside of the tube spanning through the hole to the outside)

In one example, a coaxial-octofilar cable (i.e. an inner cable with 8 wires positioned inside an outer cable having 8 wires) is used to enhance fatigue resistance and to ensure that wires can fit within constraints (i.e., can be inserted through a sufficiently small catheter, and can have an internal stylet as required).

Figure 39A:
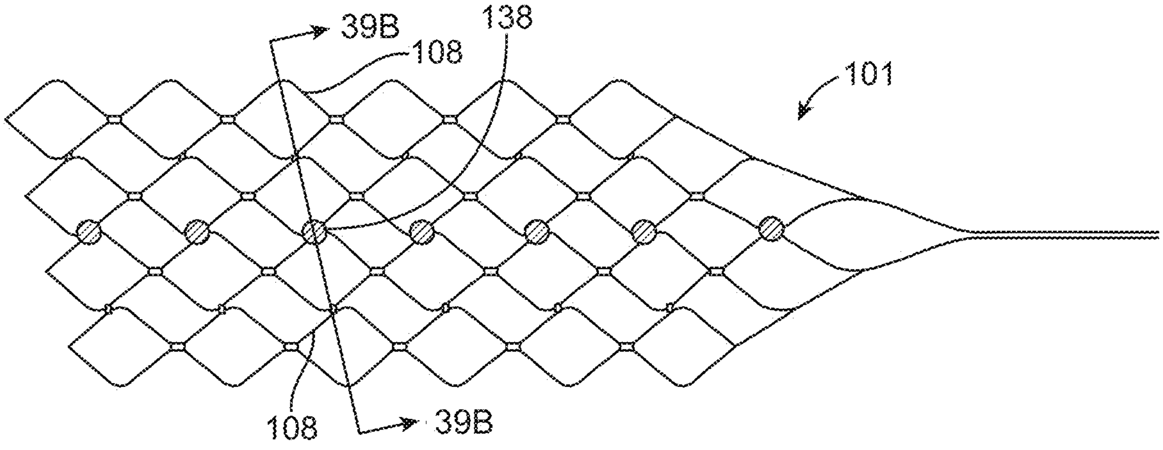
FIGS. 39A-39C illustrate an example of integrated or embedded electrodes.
Figure 39B:
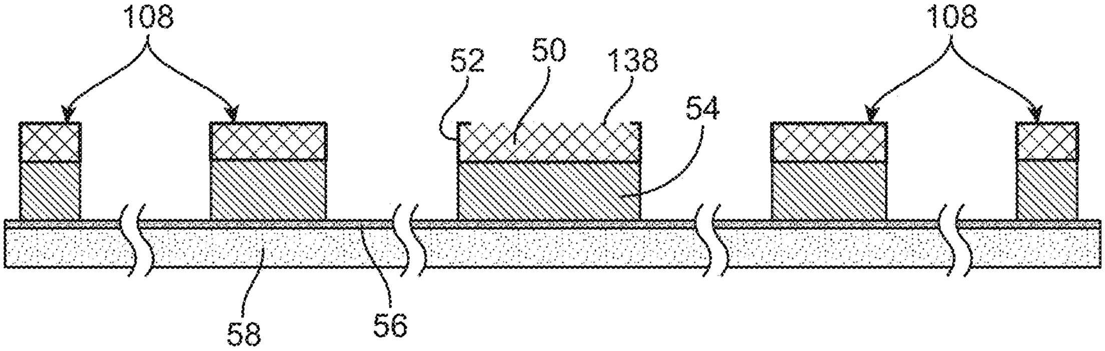
Figure 39C:
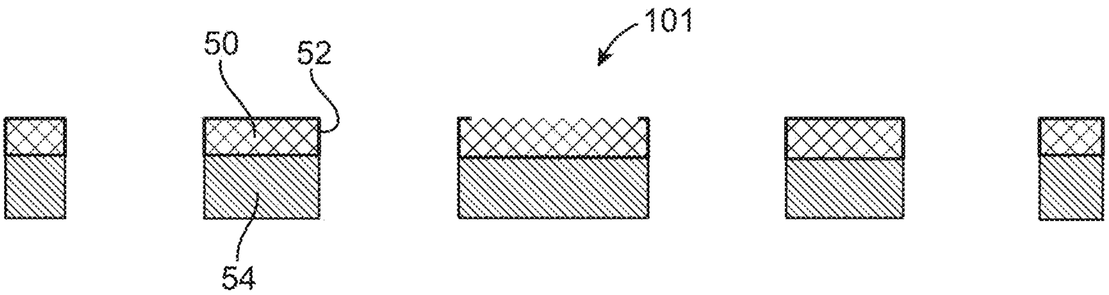

FIGS. 39A-39C illustrate one example of a stent structure 101 constructed with an embedded electrode and conductive path. FIG. 39A illustrates an example of a stent structure 101 in a planar configuration with electrodes 138 in a linear arrangement for purposes of illustration only. Clearly, any configuration of electrodes is within the scope of this disclosure. Specifically, in those variations of stent structures useful for neurological applications, the stent structure can comprise a diameter that is traditionally greater than existing neurological stents. Such increased diameter can be useful due to the stent structure being permanently implanted and while requiring apposition of electrodes against the vessel/tissue wall. Moreover, in some variations, the length of such stent structures can include lengths up to and greater than 20 mm to accommodate desired placement along the human motor cortex. For example, variations of the device require a stent structure that is sufficiently long enough to cover the motor cortex and peripheral cortical areas. Such lengths are not typically required for existing interventional devices aimed at restoring flow or addressing aneurysms or other medical conditions. In addition, in certain variations, the electrical path between certain electrodes can be isolated. In such a case, the electrically conductive material 50 can be omitted from certain stent struts to form a pattern that allows an electrode to have an electrical conduction path to a contact pad or other conductive element but the electrical conduction path is electrically isolated from a second electrode having its own second electrically conductive path.

Placement of the electrodes in a specific pattern (e.g., a corkscrew configuration or a configuration of three linear (or corkscrew oriented) lines that are oriented 120 degrees from each other) can ensure a deployed electrode orientation that directs electrodes towards the brain. Once implanted, orientation is not possible surgically (i.e., the device will be implanted and will be difficult if not impossible to rotate). Therefore, variations of the device will be desirable to have an electrode pattern that will face towards the desired regions of the brain upon delivery.

Electrode sizing should be of a sufficient size to ensure high quality recordings and give large enough charge injection limits (the amount of current that can be passed through the electrodes during stimulation without damaging the electrodes which in turn may damage tissue). The size should also be sufficient to allow delivery via a catheter system.

FIGS. 39B and 39C illustrates a cross-sectional view of the stent structure of FIG. 39A taken along line 39B-39B to further illustrate one variation of a manufacturing technique of using MEMS (microelectrical mechanical systems) technology to deposit and structure thin film devices to fabricate a stent structure with electrodes and a conductive path embedded into the stent lattice or struts. The spacing of the struts in FIGS. 39B and 39C are compressed for illustrative purposes only.

As discussed above, embedding the electrode and conductive path presents advantages in the mechanical performance of the device. Furthermore, embedding of electrodes provides the ability to increase the number of electrodes mounted on the structure give that the conductive paths (30-50 μm×200-500 nm) can be smaller than traditional electrode wires (50-100 μm).

Manufacture of thin-film stents can be performed by depositing Nitinol or other superelastic and shape memory materials (or other materials for deposition of electrodes and contacts (including but not limited to gold, platinum, iridium oxide) through magnetron sputtering in a specific pattern (56) using a sacrificial layer (58) as a preliminary support structure. Removal of the support structure (54) enables the thin film to be further structured using UV-lithography and structures can be designed with thicknesses corresponding with radial force required to secure the electrodes against a vessel wall.

Electrical insulation of electrodes is achieved by RF sputtering and deposition of a non-conductive layer (52) (eg, SiO) onto the thin-film structure (54). Electrodes and electrode tracks (50) are sputter deposited onto the non-conductive layer (using conductive and biomedically acceptable materials including gold, Pt, Ti, NiTi, PtIr), with an additional non-conductive layer deposited over the conductive track tfor further electrical isolation and insulation. As shown, conducting path 50 is left exposed to form the electrode 138 (similarly, a contact pad area can remain exposed). Finally, the sacrificial layer 56 and substrate are removed leaving the stent structure 101 as shown in FIG. 39C.

In certain variations where the base structure 54 comprises superelastic and shape-memory materials (i.e. Nitinol), the stent structure 101 can be annealed in a high vacuum chamber to avoid oxidation during the annealing process. During heat treatment, the amorphous Nitinol structure 54 crystallizes to obtain superelasticity and can be simultaneously shape set into a cylindrical or other shape as desired. The structure 101 can then be heat treated.

Figure 40A:
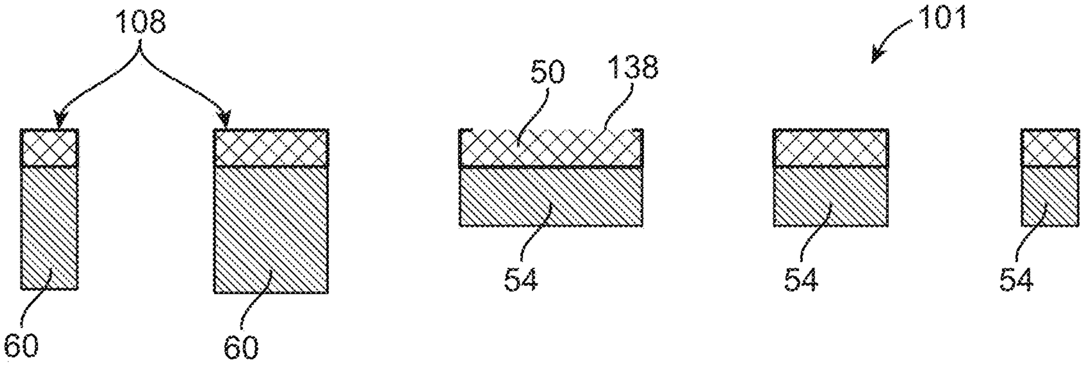
Figures. 40A-40B show an example of a stent structure fabricated with dimensional variation to impart specific characteristics to the stent.
Figure 41A:
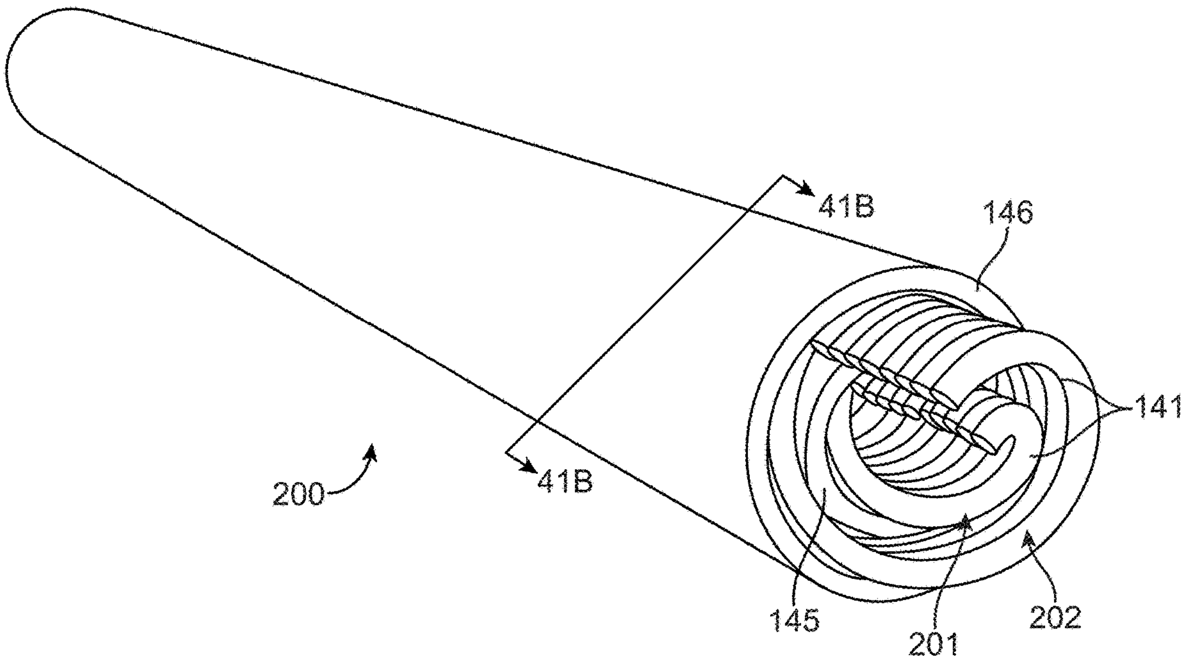
FIGS. 41A-41E illustrate a variation of a connector.
Figure 41B:
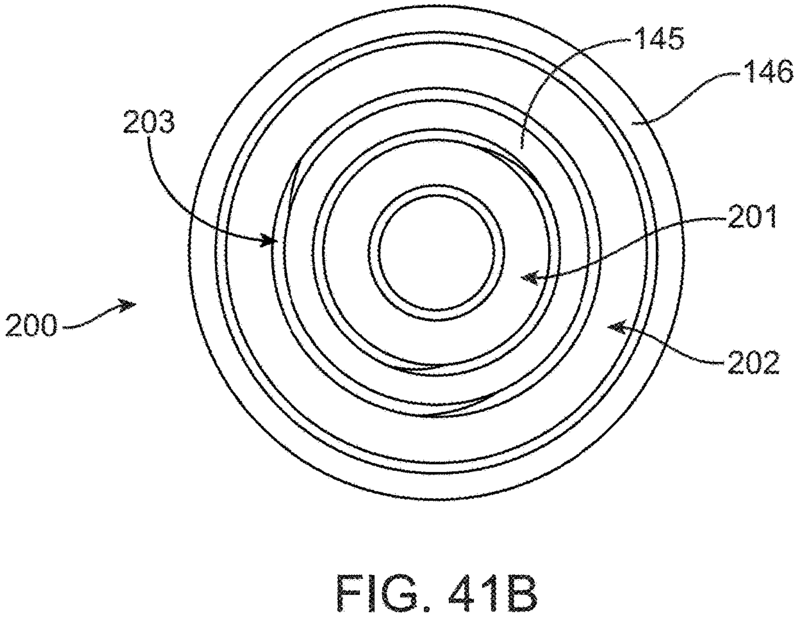

FIG. 40A, which is a partial sectional view of taken along lines 40A-40A of FIG. 41B, illustrate an additional variation of a stent structure 101 fabricated via MEMS technology where one or more stent struts 108 can be dimensionally altered to impart desired structural or other aspects to the stent structure 101. For example, in the illustrated variation, certain stent struts 108 are dimensionally altered such that the support material 60 comprises a greater thickness than adjacent stent structures 108. However, such dimensional variation is not limited to thickness but can also include width, shape, etc.

Figure 40B:
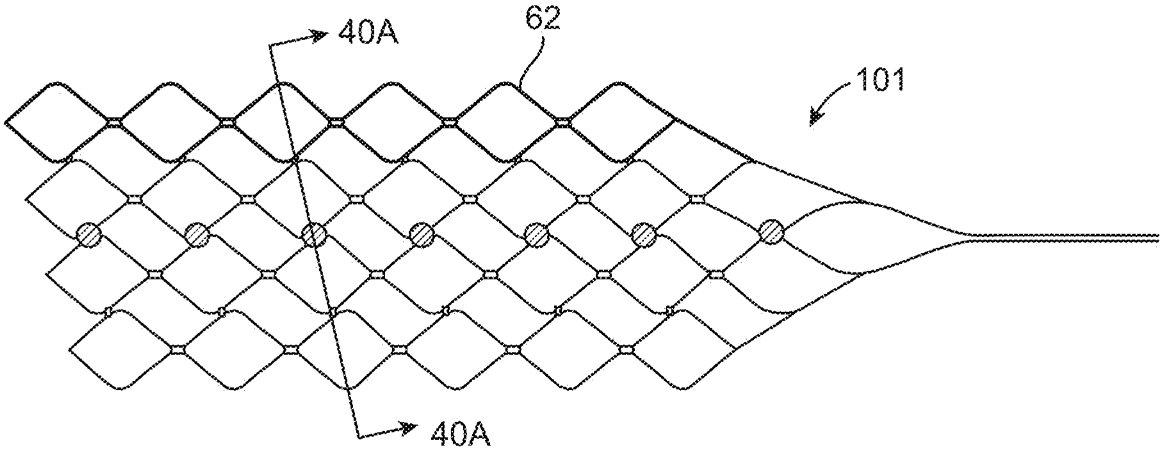

FIG. 40B illustrates the stent structure 101 resulting from the dimensionally altered struts resulting in a sinusoidal section 62 of the stent structure 101 that comprises a greater stiffness (resulting from the increased thickness). Such a configuration allowing the stent device to be pushed through a catheter rather than conventional requirements to be unsheathed (where the sheath is pulled back over the stent). Conventional stents are made from a thin lattice of Nitinol diamonds or cells. This sinusoidal section 62 can function like a backbone and gives forward pushing strength to the device without restricting super-elasticity and the ability for the stent to compress and expand. Clearly, any number of variations of dimensionally altered strut sections are within the scope of this disclosure.

FIGS. 41A-41E illustrate various aspects of a variation of a connector 200 that can be in electrical communication with a stent (e.g., stent 101) and a receptacle (e.g., control unit 12). For purposes of illustration, the connector 200 is shown isolated from the stent 101 and the receptacle 12. As described above, the connector 200 can allow electrical communication between the electrodes and the control unit.

FIG. 41A illustrates that the connector 200 can have a dual-octofiler cable (also referred to as a coaxial-octofiler cable). The dual-octofiler cable can have a first coil 201 (e.g., inner coil) and a second coil 202 (e.g., outer coil). The first and second coils 201, 202 can each have 8 wires 141. Other numbers of wires, more or less, are also appreciated. The first coil 201 can be positioned within a lumen of the second coil 202. The first coil can be positioned within a lumen of an internal tubing 145. The first and/or second coils 201, 202 can be positioned within a lumen of an external tubing 146. The first and second coils 201, 202 can be wound coils. The first and second coils 201, 202 can be helical coils. For example, the first coil 201 can be wrapped along an inner surface of the internal tube 145 and the second coil 202 can be wrapped along an outer surface of the internal tube 145. As described above, the dual-octofiler configuration can be used to enhance fatigue resistance and to ensure that wires can fit within constraints (i.e., can be inserted through a sufficiently small catheter, and can have an internal stylet as required).

An insulator (e.g., polyurethane) can cover one or more wires 141 of the coils 201, 202 (i.e., the wires 141 can be insulated). An insulator (e.g., polyurethane) can be positioned between the first and second coils 201, 202. For example, the internal tube 145 can be an insulator that can be positioned between the first and second coils 201, 202. An insulator (e.g., polyurethane) can cover the first and/or second coils 201, 202 (i.e., the first and second coils 201, 202 can be insulated).

The first coil 201 can have a length that is less than, greater than, or equal to the length of the second coil 202. For example, the first coil 201 can be longer than the second coil 202. The first coil 201 can have a diameter that is less than, greater than, or equal to the diameter of the second coil 202. The first and/or second coils 201, 202 can each have one or more diameters. For example, the first coil 201 can have two diameters and the second coil 202 can have one diameter. The first coil 201 can have a first diameter and a second diameter. The first diameter can correspond to where the first coil 201 is positioned within the second coil 202 and the second diameter can correspond to where the first coil 201 is not positioned within the second coil 202 (e.g., where it extends past the first coil 201). Other arrangements are also appreciated.

Although not shown in FIG. 41A, the external shaft 146 can comprise contacts 151 and separators 174 (e.g., insulators). The separators 174 can be positioned next to contacts 151 to keep the contacts 151 electrically insulated from one another. The wires 141 of the first and second coils 201, 202 can be electrically connected to the contacts 151. For example, the 8 wires 141 of the first coil 201 and the 8 wires 141 of the second coil 202 can each be electrically coupled to a corresponding contact 151.

The first coil 201 can allow a stylet 148 (not shown) to travel through it. For example, the first coil 201 can define a lumen that allows a stylet 148 to pass through the first coil 201. The inner surface of the first coil 201 can be insulated and/or not insulated.

The first and second coils 201, 202 can have a wound section and an unwound section. For example, the first and second coils 201, 202 can transition from a wound section to an unwound section. The wound section have helical wires and the unwound section can have straight, curved (e.g., have one or more bends), and/or angled (e.g., have one or more bends) wires. The wound and unwound sections can be flexible and/or rigid. For example, the wound section can be flexible and the unwound section can be rigid.

The first and second coils 201, 202 can have a helical section and a non-helical section. For example, the first and second coils 201, 202 can transition from a helical section (e.g., where the wires 141 define a helix) to a non-helical section (e.g., where the wires 141 do not define a helix). For example, the wires 141 in the non-helical section can be unwound to no longer form a coil. The wires 141 in the non-helical section can be straight, curved (e.g., have one or more bends), and/or angled (e.g., have one or more bends). The helical and non-helical sections can be flexible and/or rigid. For example, the helical section can be flexible and the non-helical section can be rigid.

The first and second coils 201, 202 can each have one or more channels. For example, the first and second coils 201, 202 can each have 8 channels. Other numbers of channels, more or less, are also appreciated (e.g., 9 to 16 channels, or more). Other numbers of coils are also appreciated, for example, 3 or more coils. For example, it will be appreciated that another coil can be positioned within the lumen of the first coil 201 and/or on the outside of the second coil 202.

FIG. 41B illustrates a cross-sectional view of the connector 200 shown in FIG. 41A taken along the line 41A-41A to further illustrate the first and second coils 201, 202 of the dual-octofiler coil configuration. FIG. 41B also illustrates that the first coil 201 can step-up 203 in diameter to match or otherwise approach the diameter of the second coil 202. The step-up 203 can occur somewhere along the length of the first coil 201 and somewhere along the length of the second coil 202. For example, the first coil 201 can step-up 203 at about the midpoint of the first coil 201 and at an end of the second coil 202 (e.g., a terminal end). The first coil 201 can step-up 203 to contact the leads 151, for example, so that uniformly sized leads 151 can be used. The first coil 201 can step-up 203 to attach to the leads 151. However, it will be appreciated that the leads 151 can have one or more sizes. With or without the step-up 203, the receptacle 12 can have a step in it so that the contacts 175 of the receptacle 12 can make contact with the contacts 151 in contact with the first coil 201. The various components of the dual octofilar cable can have the various dimensions shown (in inches).

Figure 41C:
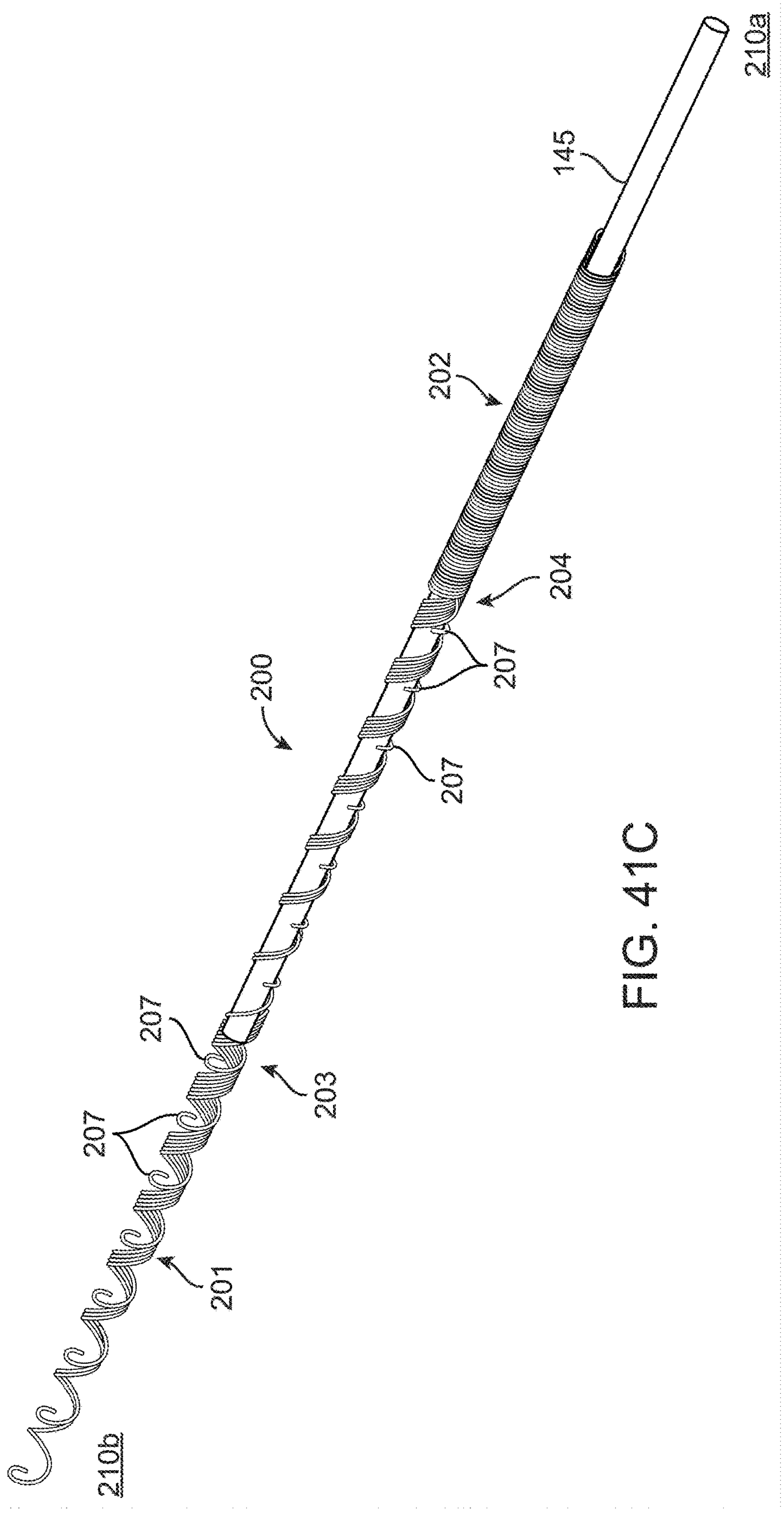

FIG. 41C illustrates another perspective view of the connector 200 of FIG. 41A, but with the outer shaft 146 made transparent for purposes of illustration. As described above, the second coil 202 can be wrapped around the inner shaft 145 and the first coil 201 can have a step-up 203. FIG. 41C illustrates that the 8 wires 141 of the first and second coils 201, 202 can have terminal ends 207. As shown, the wires 141 of the second coil 202 can terminate first, followed by the wires 141 of the first coil 201. The terminal ends 207 of the second coil 202 can attach to the first 8 leads 151 of the connector 200 and the terminal ends 207 of the first coil 201 can attach to the second 8 leads 151 of the connector 200. The first 8 leads 151 can be closer to a first end 210*a* of the connector 200 and the second 8 leads 151 can be closer to a second end 210*b* of the connector 200. Any connection sequence is appreciated, including, for example, connecting from proximal to distal (e.g., from first end 210*a* to second end 210*b*) as shown, from distal to proximal, alternating, etc. The terminal ends 207 can be electrically coupled to contacts 151 as described above (e.g., by welding). The terminal ends 207 can be exposed to the contacts 151 to establish an electrical path between the leads 151 and the electrodes 131, 138.

FIG. 41C also illustrates that the helix angle of the second coil 202 can change, for example, at position 204. The helix angle of the second coil 202 can increase or decrease. For example, the helix angle can increase near where the second coil 202 makes contact with the first contact 151. Other numbers of changes in the helix angle of the second coil 202, more or less, are also appreciated (e.g., including zero change to two or more changes).

Figure 41D:
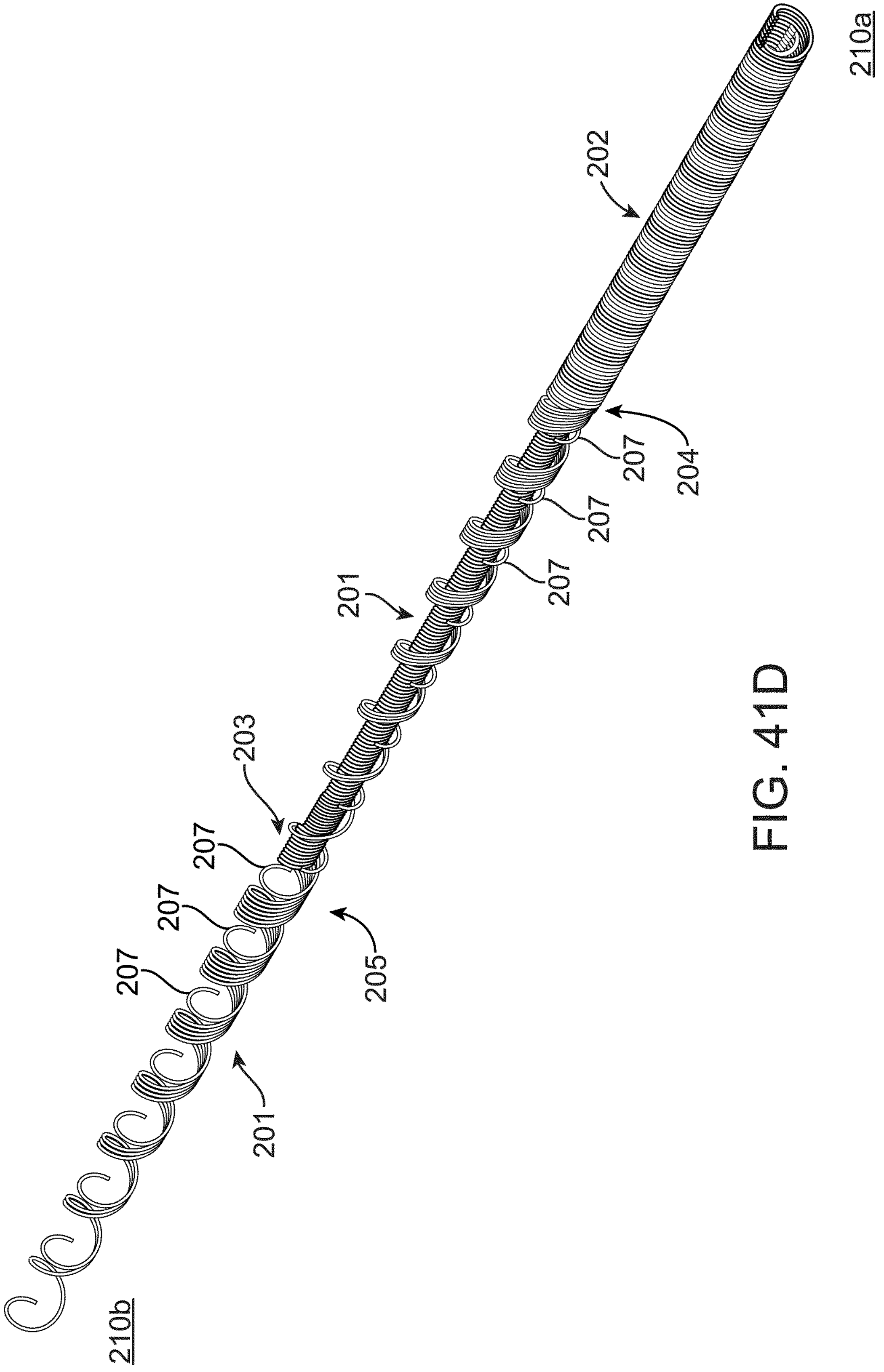

FIG. 41D illustrates another perspective view of the connector 200 of FIG. 41A, but with the inner and outer shafts 145, 146 made transparent for purposes of illustration. FIG. 41D illustrates that the helix angle of the first coil 201 can change, for example, at position 205. The helix angle of the first coil 201 can increase or decrease. For example, the helix angle can increase near where the last terminal end 207 of the second coil 202 makes electrical contact with an eighth contact 151. Other numbers of changes in the helix angle of the first coil 16, more or less, are also appreciated (e.g., including zero change to two or more changes).

Figure 41E:
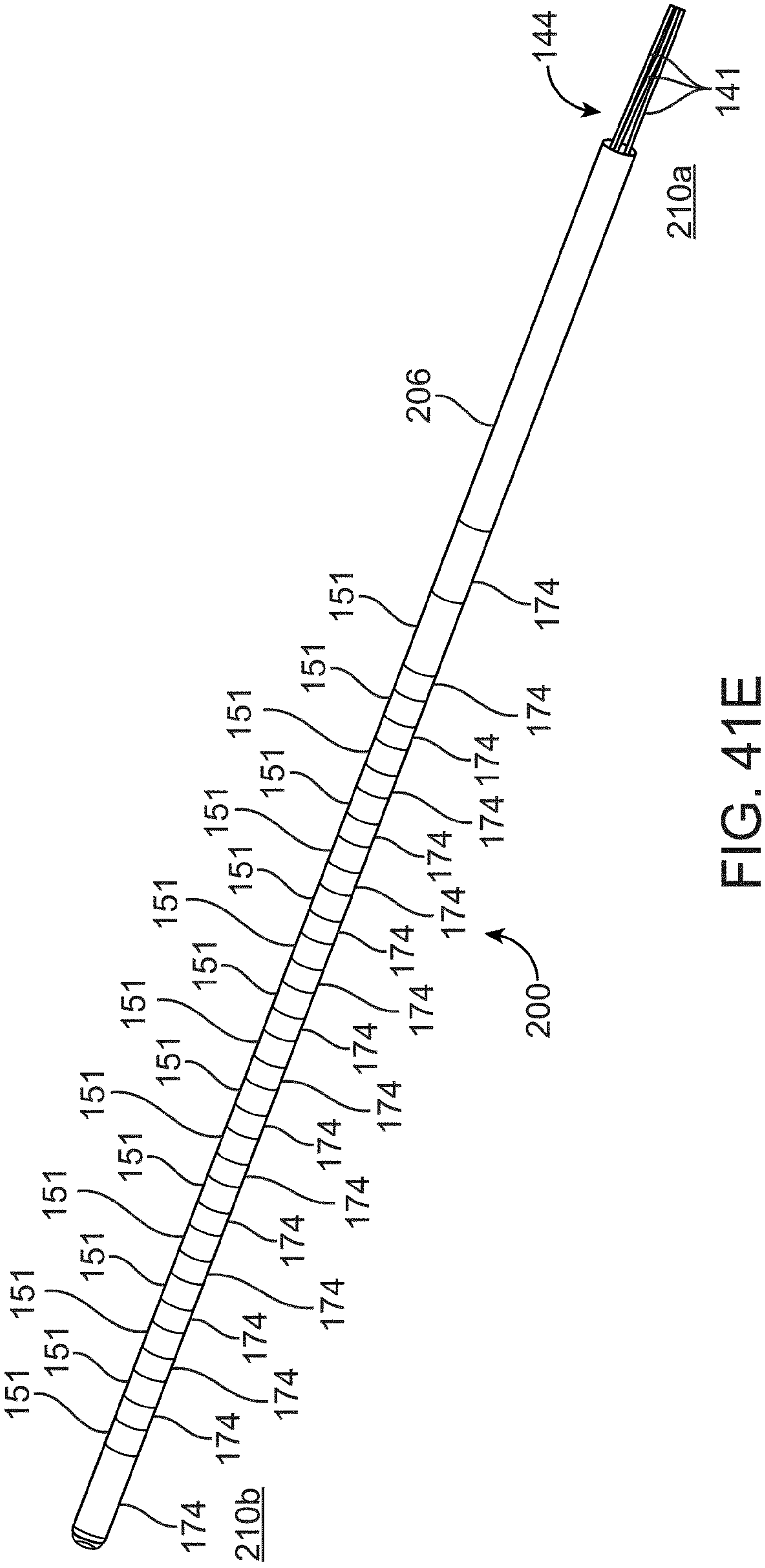

FIG. 41E illustrates the connector 200 of FIG. 41A with the leads 151 and separators 174 shown. The leads and separators 151, 174 can be positioned relative to one another in an alternating pattern. As described above, each wire 141 of the first and second coils 201, 202 terminate on a contact 151. The wires/filars 141 are exposed and attached (e.g., welded) to the inner surface (e.g., inner diameter) of the leads 151.

The connector 200 can be inserted into and/or attached to a receptacle 12 as described above. The connector 200 can be plugged into a receptacle 12 as described above. FIG. 41E illustrates that the connector 200 can have a retention member 206 (e.g., retention ring 206) that can engage with and/or attach to the receptacle 12. To accomplish this, the retention member 206 can form a ring or a ring-like structure, although other shapes are also appreciated. For example, the receptacle 12 can be screwed onto the retention member 206. The retention member 206 can have internal and/or external screw threads. For example, the retention member 206 can comprise a set screw. The retention member 206 can have a longer longitudinal dimension than one of the contacts 151.

The retention member 206 can be rigid to provide the connector 200 with structural support before, during and after implantation. Other parts of the connector 200 can be flexible so that the connector 200 can navigate or otherwise conform to the tortuosity of a blood vessel. For example, the portion of the connector 200 that is between the retention member 206 and the second end 210*b* of the connector 200 can be flexible (this portion is also referred to here as the lead body). The lead body of the connector 200 can flex 90 degrees around a 6 mm radius. Other angles and radii, more or less, are also appreciated. The connector 200 (e.g., the second end 210*b* of the connector 200) can flex 45 degrees around a radius of 0.5 mm. Other angles and radii, more or less, are also appreciated. The connector 200 can be looped around a 1 cm radius. Other loop radii, more or less, are also appreciated.

In the lead body portion of the connector 200, the coils 201, 202 can be allowed to float such that they are not embedded in insulation. The coils 201, 202 can be embedded in insulation within the retention member 206 and/or within the lead body portion. The separators 174 can be overmolded to ensure a uniform diameter is present between contacts.

FIG. 41E illustrates that the lead wires 141 can extend beyond the first end 210*a* of the connector 200. The lead wires 141 that extend beyond the first end 210*a* of the connector 200 can be unwound (e.g., uncoiled) such that each wire 141 can individually connect to a connection panel (e.g., connection panel 220 described below), or otherwise connect to the connection panel in one or more bundles 144 of wires 141. For example, the lead wires 141 can transition from coiled configurations into 16 tailed ends that can connect to the connection panel. The 16 tailed ends can be straight and/or curved. The connection panel can electrically couple the connector 200 to the electrodes 131, 138. For example, FIG. 41E illustrates that the first and second coils 201, 202 can be unwound and grouped into three bundles 144 of lead wires 141. Other numbers of bundles, more or less, are also appreciated. Wires from the first and second coil 201, 202 can be bundled with first coil 201 wires 141 and/or with second coil 202 wires 141. It is appreciated that individual wires 141 and one or more bundles of wires 144 can extend from the connector 200 to connect with the connection panel. The wires 141 can unwind/uncoil over some dimension within the retention member 206 and/or over some dimension within the rest of the connector 200. The wires 141 and/or bundles 144 that extend from the connector toward the stent 101 can be rigid and/or flexible.

The wires 141 can be directly connected to the stent 101, for example, with laser welding. For example, the wires 141 can be directly connected to pads on the stent 101. The wires 141 can be indirectly connected to the stent 101, for example, with wire bonding. For example, the wires 141 can be indirectly connected to pads on the stent 101 via connection to intermediate pads. The pads on the stent 101 can be wire bonded to the intermediate pads, for example, with jumper wires.

Figure 42:
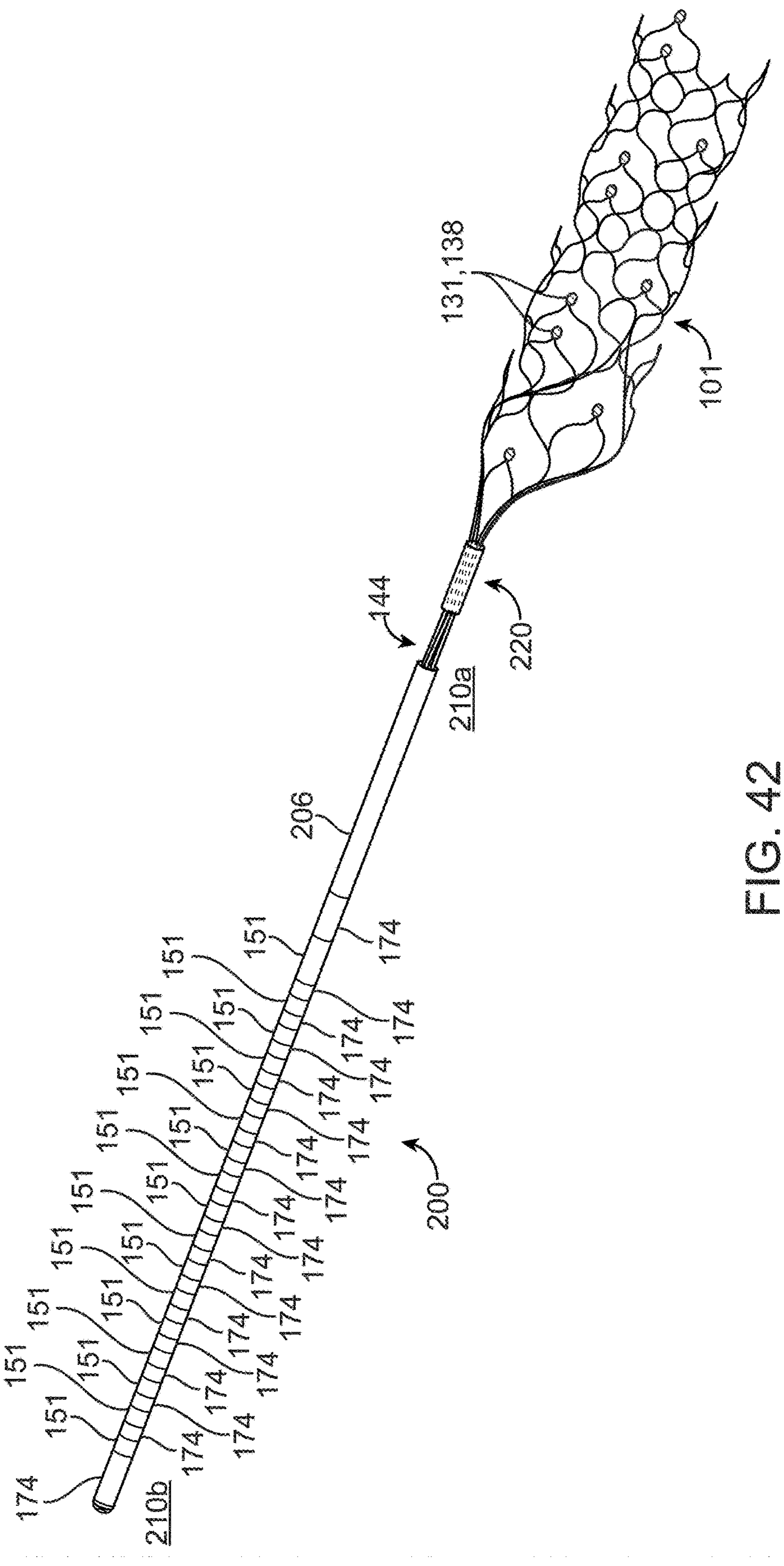
FIG. 42 illustrates a variation of a stent electrically coupled to a control panel and a connector.

FIG. 42 illustrates that the connector 200 of FIGS. 41A-41E can be electrically coupled to the electrodes 131, 138 of the stent 101 via a connection panel 220. FIG. 42 illustrates that the wires 141 of the connector 200 can be indirectly connected to the stent 101 via the connection panel 220. The connection panel 220 can have a first panel (e.g., an overlay) and a second panel (e.g., a stentrode panel) electrically coupled together. The first and second panels can each have one or more connection pads. The pads can be made of platinum or other conductive materials. The wires 141 of the connector 200 can be electrically connected to one or more pads of the first panel and the conductive paths (also referred to as electrode tracks) of the stent 101 can be electrically connected to one or more pads of the second panel. One or more jumpers can be used to electrically connect the first panel to the second panel. For example, one or more jumpers can be used to electrically connect the first panel pads to the second panel pads. The one or more jumpers can electrically connect the pads of the first panel to the pads of the second panel, thereby electrically connecting the leads 151 of the connector 200 to the electrodes 131, 138 of the stent 101. Attaching the wires/filars 141 to the first panel can advantageously provide a more stable and reliable connection than directly attaching the wires/filars 141 to the stentrode pads (e.g., to the second panel pads). The first and/or second panels can be attached to the connector 200, for example, by welding or other attachment method. The first and second panels can each have 16 pads. Other numbers of pads, more or less, are also appreciated (e.g., 1 pad to 32 or more pads). An insulating material (e.g., epoxy) can cover the connection panel 220.

More than one connection panel 220 can be used. For example, two connection panels 220 can be used. The use of two connection panels 220 can advantageously make connections easier and give more space for wire management relative to the use of only one connection panel 220 since not all 16 wires 141 are connected to the same area when two connection panels are used. The use of multiple connection panels can help provide structural support to the connection panel region when the stentrode is being pushed out of the delivery system. For example, the use of multiple connection panels can help distribute the force/axial load that is applied when the system is pushed through a delivery system (e.g., a catheter). The use of multiple connection panels is also advantageous from a processing and fatigue resistance standpoint.

The one or more connection panels 220 can be aligned with a backbone of the stent 101. For example, the one or more connection panels 220 can be aligned with struts 108, thicker struts 108, and/or with a reinforced section 62.

The transition from the dual coils 201, 202 to the leads 141 extending toward the panel 220 can include unwinding/uncoiling the first and second coils 201, 202 as described above.

The connector 200 (also referred to as an endovascular implantable lead) can be configured to transmit neural interface sensor data to an implantable telemetry unit (e.g., control unit 12). The dual-octofiler coils 201, 202 can advantageously withstand long term repetitive movement and trauma due to neck movements, among other movements. The use of dual-octofiler coils 201, 202 can advantageously reduce noise due to muscle artifacts.

The pads on the stent can be connected to the conductors in the lead body by a variety of methods including but not limited to resistance welding, laser welding (each involving direct contact between the pads on the Stentrode and the lead), and/or wire bonding (connection between the Stentrode and the lead via an intermediate pad).

FIGS. 43A-43F illustrate various views of a variation of a portion of a connection panel 220. As shown, the connection panel 220 can have a first panel 222 (e.g., an overlay) attached to a portion of the stent 101, for example, a second panel 224. The second panel 224 can be a connection paddle. The second panel 224 can be integrated with or attached to the stent 101. The second panel 224 can have multiple pads (not shown) and multiple electrode tracks 236. The electrode tracks 236 can be electrically connected to the pads of the second panel 224. The first panel 222 can have multiple pads 226 and multiple openings 228 (also referred to as windows or holes). The pads can be made of platinum or other conductive materials. The openings 228 can be aligned with or otherwise placed over the pads on the stent 101. The first panel 222 can have the same number or a different number of pads 226 and openings 228. For example, the first panel 222 can have 16 pads 226 and 16 openings 228, although other numbers of pads and openings, more or less, are also appreciated (e.g., 1 to 32 or more pads and openings). As another example, the first panel 222 can have more pads 226 than openings 228. As yet another example, the first panel 222 can have fewer pads 226 than openings 228. The stent 101 can have the same number or a different number of pads as the number of openings 228 in the first panel 222. For example, the stent 101 can have 16 pads and the first panel 222 can have 16 openings 228. As another example, the stent 101 can have 16 pads and the first panel 222 can have fewer than 16 openings 228 (e.g., 4 or 8 openings).

Figure 43A:
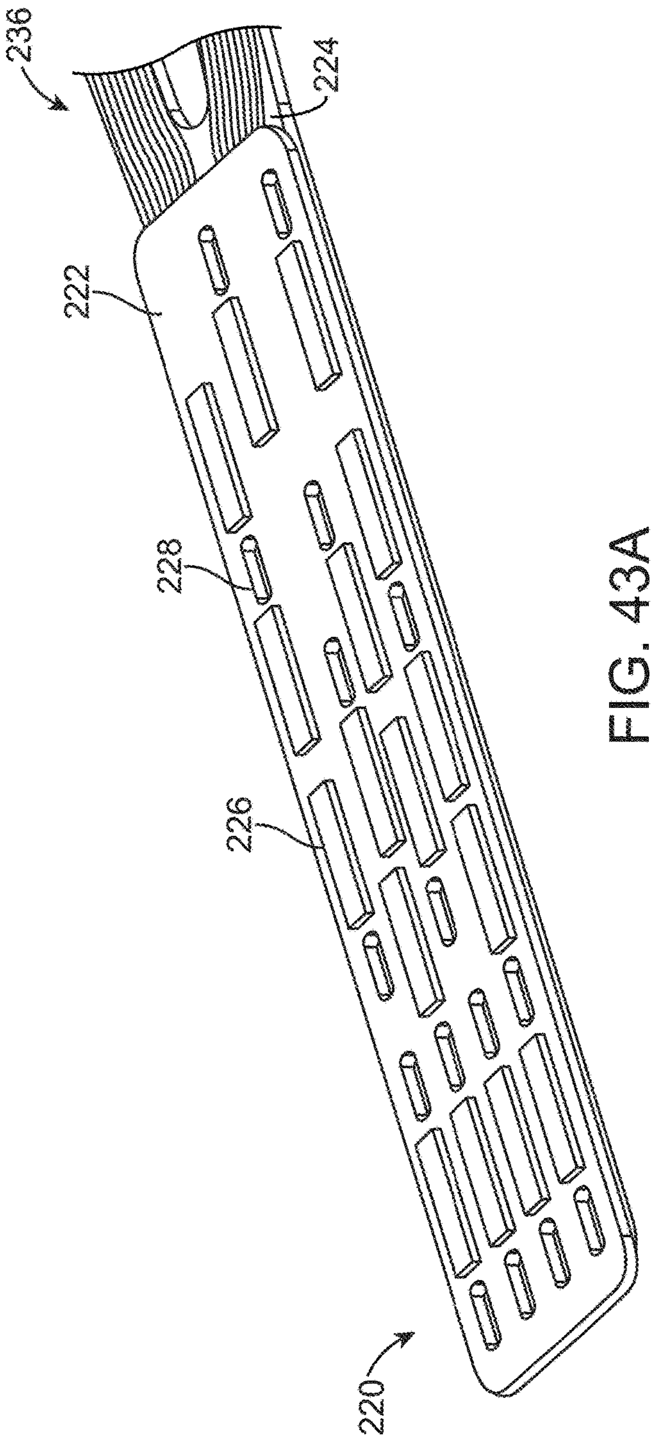
FIGS. 43A-43G illustrate various views of a variation of a connection panel.
Figure 43B:
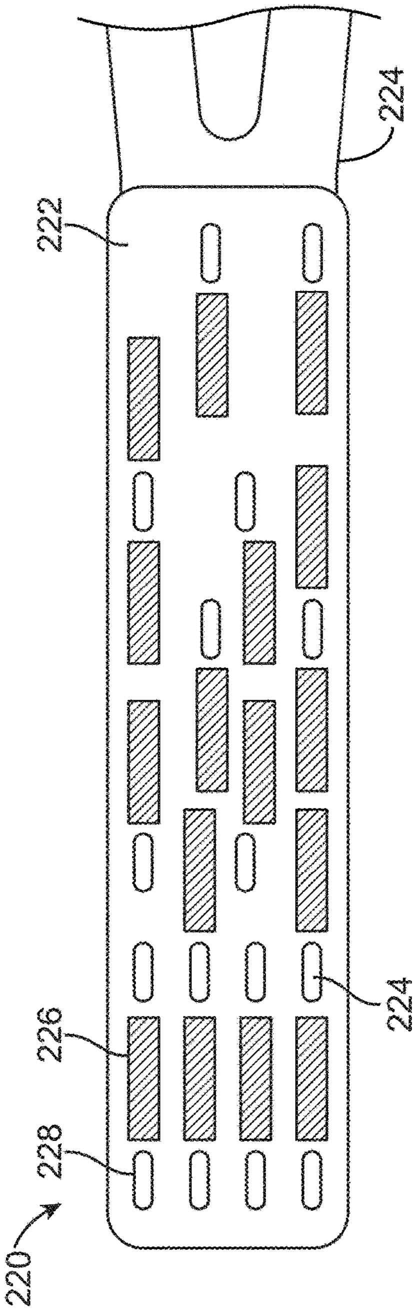

FIGS. 43A and 43B illustrate that the windows 228 can have a reduced cross-sectional area relative to the cross-sectional area of the pads 226. This can advantageously increase/optimize the operating space on the first panel 222 for wire management. The pads and windows 226, 228 can be arranged in various patterns to increase/optimize the operating space on the first panel for wire management. The pattern shown in FIGS. 43A and 43B is non-limiting, as any suitable pattern of pads and windows 226, 228 is appreciated. The pads and openings 226, 228 can have the various dimensions shown (in millimeters), for example, in FIG. 43G (on the same drawing sheet as FIGS. 43A and 43B).

Figure 43C:
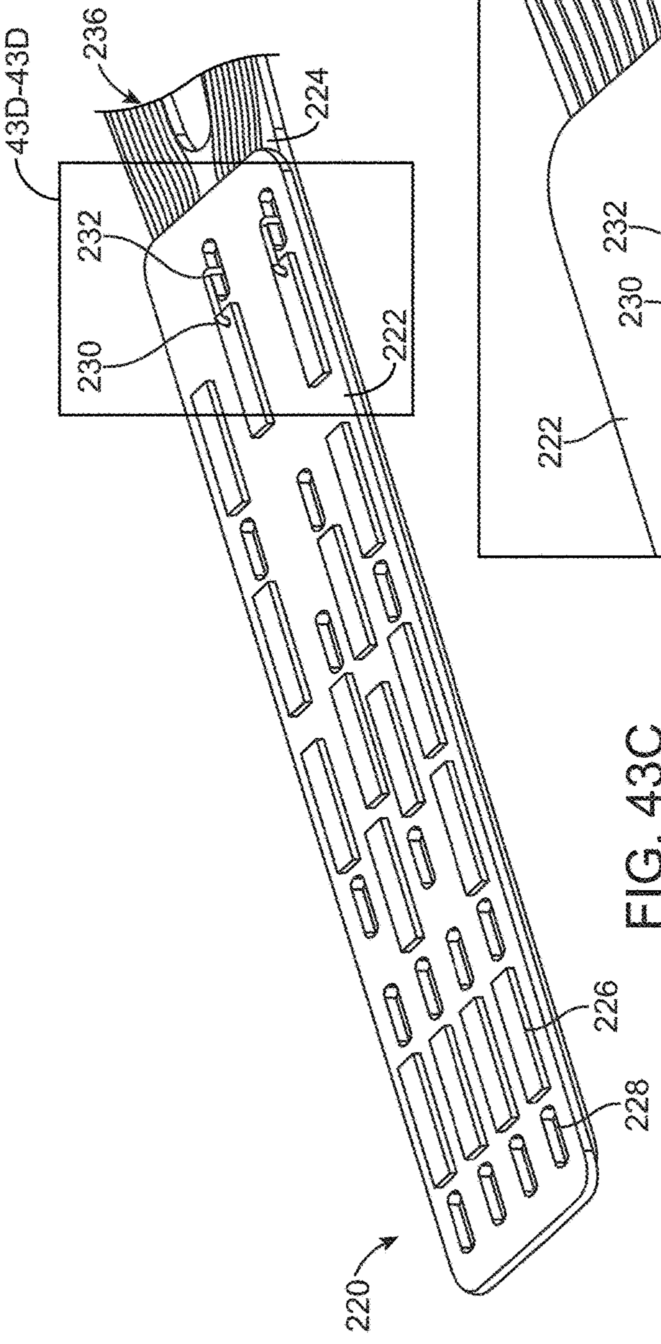
Figure 43D:
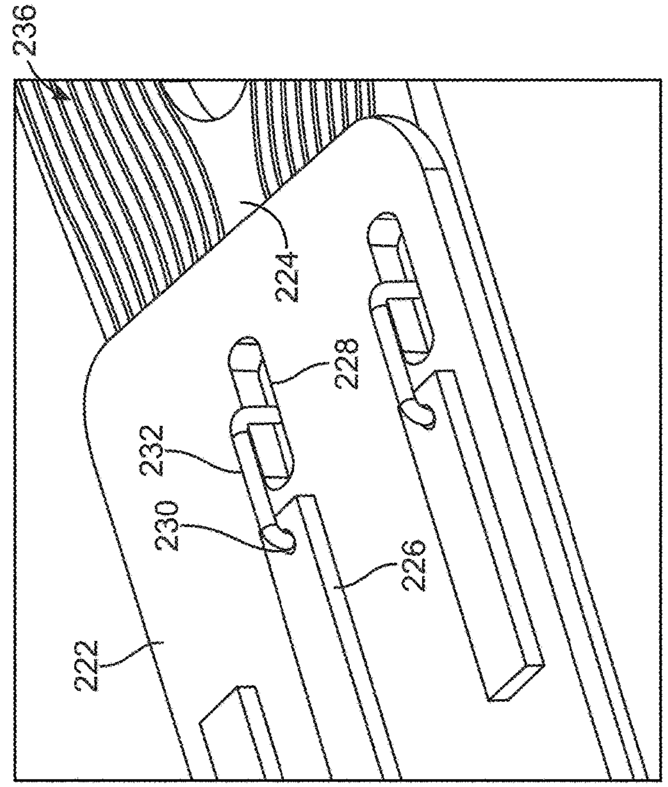

FIGS. 43C and 43D illustrate that wire bonds 230 can be made between the pads on the stent 101 and the pads 226 on the overlay 222. FIG. 43D is a magnified view of the wire bonds 230 of FIG. 43C at section 43D-43D. One or multiple wires 232 can pass through each of the windows 228. For example, two wires 232 are shown in FIGS. 43C and 43D passing through two different windows 228.

Figure 43E:
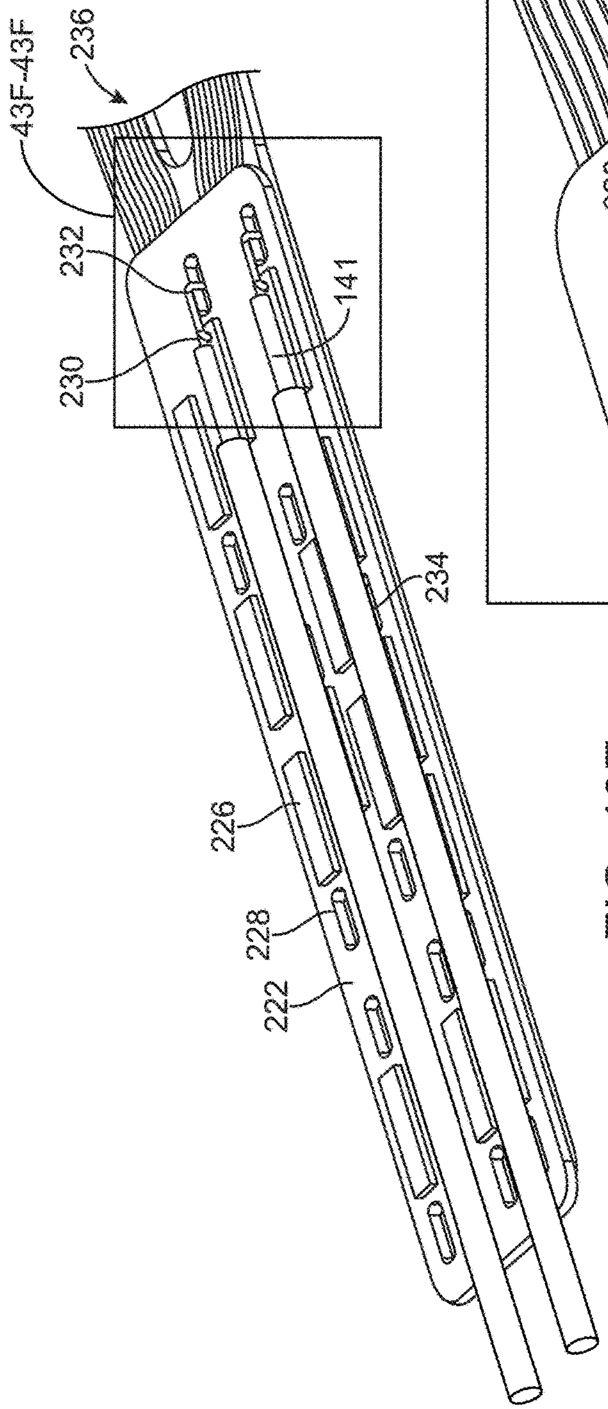
Figure 43F:
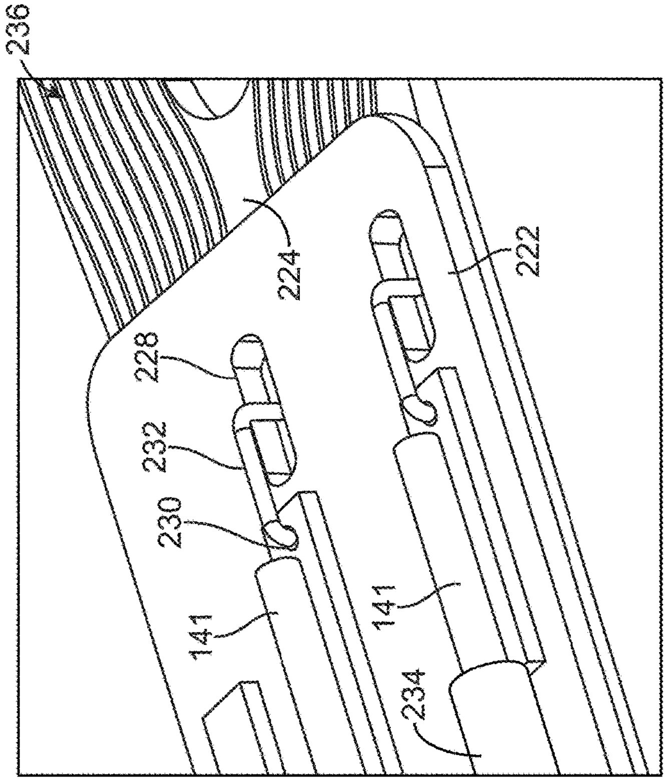
Figure 43G:
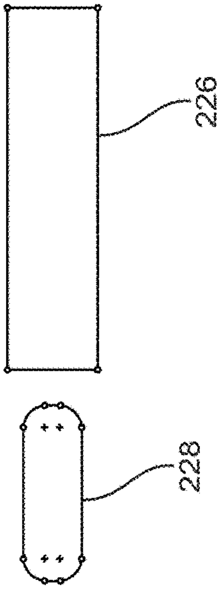

FIGS. 43E and 43F illustrate that the wires 141 can be attached (e.g., welded) to the pads 226 on the overlay 222. FIG. 43F is a magnified view of the wires 141 attached to the pads 226 of FIG. 43E at section 43E-43E. An insulating material 234 (e.g., epoxy) can cover at least a portion of the wires 141.

Figure 44A:
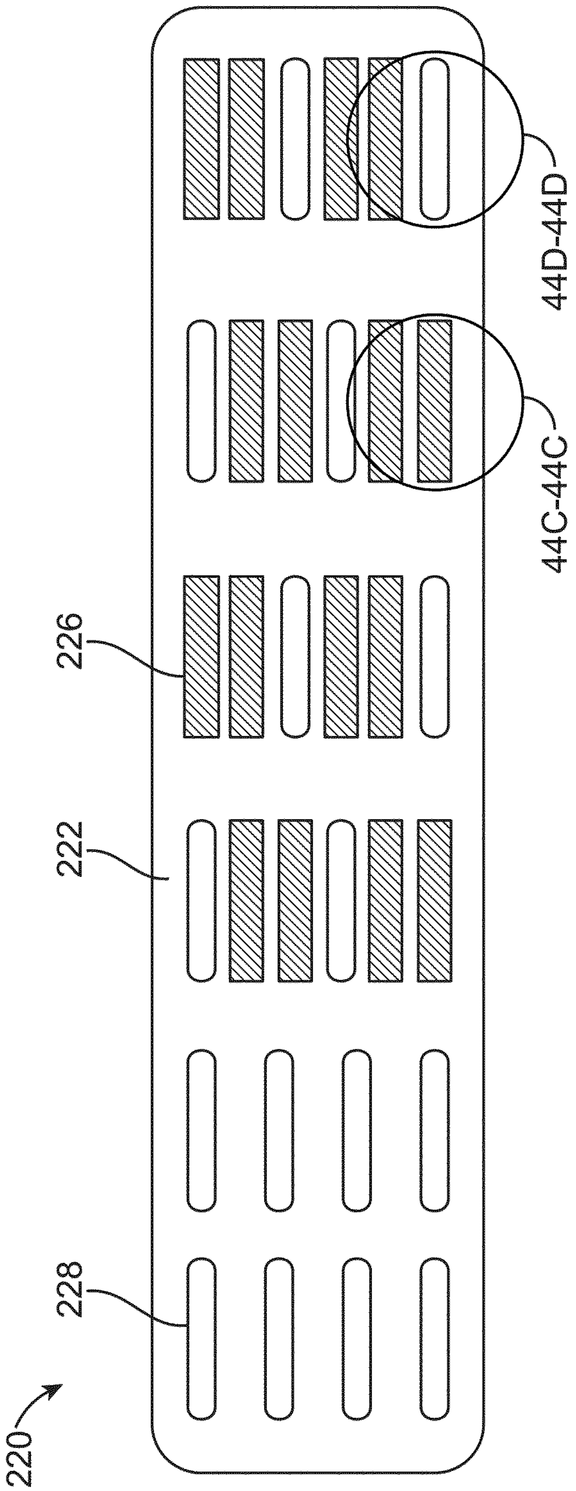
FIGS. 44A-44D illustrate a variation of an overlay.
Figure 44B:
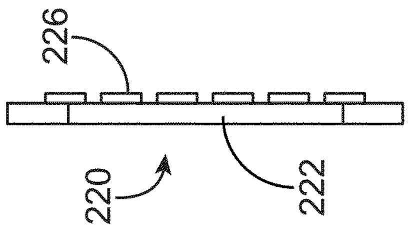
Figure 44C:
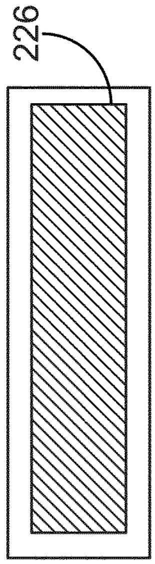
Figure 44D:
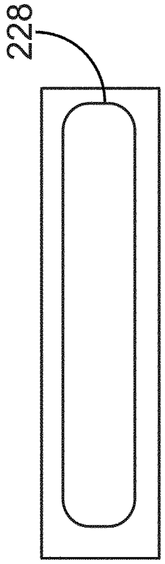

FIGS. 44A-44D illustrate a variation of an overlay 222 for wire bonding to a stent 101. The overlay 222 can have the various dimensions shown (in inches). The overlay 222 of FIGS. 44A-44D is similar to the overlay 222 of FIGS. 43A-43F except the pattern of the pads and openings 226, 228 is different, and the openings 228 are larger. FIG. 44C is a magnified view of one of the pads 226 of FIG. 44A at section 43C-43C. FIG. 44D is a magnified view of the opening 228 of FIG. 44A at section 44D-44D. The pads and openings 226, 228 can have the various dimensions shown (in inches). Wire bond pads can be placed in specific locations to enable all 16 electrode tracks to fit within the 900 μm width with enough separation that unwanted electrical connection is avoided. The overlay 222 can have a similar width to enable deployment through a 1 mm internal diameter catheter.

Figure 45A:
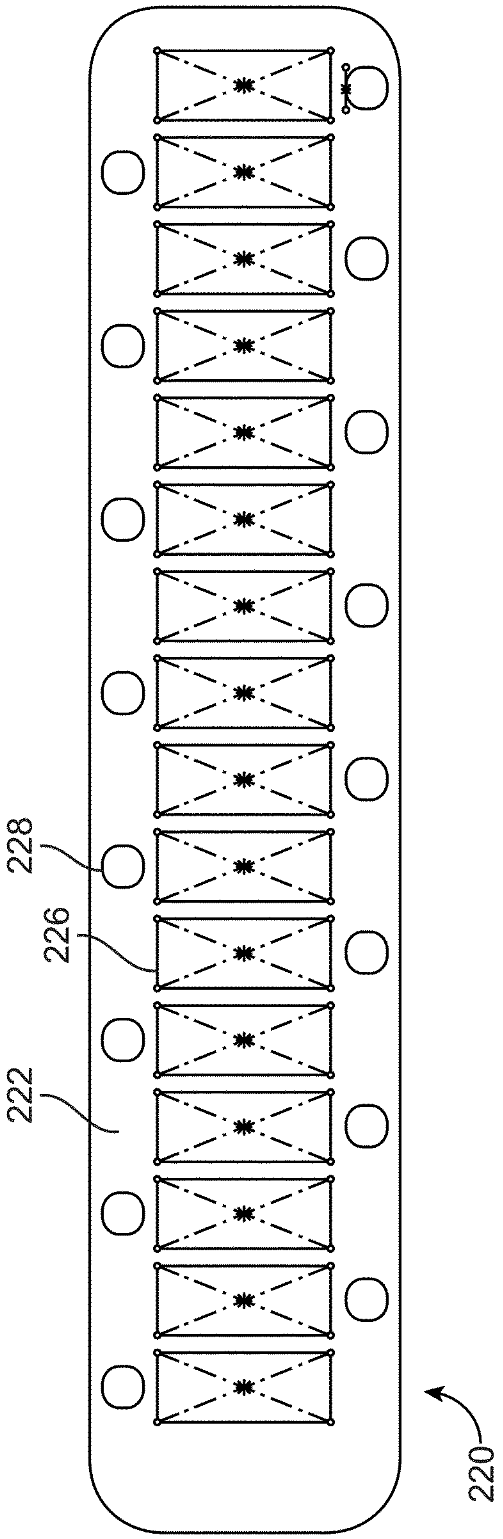
FIGS. 45A and 45B illustrate a variation of an overlay.
Figure 45B:
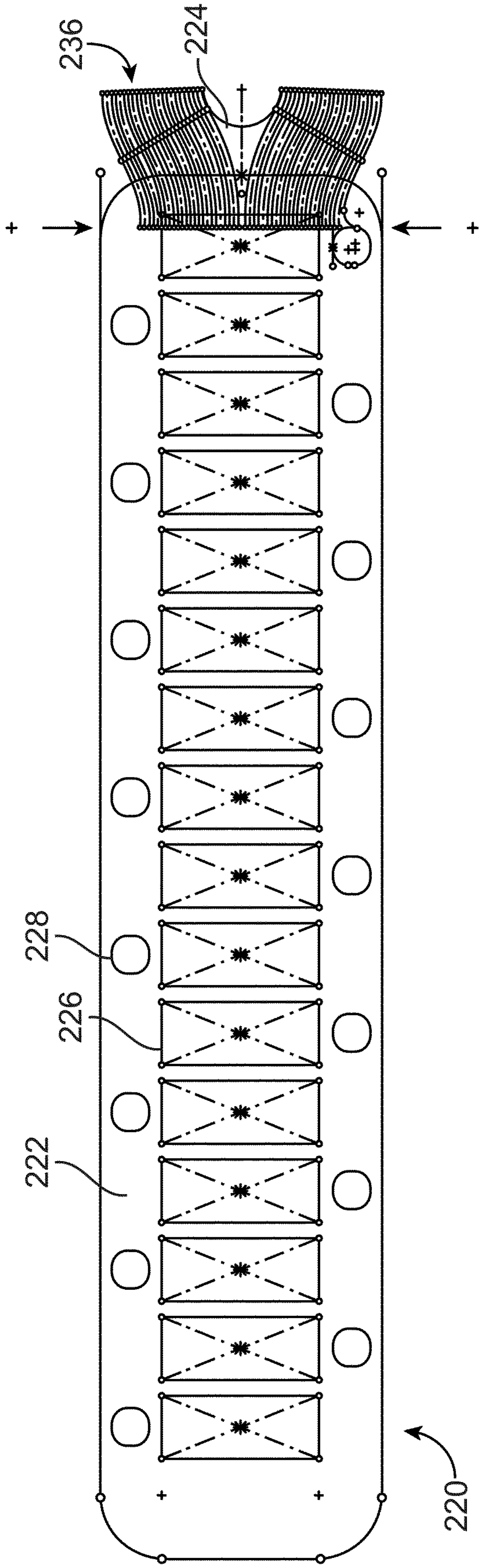

FIGS. 45A and 45D illustrate a variation of an overlay 222 for wire bonding to a stent 101. FIG. 45A illustrates a top view of the overlay 222 and FIG. 45B illustrates that the overlay 222 can be placed over the portion of the stent 101 having pads. The pads of the stent can be electrically connected to the electrodes 131 (not shown) via the electrode tracks 236. The pads and openings 226, 228 can have the various dimensions shown. This design, and similar changes to the pads on the stent 101, can advantageously allow for linear attachment of the pads 226 to the wire bonding holes 228, which can make manufacturing the connection panel 220 easier than, for example, the connection panel associated with FIGS. 44A-44D.

FIGS. 43A-45D illustrate that the wires 141 can be indirectly connected to the stent 101, for example, with wire bonding. The wires 141 can be indirectly connected to pads on the stent 101 via connection to intermediate pads 226 on the overlay 222. Such an intermediate connection method can advantageously allow for thicker/stronger wires 141 to be used to connect the lead 200 to the overlay 222. Welds from the overlay 222 to the stent 101 can overcome limitations on the stent 101 of having a small amount of platinum to weld to. This is advantageous relative to, for example, laser welding because laser welding typically requires more material which is melted to form a pool during welding. With a small amount of material, the melted pool can cause the track material to be sucked up into the pool, causing the tracks to break during manufacture.

FIGS. 46A-46F illustrate variations of stents 101 having various electrode 131 configurations. Each of these stents 101 can advantageously position electrodes 131 in a manner that, regardless of the manner in which the stent 101 is delivered into a vessel, there will always be sufficient electrodes 131 pointing to an information rich area of the brain (e.g., motor cortex, sensory cortex, among others) upon expansion from a compressed configuration. For purposes of illustration, the stents 101 are shown without any connecting structure that electrically couples the electrodes 131 to leads or other such structure that allows electrical communication between the electrodes 131 and the control unit 12 as described above.

As shown, the electrodes 131 can be dispersed about the body of the stents 101 at various locations. FIGS. 46A-46F illustrate that the stents 101 can have one or more cell sizes and/or shapes (e.g., diamond-shaped, V-shaped, among others). For example, the stents 101 can have cells that are longer than they are wide (L>W). This can advantageously allow for greater compression and reduce the force required to retract the stents 101 into a delivery instrument (e.g., a stylet or delivery catheter) and reduce the force required to deploy the stents 101 from within the delivery instrument. The stents 101 can have one or more cells that are wider than they are long (W>L). The stents 101 can have some cells that are longer than they are wide (L>W) and some cells that are wider than they are long (W>L). Such cell variations can advantageously accommodate various vessel physiologies.

One or more of the electrodes 131 can be attached to, embedded into, and/or otherwise integrated with the stents 101 as described above. For example, the stents 101 can have one or more integrated conductive layers (also referred to as electrode tracks and electrical tracks). The electrode tracks can have a thickness from about 200 μm to about 1000 μm. Other track thicknesses, more or less, as well as other ranges, narrower or wider, are also appreciated. Electrode tracks with these thicknesses can advantageously decrease the electrical resistance of the electrode track and provide more material (at the connection end) for welding. In FIGS. 46A-46F, the electrode track thickness is the dimension into the page (i.e., not width or length, which can remain constant to reduce the overall thickness of the Stentrode struts where multiple tracks are present, such as the fork 302 on the far left of the figures). The thickness of the struts 108 (i.e., the material underneath the insulation layers and electrical tracks) can be from about 50 μm to about 100 μm, for example, 50 μm, 85 μm, or 100 μm. Other strut thicknesses, more or less, as well as other ranges, narrower or wider, are also appreciated. The strut 108 thickness can increase or decrease gradually and/or in a step-wise manner along the stent 101 (e.g., gradually increase from 50 μm to 85 μm or step up from 50 μm to 85 μm). Thicker struts can have a larger radial and axial force relative to thinner struts. The thicker struts can therefore advantageously increase the apposition between the stent 101 and a vessel wall. The thicker struts can therefore increase the ability of the stent 101 to be pushed forward and deployed from within a delivery instrument (e.g., a catheter). The stents 101 can be thickest near the forks 302 on the proximal end of the stents 101 and can be thinnest at the distal end of the stents 101. The stents 101 can become thinner from the proximal end to the distal end. The stents 101 can have any suitable thickness(es), including a constant thickness.

The configurations of struts 108 and cells shown in FIGS. 46A-46F can enhance the apposition between the electrodes 131 and tissue or vessel walls when the stents 108 are in their expanded configuration. The strut and electrode configurations 108, 131 can advantageously allow the stents 101 to be compressed into a catheter. The strut and electrode configurations 108, 131 can advantageously allow the stents 101 to be expanded after being compressed in a catheter. The cells (e.g., their size and/or shape) and the electrode 131 positions can allow the stents 101 to compress and/or expand so that the struts and electrodes 108, 131 do not physically interfere with the compression and/or expansion of the stents 101. For example, the relative positions of the cells and the electrodes 131 can allow the stents 101 to compress and/or expand without getting stuck in a partially compressed configuration or a partially expanded configuration. The cells and the electrode 131 positions can help prevent electrodes and struts 131, 108 from becoming snagged with one another during compression or expansion of the stents 101. The relative positions of the cells and electrodes 131 can facilitate expansion and/or compression of the stents 101. The struts can be curved and/or straight. The struts that define the cells can be curved and/or straight.

To reduce the number of leads/wires from the stent 101 to external equipment, a multiplexing unit (not shown) can be used. The multiplexing unit can be placed on the connection panel/paddle of the stent 101 (e.g., second panel 224). The multiplexing unit can be placed on the stent 101, for example, on a strut 108. One or multiple multiplexors can be used. The multiplexing unit can be small enough so that it does not impede the radial force and flexibility of the stent 101. Multiplexing can reduce the number of wires required. One or more wires can be used with a multiplexor to power and switch between the electrodes 131 as required. The stent 101 can be wirelessly powered.

FIGS. 46A-58D illustrate various arrangements of stent cells, but any open cell configuration is appreciated. Moreover, although not shown, one or more of the stent cells can be closed such that there is not an opening in the cell. For purposes of illustration, the stents 101 shown in FIGS. 46A-58D are illustrated as having various lengths and various numbers of electrodes 131. However, other lengths, greater or smaller, as well as other numbers of electrodes, more or less, are also appreciated. The stent lengths shown in FIGS. 46A-58D is not limiting. The length of the stents 101 can be increased, for example, by including more stent in the longitudinal direction. For example, the length of the stents 101 can be increased by increasing the number of cells and/or by increasing the length and/or width of the cells. Similarly, length of the stents 101 can be decreased, for example, by having less stent in the longitudinal direction. For example, the length of the stents 101 can be decreased by decreasing the number of cells and/or by decreasing the length and/or width of the cells. The open cell designs in FIGS. 46A-58D are for illustrative purposes only as well. The cell arrangements shown can be repeated, changed, and/or altered to achieve the desired length of the stents 101 and/or the desired open cell design. FIGS. 46A-58D illustrate various cell shapes and sizes, but any open cell configuration for the stents 101 is appreciated. For example, any of the cells in FIGS. 46A-58D can be combined with one another to form a stent (e.g., stent 101). The numbers of electrodes in FIGS. 46A-58D can be increased or decreased as needed. For example, the stents 101 in FIGS. 46A-58D can have between 1 and 32 or more electrodes 131 (the numbers of electrodes 131 in the figures are exemplary only). In this way, the stents 101 can advantageously accommodate various vessel physiologies and sense and/or stimulate various tissues in one or multiple locations.

The stents 101 can have one or more sections of electrodes 131. The one or more sections can be separated by one or more sections of struts 108 that do or do not have electrodes.

As described above, the stents 101 disclosed and contemplated herein, for example, the stents 101 shown in FIGS. 46A-56D, can stimulate and/or sense various activity of media (e.g., tissue and/or fluids). For example, the stents 101 can stimulate and/or sense activity of fluid inside a lumen of a vessel, activity of a vessel itself, and/or activity of media (e.g., tissue and/or fluids) outside of the vessel such as the motor and/or sensory cortex of the brain.

Figure 46A:
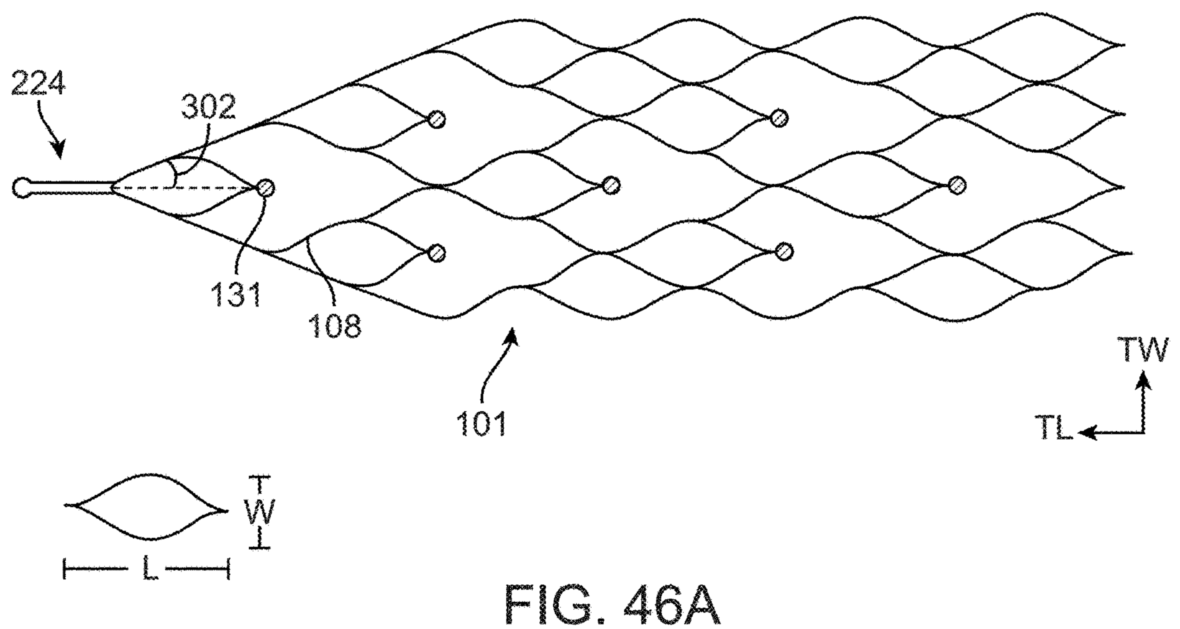
FIGS. 46A-46F illustrate variations of stents having various electrode configurations.

FIG. 46A illustrates that the stent 101 can have seven electrodes 131 arranged as shown. Other numbers of electrodes, more or less, are also appreciated (e.g., between 1 and 32 or more electrodes). The seven electrodes 131 can span radially across a length of the vessel with no electrode overlap. For example, the seven electrodes 131 can span radially across a length of an 8 mm vessel with no electrode overlap. The seven electrodes 131 can be at different radial positions along a length of the stent 101 such that there is no overlap of electrodes 131 when the stent 101 is expanded in a vessel. The seven electrodes 131 can be at different circumferential positions along the length of the stent 101 such that there is no overlap of electrodes 131 when the stent 101 is expanded in a vessel. As described above, this can advantageously ensure that the stent 101 has a sufficient number of electrodes 131 pointing to information rich areas of the brain (e.g., the motor cortex, the sensory cortex, among other areas) upon expansion from a compressed configuration.

FIG. 46A illustrates that the stent 101 can have large cells and small cells. The small cells can be inside the large cells. The struts 108 can define the cells. Some of the struts 108 can define at least a portion of a small cell and at least a portion of a large cell. Some of the struts 108 can define at least a portion of a small cell or at least a portion of a large cell. The electrodes 131 can be located on the small cells and/or the large cells. For example, the electrodes 131 can be integrated with the small cells. The electrodes 131 can be located anywhere on the small cells. For example, the electrodes 131 can be located at an apex of the small cells. The electrodes 131 can be located anywhere on the struts 108. As shown, the electrodes 131 can be located at the distal longitudinal apexes of the small cells. Although not shown, the electrodes 131 can be located on a portion of the small cells away from the distal longitudinal apexes, including for example, the transverse and proximal apexes. The electrodes 131 can be indirectly coupled to the large cells. The small cells can be inside the large cells for advantageous electrode placement and to assist with electrode-vessel wall apposition. The stent 101 can have a full set of small closed cells on top for stent overlap (e.g., the top row of small closed cells in FIG. 46A). The small cells can have a cell length L and a cell width W. The stent 101 can have a total length TL and a total width TW. The configuration in FIG. 46A can enhance the apposition between the electrodes 131 and the tissue of a vessel wall.

Figure 46B:
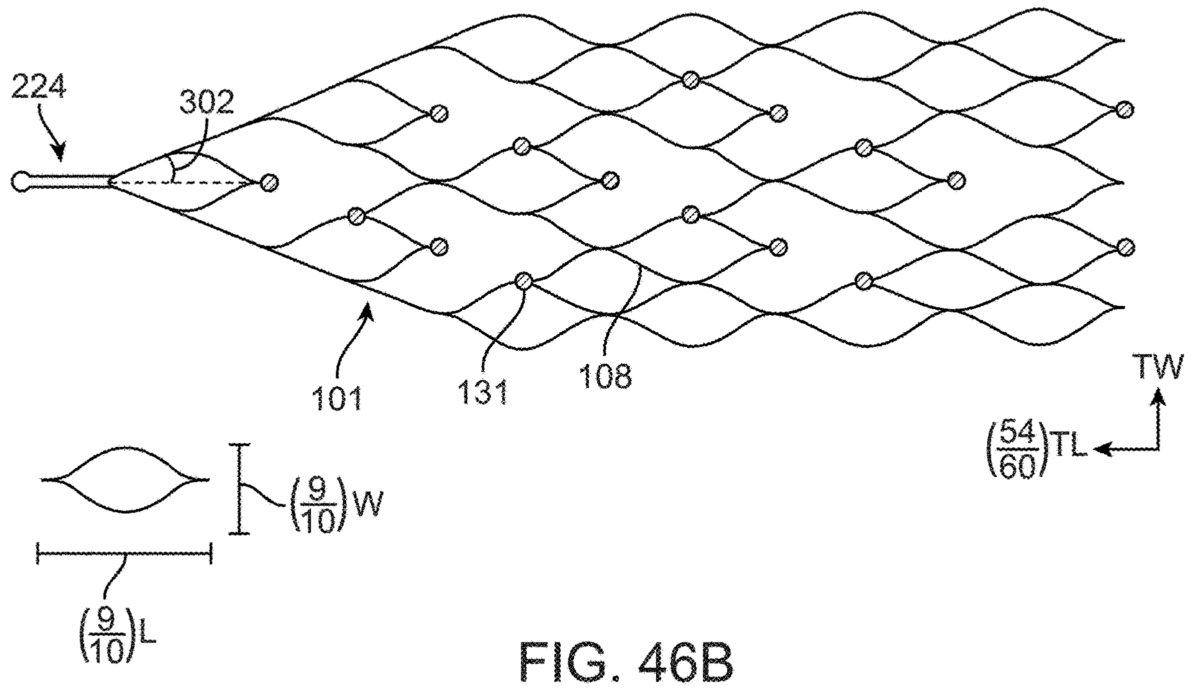

FIG. 46B illustrates that the stent 101 can have sixteen electrodes 131 arranged as shown. Other numbers of electrodes, more or less, are also appreciated. The electrodes 131 can be positioned in bipolar pairs for neural recording and stimulation efficiency. The bipolar pair arrangement can advantageously enable direct stimulation or recording from one electrode to another (e.g., between any two electrodes 131). This can elicit a response or record a signal from a focal region of the brain in a region between the electrodes 131 that form the bipolar pair (as opposed to an electrode 131 and a distant ground, with the second or return electrode placed off the stent). The electrodes 131 can be independent from one another. The electrodes 131 can be used in pairs. The electrodes 131 can be used in multiple pairs, for example, by switching among the electrodes 131. The electrodes 131 can be used in pairs and can be independent from one another. The configuration in FIG. 46B can enhance the apposition between the electrodes 131 and the tissue of a vessel wall.

Figure 46C:
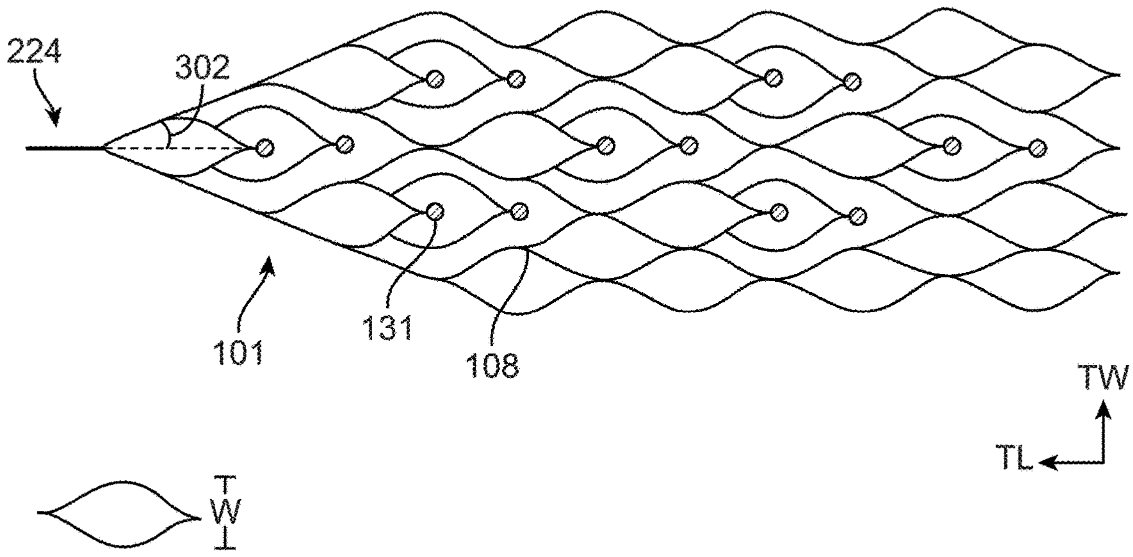

FIG. 46C illustrates that the stent 101 can have 14 electrodes 131 arranged as shown. Other numbers of electrodes, more or less, are also appreciated. The electrodes 131 can be positioned in bipolar pairs. The stent 101 of FIG. 46C is similar to the stent 101 of FIG. 46B, except that the bipolar electrode pairs are constructed with one electrode mounted to an open cell and another electrode mounted in an open cell style to that electrode to enhance electrode apposition while ensuring known distance between electrodes.

Figure 46D:
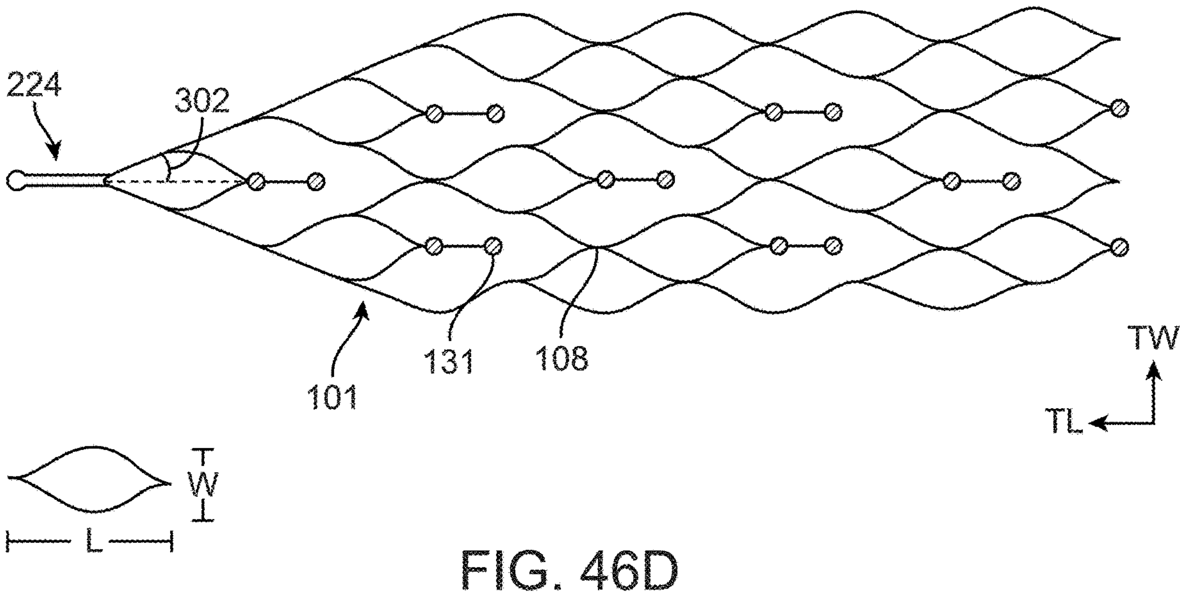

FIG. 46D illustrates that the stent 101 can have 16 electrodes 131 arranged as shown. Other numbers of electrodes, more or less, are also appreciated. The electrodes 131 can be positioned in bipolar pairs. FIG. 46D illustrates that the stent 101 can have a straight, single strut bipolar pair open cell design. The electrodes 131 can be mounted on the inside of open cell struts with a bipolar pair electrode 131 attached with single linear strut 108. This can reduce the amount of material required (compared, for example, to the amount of material required for the stent 101 illustrated in FIG. 46C). The configuration in FIG. 46D can enhance the apposition between the electrodes 131 and the tissue of a vessel wall.

Figure 46E:
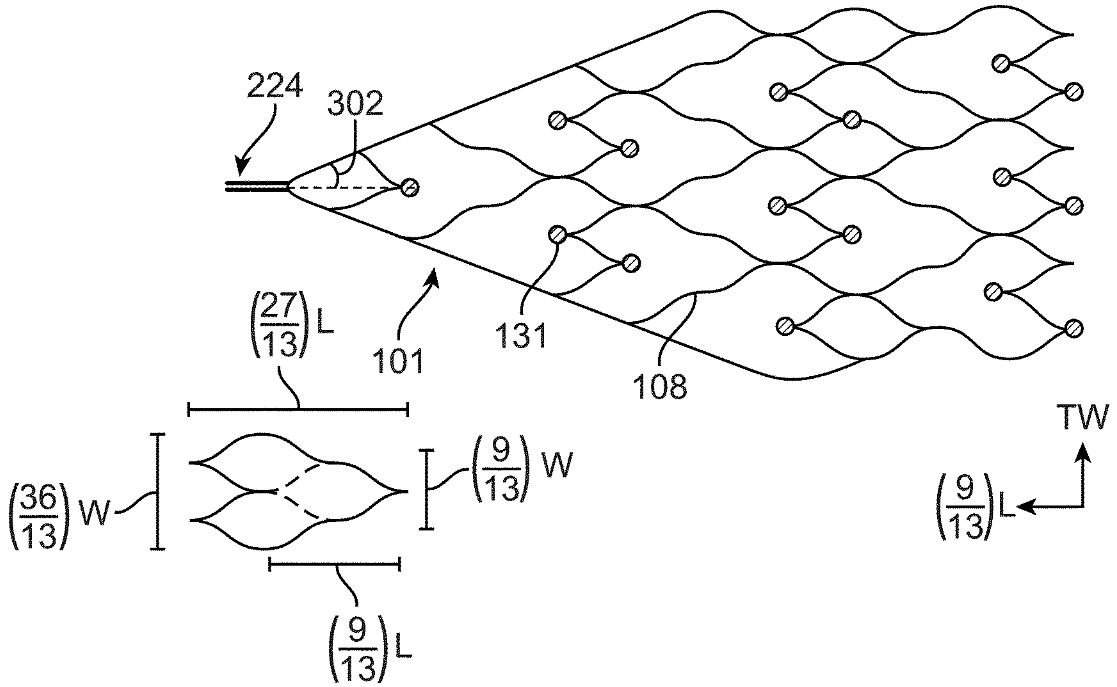

FIG. 46E illustrates that the stent 101 can have 16 electrodes 131 arranged as shown. Other numbers of electrodes, more or less, are also appreciated. The electrodes 131 can be positioned in bipolar pairs. The cells of the stent 101 can have the shapes shown. The electrodes can have the locations shown, although any location on struts 108 defining the cells is appreciated. The stent 101 can be flexible and require less material that the stents 101 illustrated in FIGS. 46A-46D. The configuration in FIG. 46E can enhance the apposition between the electrodes 131 and the tissue of a vessel wall. For example, the configuration in FIG. 46E can appose the vessel wall around vascular chordae which maintaining superelasticity, at least partly to the large open cell design.

Figure 46F:
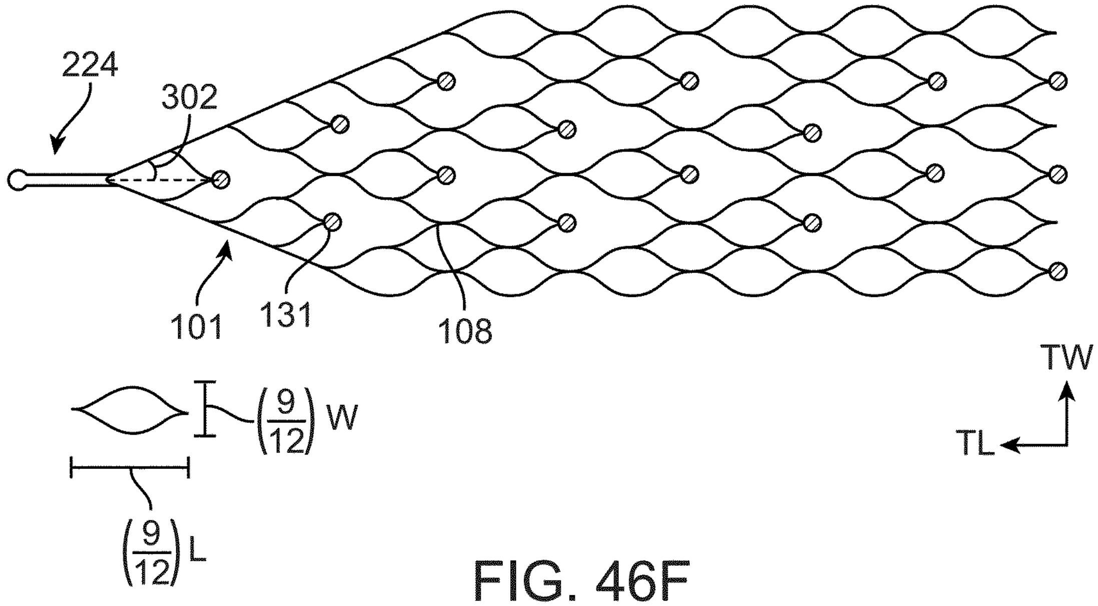

FIG. 46F illustrates that the stent 101 can have sixteen electrodes 131 arranged as shown. Other numbers of electrodes, more or less, are also appreciated. The stent 101 of FIG. 46F is similar to the stent 101 of FIG. 46A except that the stent 101 of FIG. 46F can have a greater length and is illustrated with more electrodes 131.

FIGS. 47A-47F illustrate variations of stents 101 having various electrode 131 configurations. The stents 101 of FIGS. 47A-47F are similar to the stents 101 of FIGS. 46A-46F except for the different cell configurations and electrode 131 locations. FIGS. 47A-47F illustrate that the stents 101 can have strut crosslinks 109 that are offset from one another, for example, by offset angles 304. The offset crosslinks 109 can advantageously allow the stents 101 to be compressed without having any stent overlap. This can, in turn, advantageously allow the stents 101 to be more easily expanded by preventing or otherwise reducing the risk of cells and/or electrodes 131 from becoming entangled or snagged with one another when the stents 101 are expanded. For purposes of illustration, the stents 101 in FIGS. 47A-47E have been illustrated with linearly arranged struts 108, forming various diamond- and rectilinear-shaped cells. However, the cells of the stents 101 can be shaped as shown in the lower left insets of FIGS. 47A-47F, which are similar to the small cells of FIGS. 46A-46F except for the offset angles 304 described above. The offset angle can be, for example, 101 degrees (e.g., 101.3 degrees), although other offset angles, more or less, are also appreciated (e.g., 80 degrees to 120 degrees, or narrower or wider ranges).

FIGS. 47A-47F illustrate that the length to width ratio of the cells can be 7:5. The 7:5 ratio helps ensure that the stents 101 can compress and expand.

Figure 47A:
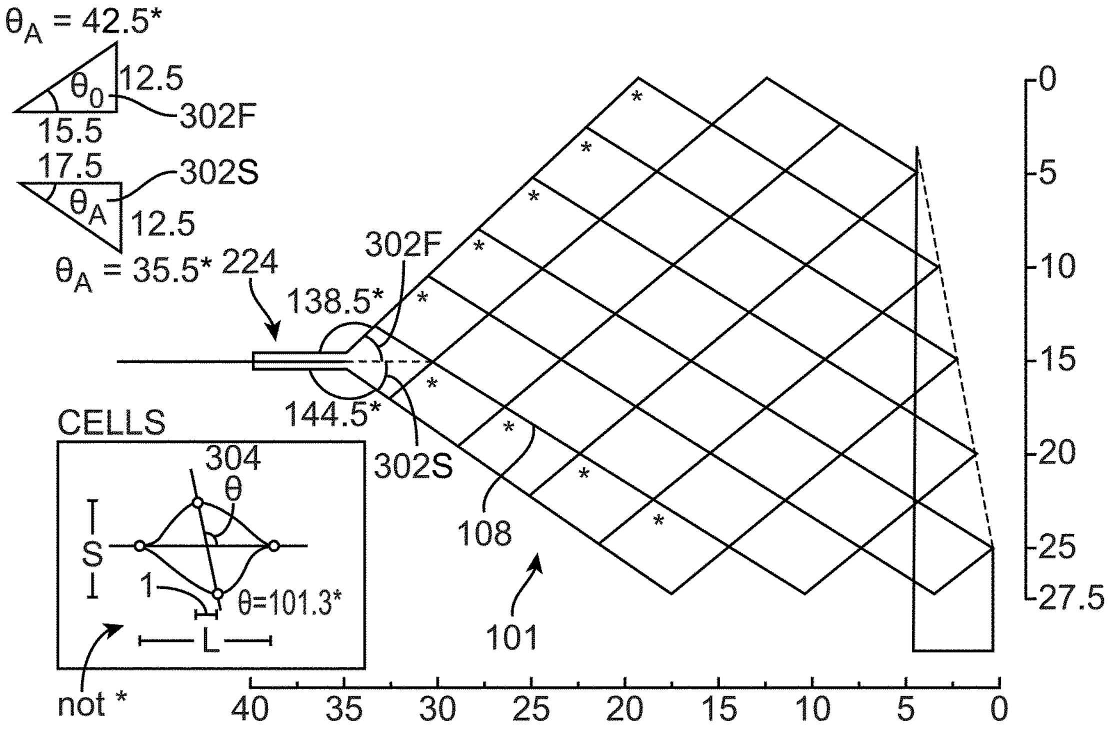
FIGS. 47A-47F illustrate variations of stents having various electrode configurations.

FIGS. 47A-47F illustrate that the stents 101 can have a fork angle 302. FIG. 47A shows that the stents 101 can have a first fork angle 302F and a second fork angle 302S. The first and second fork angles 302F, 302S can be the same or different from one another. As shown, the first and second fork angles 302F, 302F can be measured, for example, between a center axis and first and second struts (not separately labeled) that extend from the connection panel 224. The first and second fork angles 302F, 302S can each be from about 30 degrees to about 50 degrees. For example, the first fork angle 302F can be about 41.5 degrees and the second fork angle 302S can be about 35.5 degrees. Other fork angles, more or less, as well as other fork angle ranges, narrower or wider, are also appreciated. The fork angle 302 can advantageously allow for easier deployment (e.g., expansion) and retraction (e.g., compression) of the stents 101.

Figure 47B:
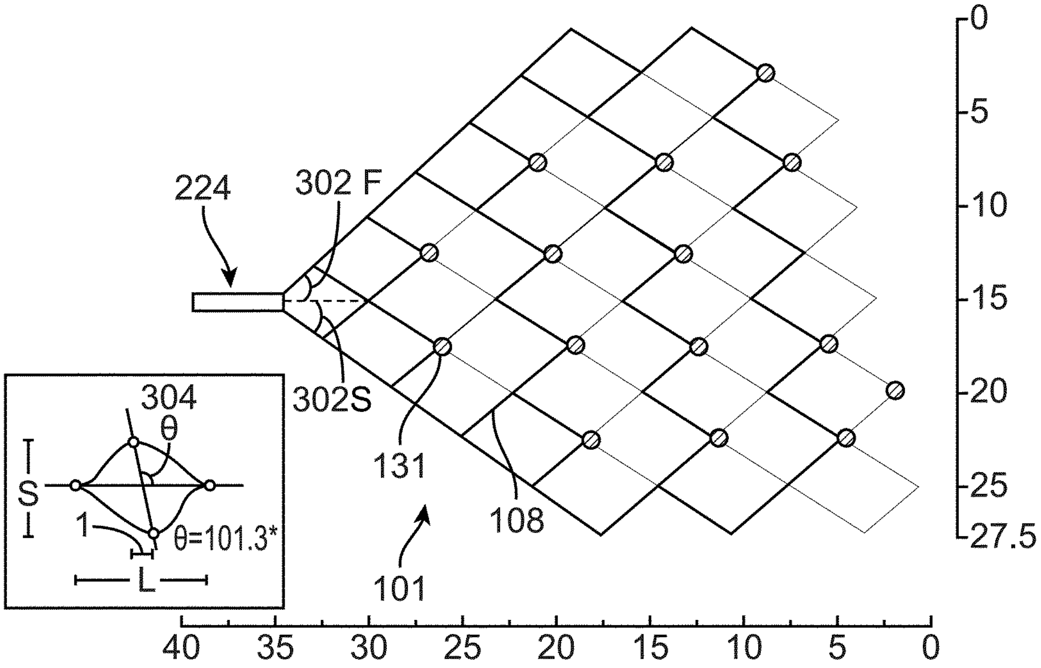
Figure 47C:
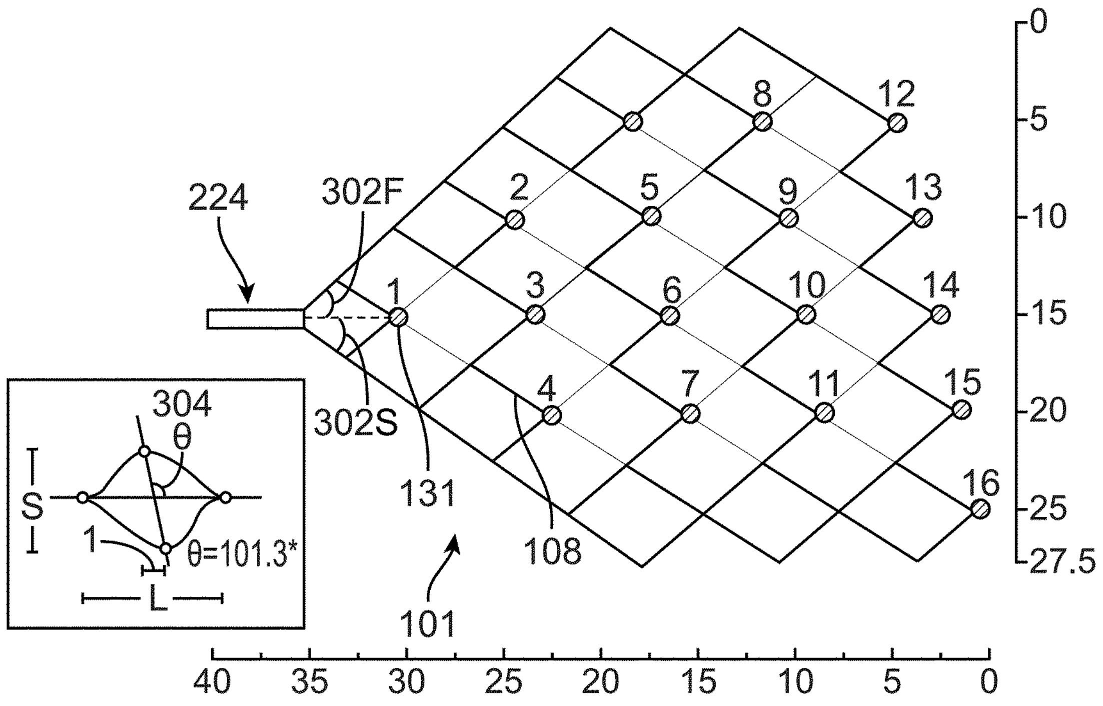

FIG. 47B illustrates that the stent 101 can have sixteen electrodes 131 arranged as shown. Other numbers of electrodes, more or less, are also appreciated. The sixteen electrodes can be arranged in a ladder style having two or more "rungs." For example, the sixteen electrodes can be arranged in five rungs of electrodes 131 having a 2-4-4-5-1 pattern. The stent 101 can have any number of rungs and any number of electrodes 131 in each of the rungs, including four rungs having a 2-4-5-5 electrode pattern. As another example, FIG. 47C illustrates that the stent 101 can have sixteen electrodes arranged in five ladder rungs having a 1-3-3-4-5 electrode pattern. The 1-3-3-4-5 pattern of FIG. 47C can advantageously provide additional electrical evaluation length (e.g., stimulation and/or recording length) relative to shorter ladder configurations, for example, the 2-4-5-5 pattern of FIG. 47B. The ladder style can advantageously assist with delivery through vascular tortuosity and enable navigation of vascular chordae whilst ensuring electrode apposition and self-expansion.

Figure 47D:
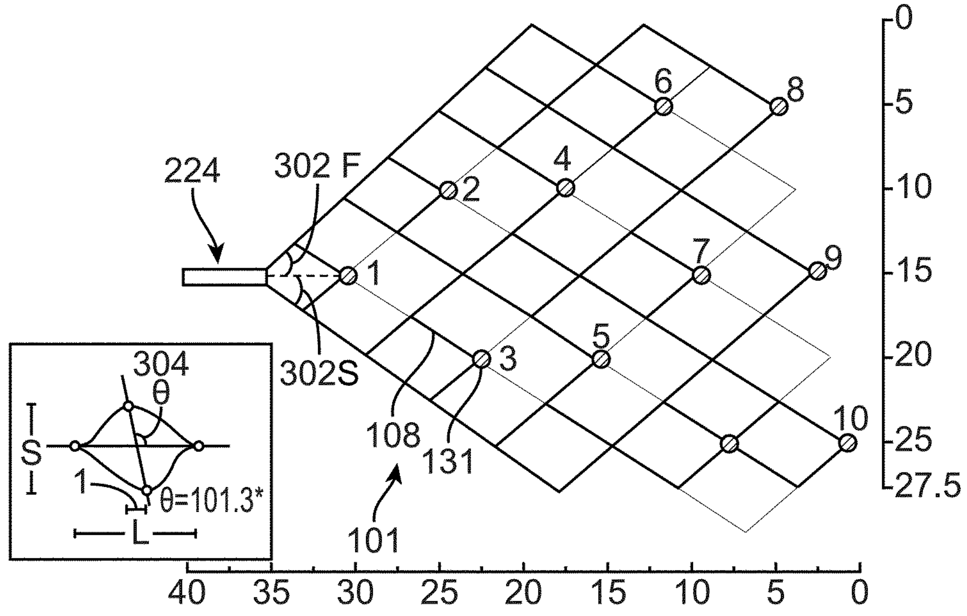

FIG. 47D illustrates that the stent 101 can have ten electrodes 131 arranged as shown. The ten electrodes 131 are shown in a 1-2-2-2-3 five rung ladder pattern, although any ladder pattern having ten electrodes is appreciated. The stent 101 can have relative cell sizes similar to the large and small cells described above with reference to FIG. 46A.

Figure 47E:
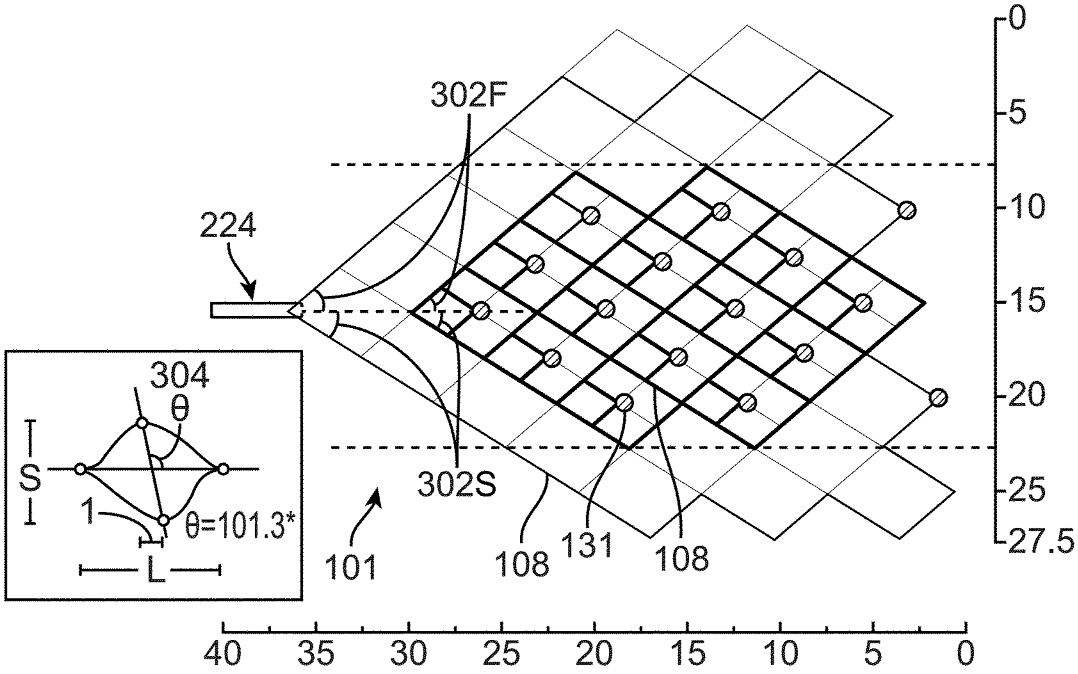

FIG. 47E illustrates that the stent 101 can have sixteen electrodes 131 arranged as shown. FIG. 47E illustrates that the stent 101 can have larger cells on the border (e.g., perimeter) of the stent 101 and more dense cells closer to the center (e.g., in the center) of the stent 101. This arrangement of cells and electrodes 131 can advantageously provide an enhanced region for recording or stimulation closer to the center of the stent 101. As shown, the electrodes 131 can be arranged in an eight rung 1-2-3-2-3-2-1-2 ladder pattern, although any ladder pattern having sixteen electrodes 131 is appreciated.

Figure 47F:
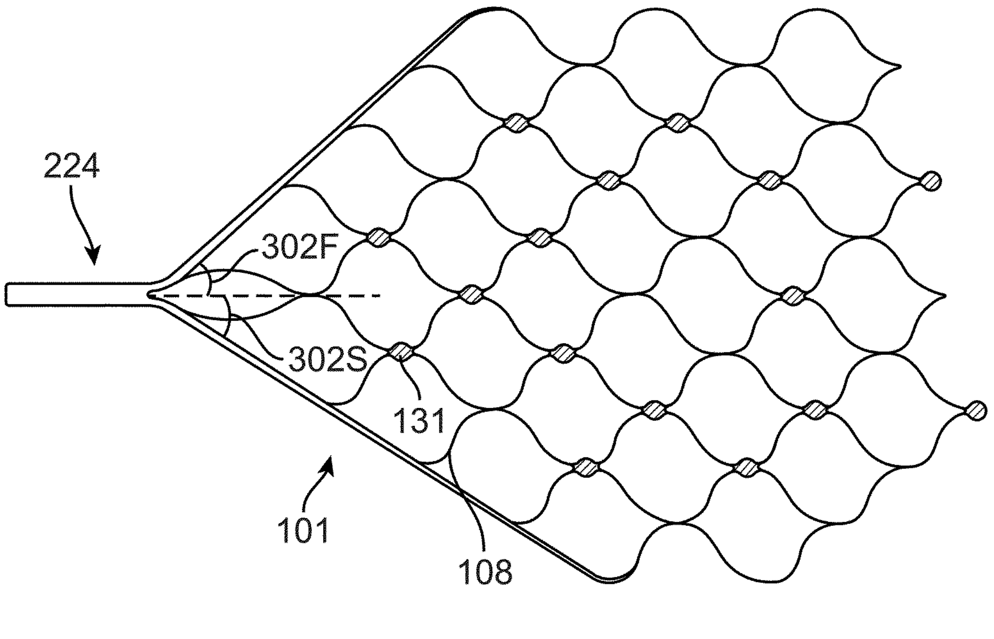

FIG. 47F illustrates that the stent 101 can have sixteen electrodes arranged in seven ladder rungs having a 2-1-4-2-2-3-2 electrode pattern. The 2-1-4-2-2-3-2 pattern of FIG. 47F can advantageously provide additional electrical evaluation length (e.g., stimulation and/or recording length) relative to shorter ladder configurations, for example, relative to the ladder patterns of FIG. 47B-47D. FIG. 47F illustrates fork angles 302F, 302S that assist with delivery, retraction and deployment, skewed electrode locations for improved deliverability and reducing overlap, interleaved cells for overlap and radial force, cell aspect ratio for deliverability and self-expansion.

For purposes of illustration, the stents 101 in FIGS. 46A-47F described above and FIGS. 48A-48B, 46B-46C, 51B, 52B, 53B-53C, 54A-57 and 58C described below are shown flat so that the cells, struts 108, electrodes 131, and/or electrode tracks 236 can be easily seen. However, the stents 101 are curved in practice (e.g., when in the compressed and/or expanded configuration). The top of the stents 101 can be directly joined to the bottom of the stents 101 (the top and bottom as shown in FIGS. 46A-47F) to form cylindrical tube-like stent structures that can exert radial outward forces against a vessel wall. The top of the stents 101 can curve around to meet (with or without permanent attachment) the bottom of the stents 101. A portion of the top and bottom of the stents 101 can overlap or there can be a gap therebetween.

Figure 48A:
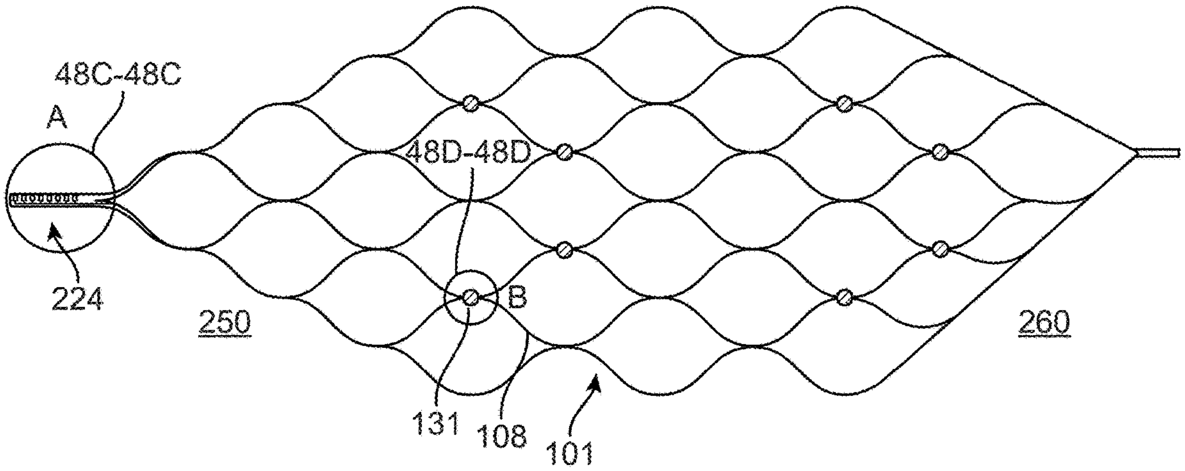
FIGS. 48A-48D illustrate a variation of a stent.
Figure 48B:
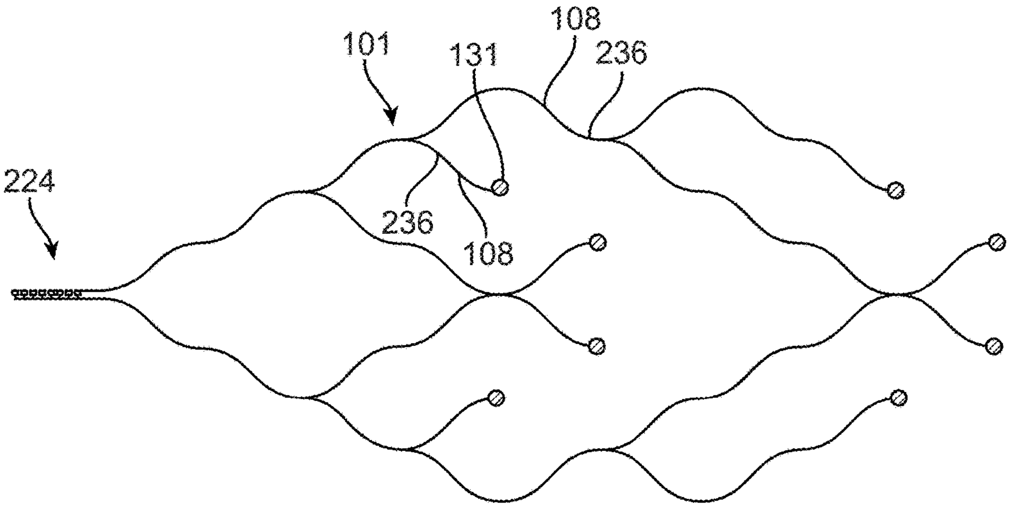
Figure 48C:
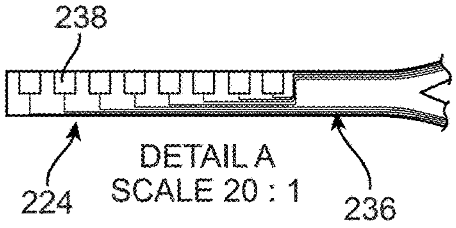
Figure 48D:
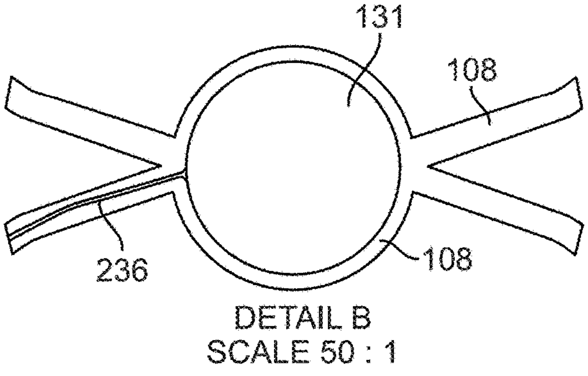

FIGS. 48A-48D illustrate a variation of a stent 101. FIG. 48A illustrates that the stent 101 can have eight electrodes 131 arranged as shown. The stent 101 can have a proximal end 250 and a distal end 260. The proximal end 250 can include a second panel 224 as described above. The second panel 224 can have stent pads 238. FIG. 48B illustrates the struts 108 of FIG. 48A that have electrode tracks 236. For purposes of illustration, the stent 101 is shown flat in FIGS. 48A and 48B but can be curved as described above. FIG. 48C is a magnified view of the proximal end 250 of the stent 101 of FIG. 48A at section 48C-48C and shows the electrode tracks 236 electrically connected to the stent pads 238. An overlay 222 can be placed over the stent pads 238. FIG. 48D is a magnified view of an electrode 131 of FIG. 48A at section 48D-48D.

Figure 49A:
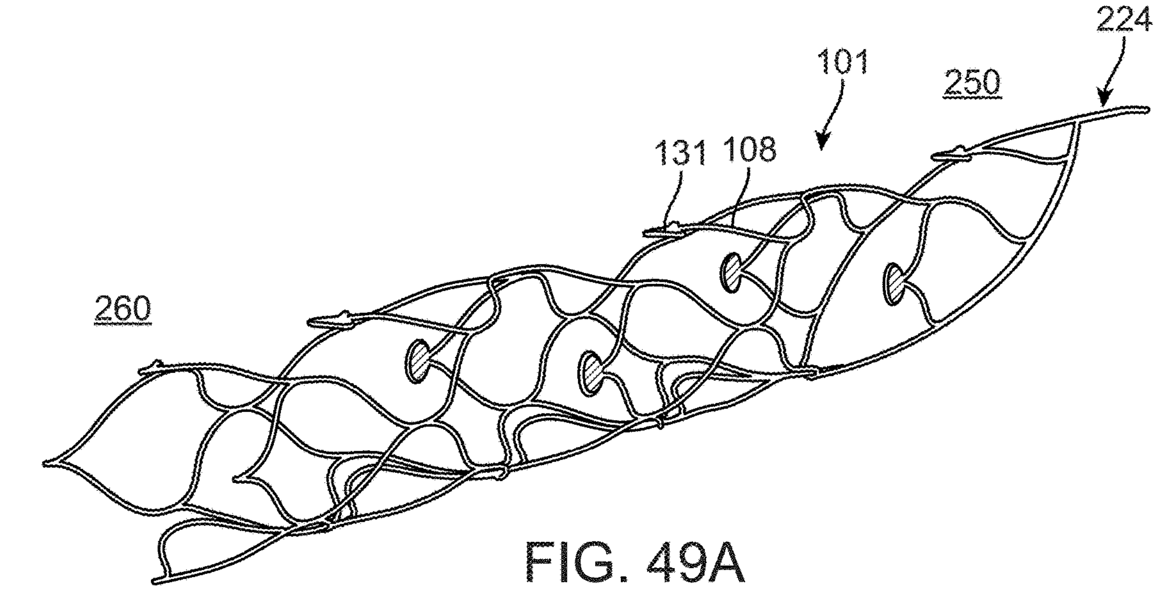
FIGS. 49A-49C illustrate a variation of a stent.
Figure 49B:
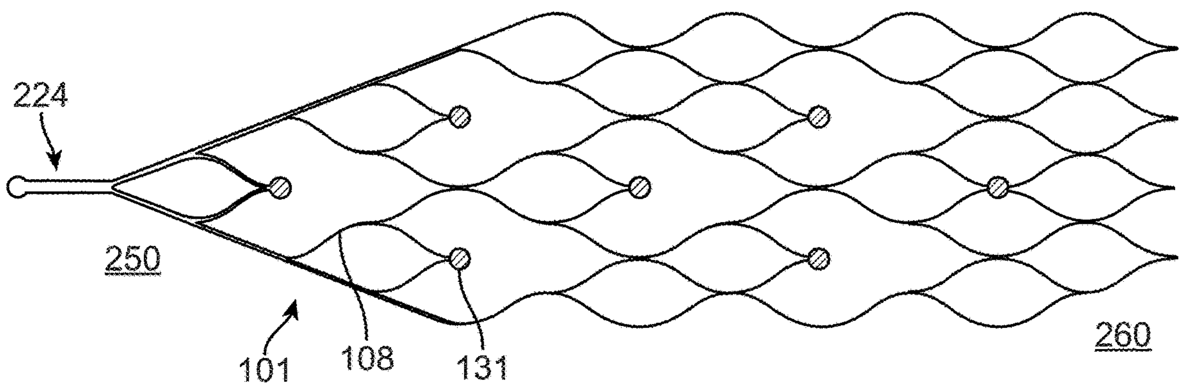
Figure 49C:
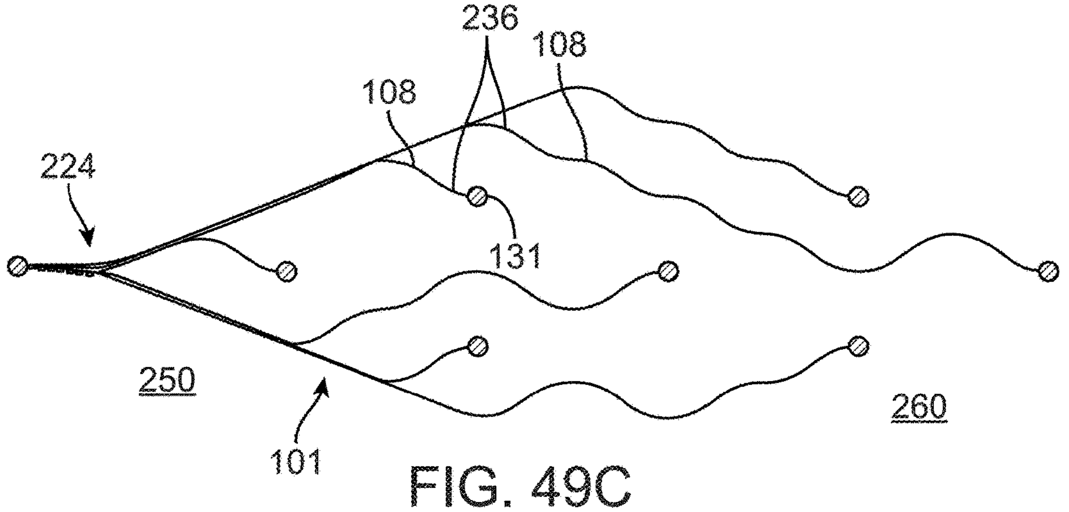

FIGS. 49A-49C illustrate a variation of a stent 101 having seven electrodes 131 arranged as shown. The stent 101 of FIGS. 49A-49C is similar to the stent 101 of FIG. 46A. FIG. 49A illustrates a perspective view of the stent 101 having a curved profile in an expanded configuration. FIG. 49B illustrates the stent 101 in a flat configuration. FIG. 49C illustrates the struts 108 of FIGS. 49A and 49B that have the electrode tracks 236. FIGS. 49B and 49C illustrate that the struts 108 can get thicker from the distal end 260 to the proximal end 250, for example, to accommodate multiple electrode tracks 236 as they merge into a common strut and/or to increase the axial and radial forces/resilience of the stent 101. Multiple electrode tracks 236 on a common strut can be parallel to each other.

Figure 50B:
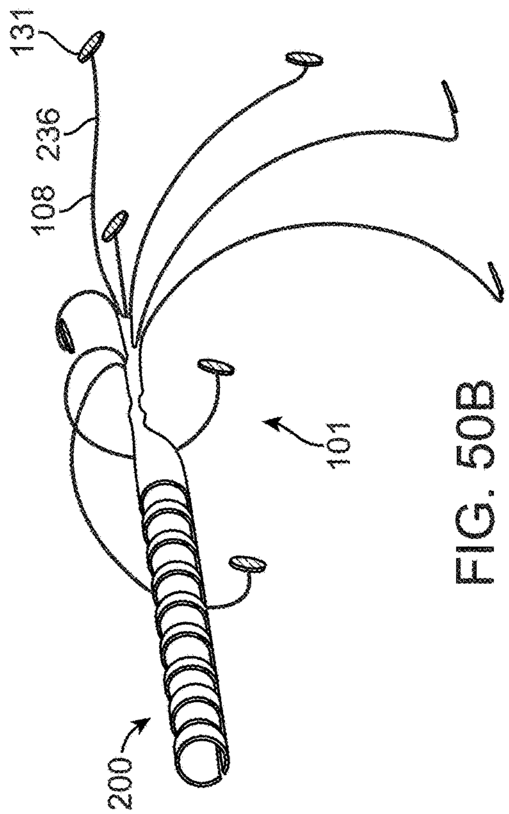
FIGS. 50A-50C illustrate a variation of a stent.
Figure 50A:
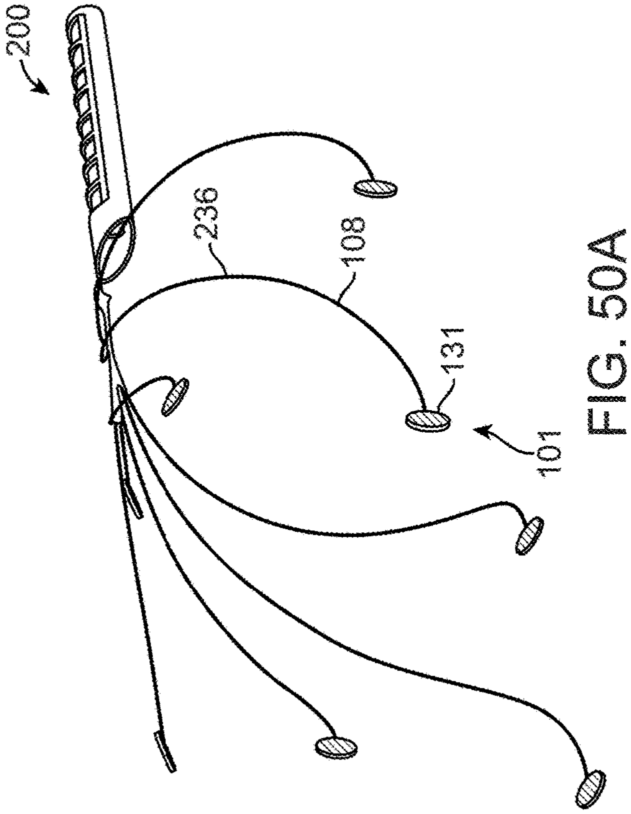
Figure 50C:
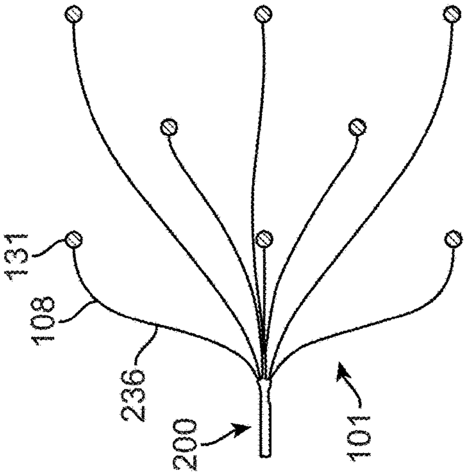

FIGS. 50A-50C illustrate front perspective, rear perspective and top views of a variation of a stent 101 connected to a connection panel 220. The stent 101 can have eight electrodes 131 arranged as shown.

Figure 51A:
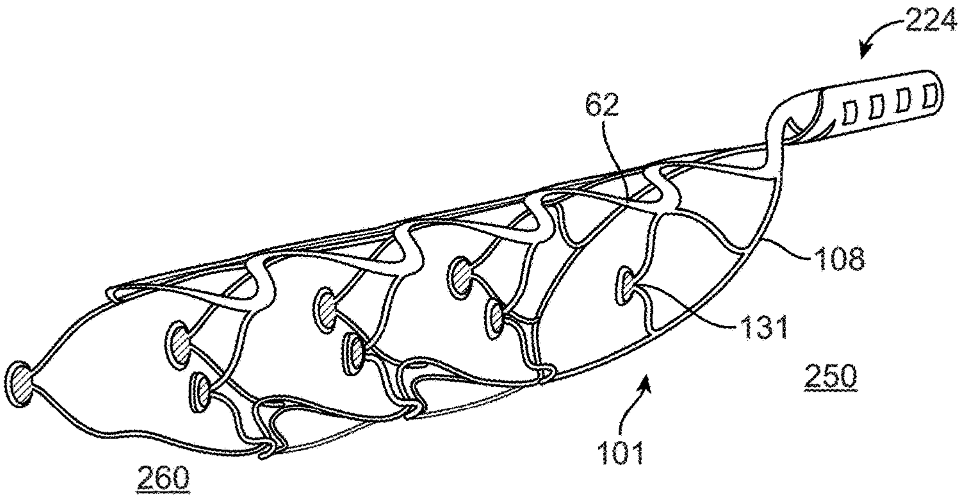
FIGS. 51A and 51B illustrate a variation of a stent.
Figure 51B:
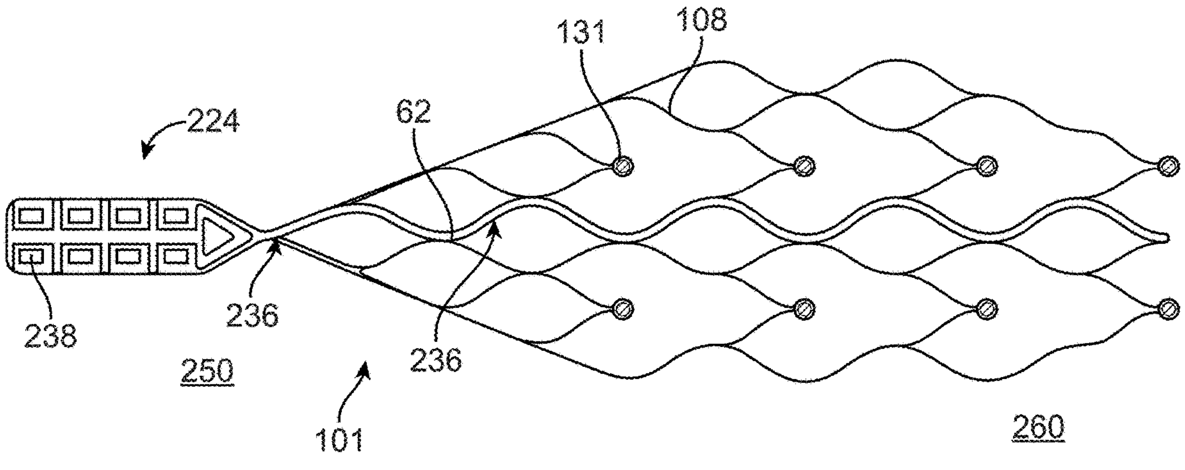

FIGS. 51A and 51B illustrate a variation of a stent 101 having eight electrodes 131 arranged as shown. FIG. 51A illustrates a perspective view of the stent 101 having a curved profile in an expanded configuration and FIG. 51B illustrates the stent 101 in a flat configuration. The stent 101 can have a reinforced section 62. As shown, the electrode tracks 236 from each of the electrodes 131 can merge into the reinforced section 62. The multiple electrode tracks 236 in the reinforced section 62 can be parallel to each other. Some of the struts 108 and/or the reinforced section 62 can get thicker from the distal end 260 to the proximal end 250. The stent pads 238 can be directly connected to the lead wires 141 of a connector 200 (not shown). The stent pads 238 can be indirectly connected to the lead wires 141 of a connector 200 (not shown).

Figure 52A:
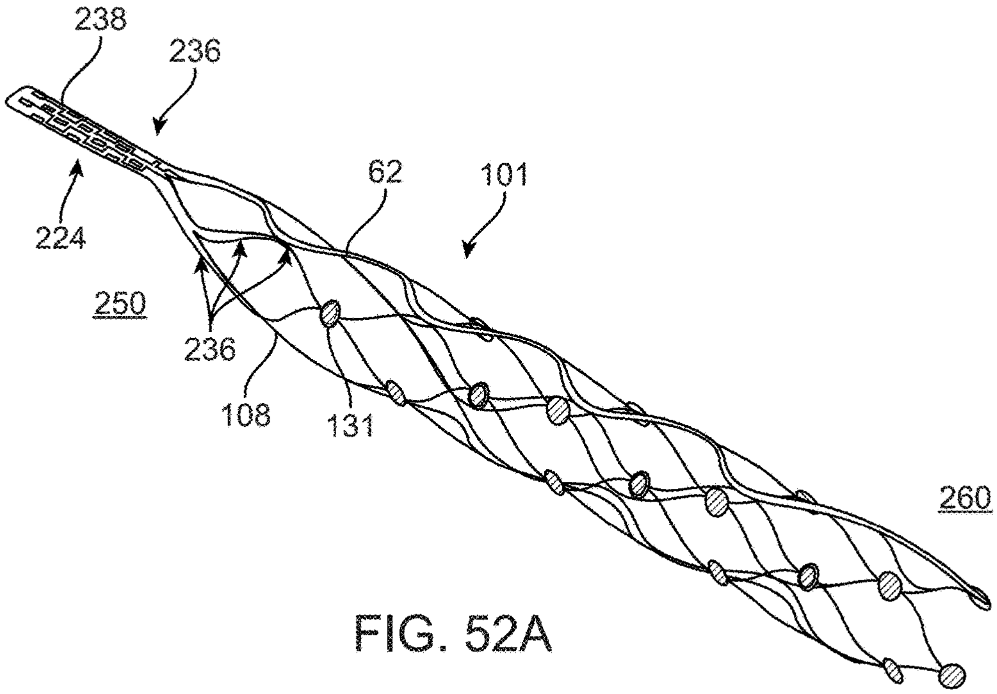
FIGS. 52A-52C illustrate a variation of a stent.
Figure 52B:
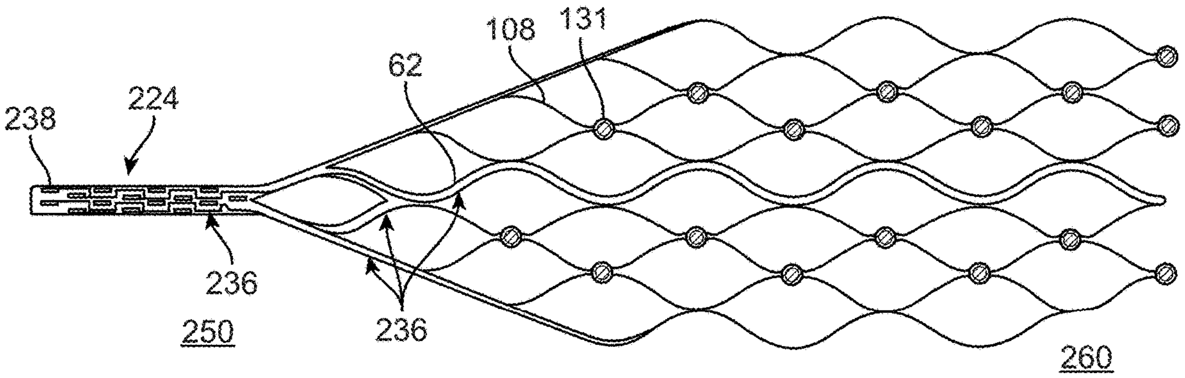
Figure 52C:
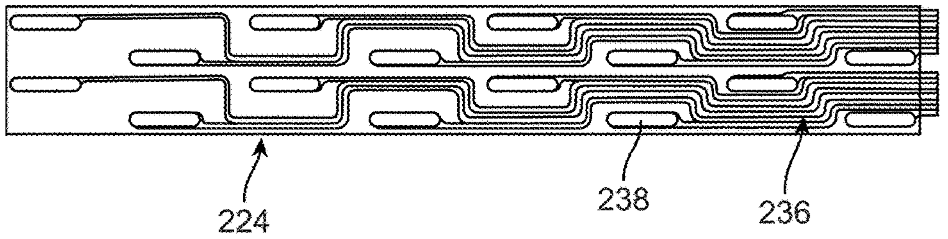

FIGS. 52A-52C illustrate a variation of a stent 101 having sixteen electrodes 131 arranged as shown. The proximal end 250 can include a second panel 224 as described above. The second panel 224 can have stent pads 238. FIG. 52A illustrates a perspective view of the stent 101 having a curved profile in an expanded configuration and FIG. 52B illustrates the stent 101 in a flat configuration. The stent 101 can have a reinforced section 62. FIG. 52B illustrates that some of the electrode tracks 236 can merge into a top, bottom, or middle strut 108, or any other strut. The middle strut 108 can be the reinforced section 62. Some of the struts 108 and/or the reinforced section 62 can get thicker from the distal end 260 to the proximal end 250. FIG. 52C is a magnified view of the proximal end 250 of the stent 101 of FIGS. 52A and 52B and shows the electrode tracks 236 electrically connected to the stent pads 238. An overlay 222 can be placed over the stent pads 238. The stent pads 238 can be directly connected to the lead wires 141 of a connector 200 (not shown). The stent pads 238 can be indirectly connected to the lead wires 141 of a connector 200 (not shown).

Figure 53A:
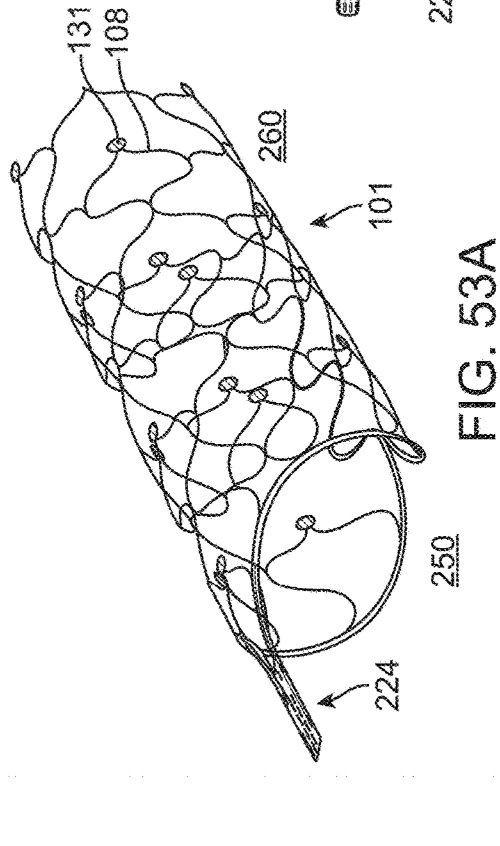
FIGS. 53A-53D illustrate a variation of a stent.
Figure 53B:
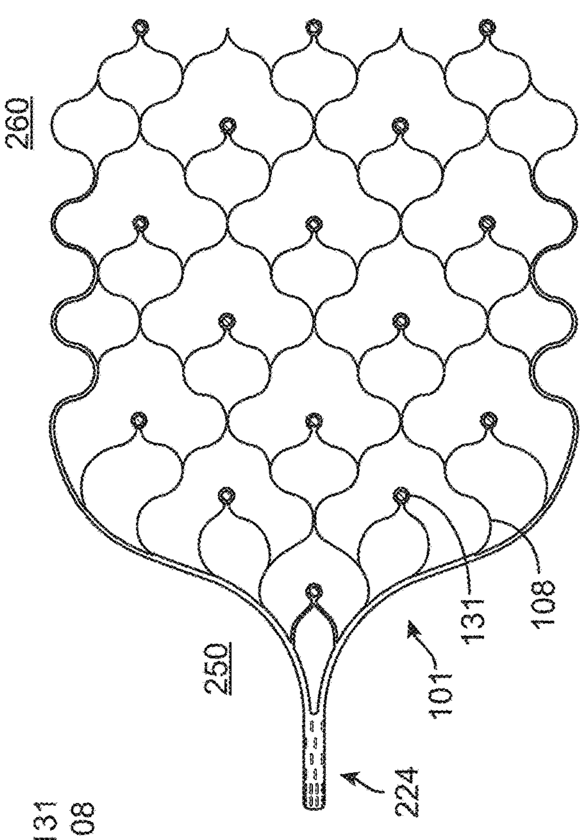
Figure 53C:
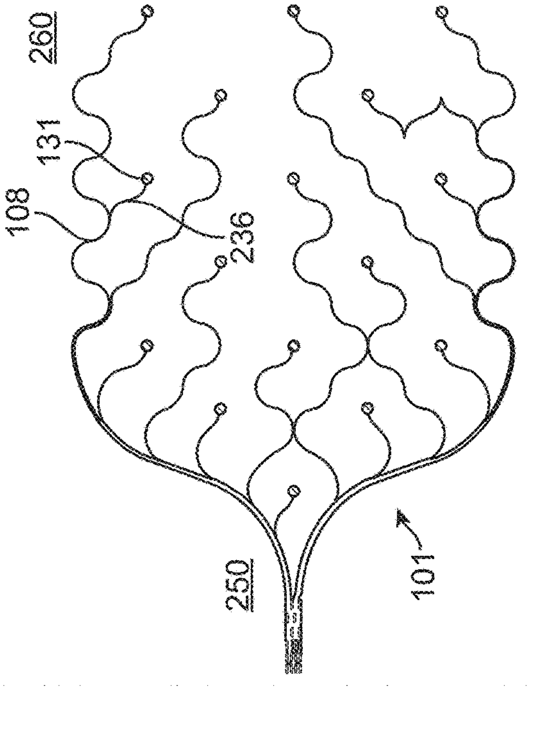
Figure 53D:
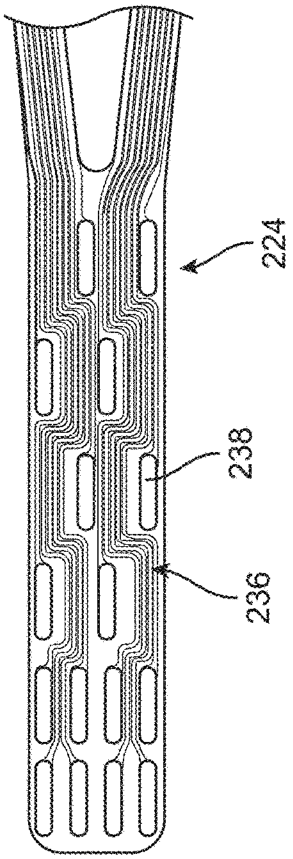

FIGS. 53A-53D illustrate a variation of a stent 101 having sixteen electrodes 131 arranged as shown. FIG. 53A illustrates a perspective view of the stent 101 having a curved profile in an expanded configuration. FIG. 53B illustrates the stent 101 in a flat configuration. FIG. 53C illustrates the struts 108 of FIGS. 53A and 53B that have electrode tracks 236. FIG. 53C illustrates that some of the electrode tracks 236 can merge into a top strut and some of the electrode tracks 236 can merge into a bottom strut. FIG. 53D is a magnified view of the proximal end 250 of the stent 101 of FIGS. 52A and 52B and shows the electrode tracks 236 electrically connected to the stent pads 238.

Figure 54A:
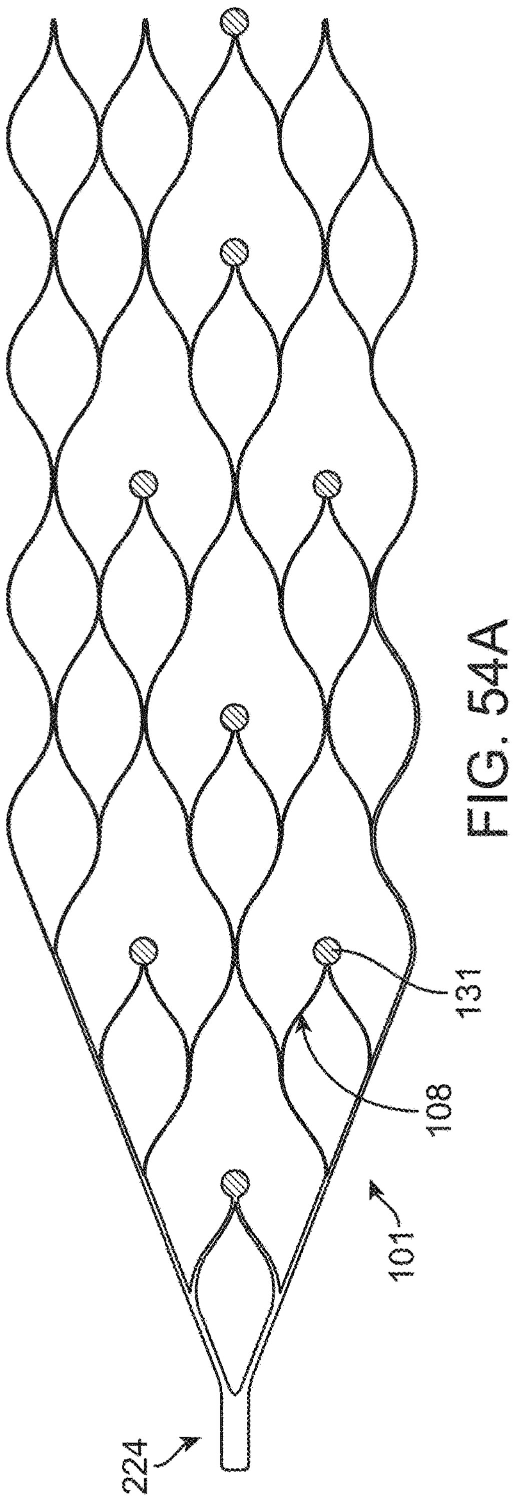
FIGS. 54A and 54B illustrate a variation of a stent.
Figure 54B:
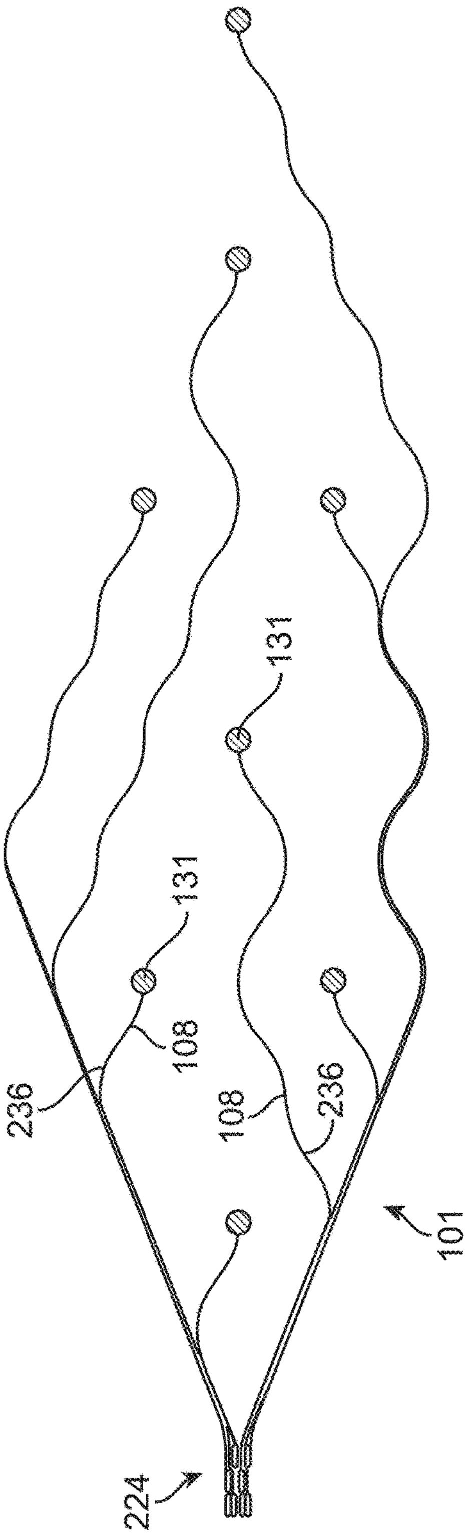

FIGS. 54A and 54B illustrate a variation of a stent 101. FIG. 54A illustrates that the stent 101 can have eight electrodes 131 arranged as shown. Other numbers of electrodes, more or less, are also appreciated. FIG. 54B illustrates the struts 108 of FIG. 54A that have electrode tracks 236. FIG. 54B illustrates that some of the electrode tracks 236 can merge into a top strut and some of the electrode tracks 236 can merge into a bottom strut.

Figure 55A:
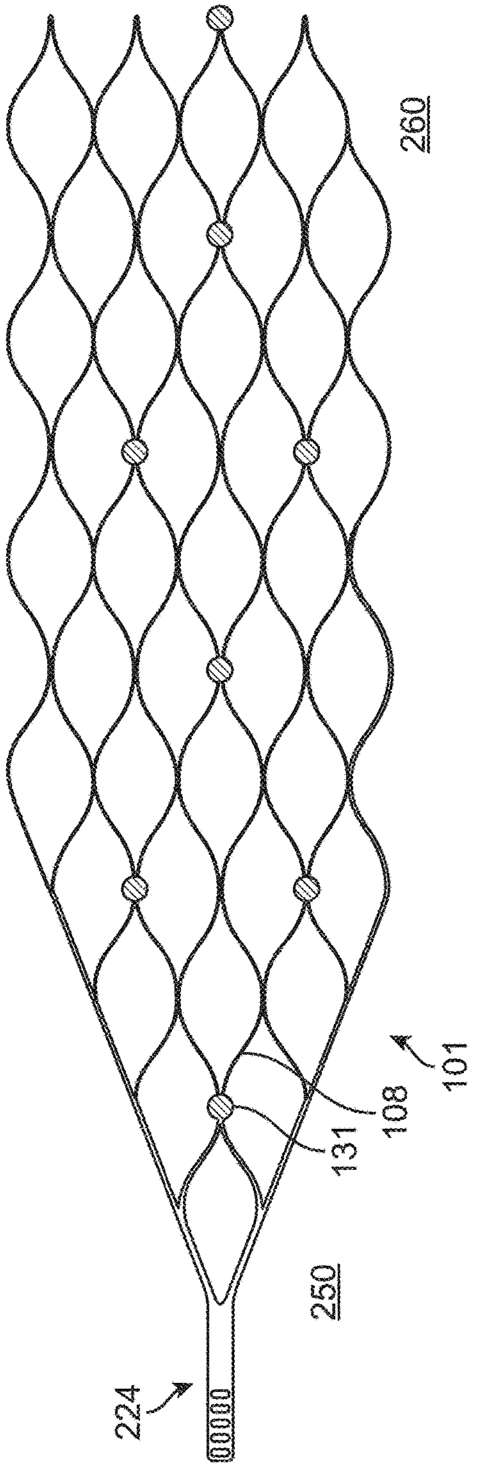
FIGS. 55A and 55B illustrate a variation of a stent.
Figure 55B:
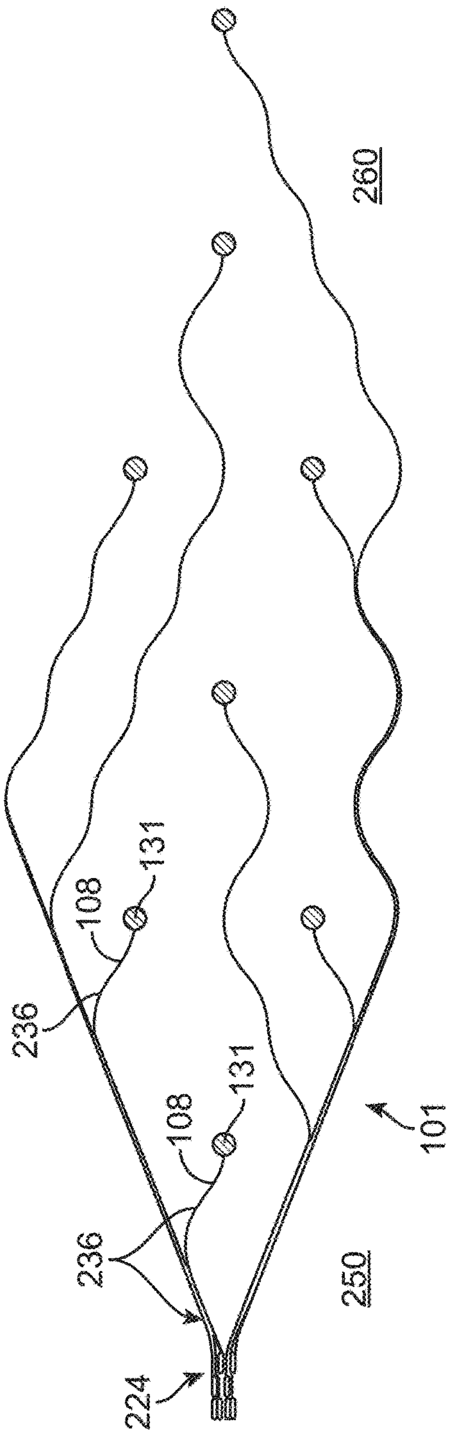

FIGS. 55A and 55B illustrate a variation of a stent 101. The stent 101 of FIGS. 55A and 55B is similar to the stent 101 of FIGS. 54A and 54B except that the cells in FIG. 55A have a uniform size.

Figure 56A:
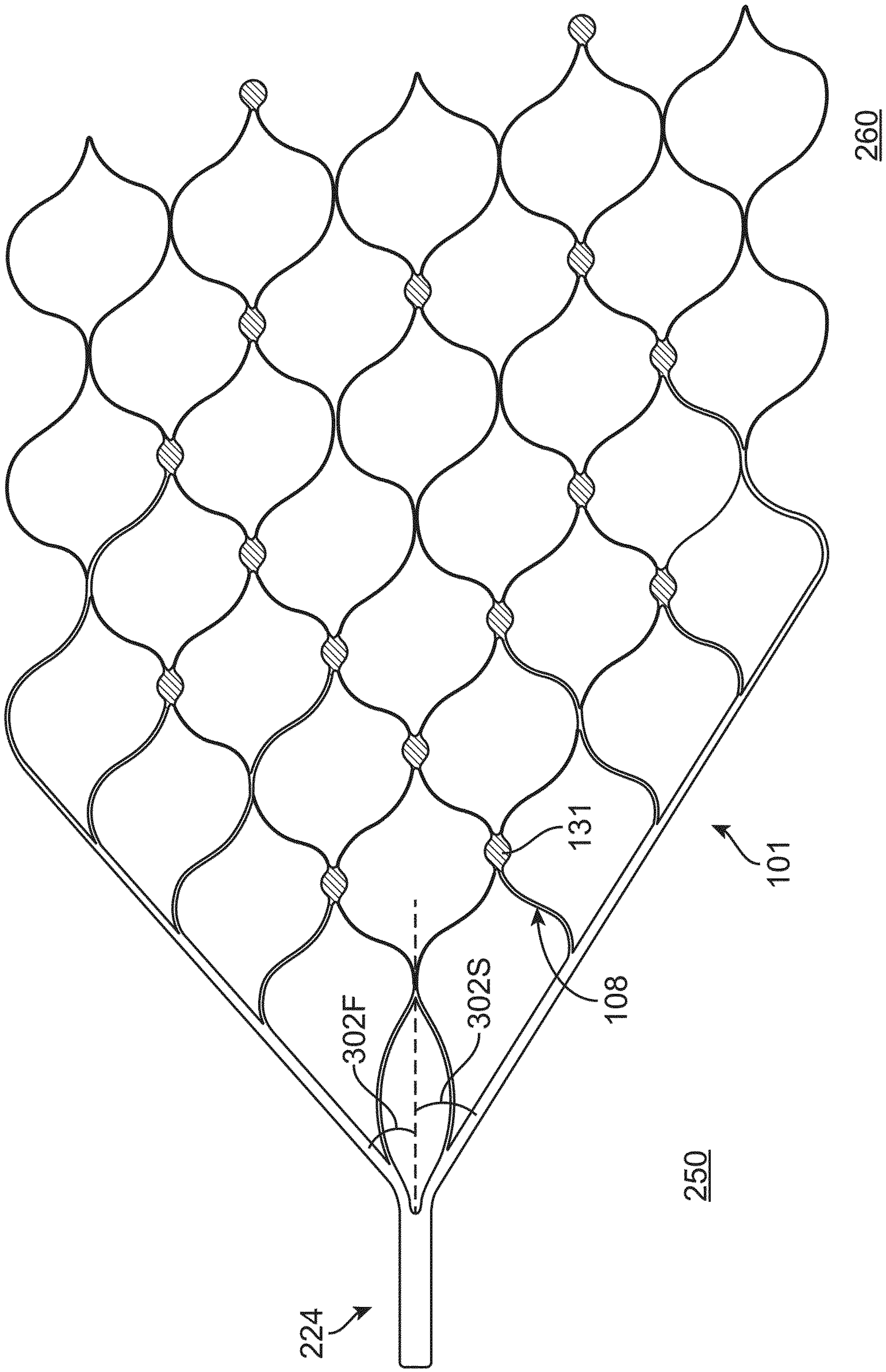
FIGS. 56A-56D illustrate variations of stents having various electrode configurations.
Figure 56B:
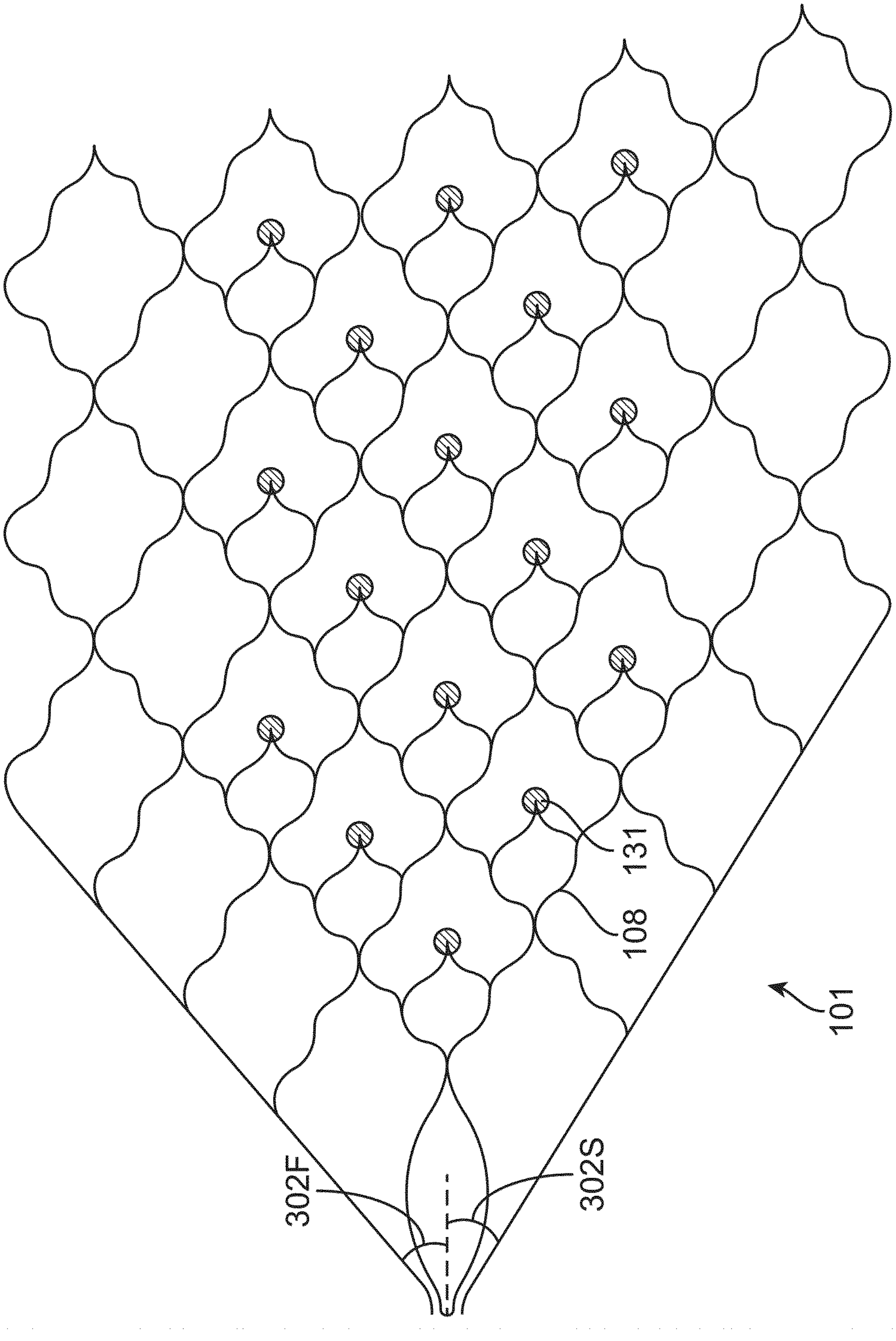
Figure 56C:
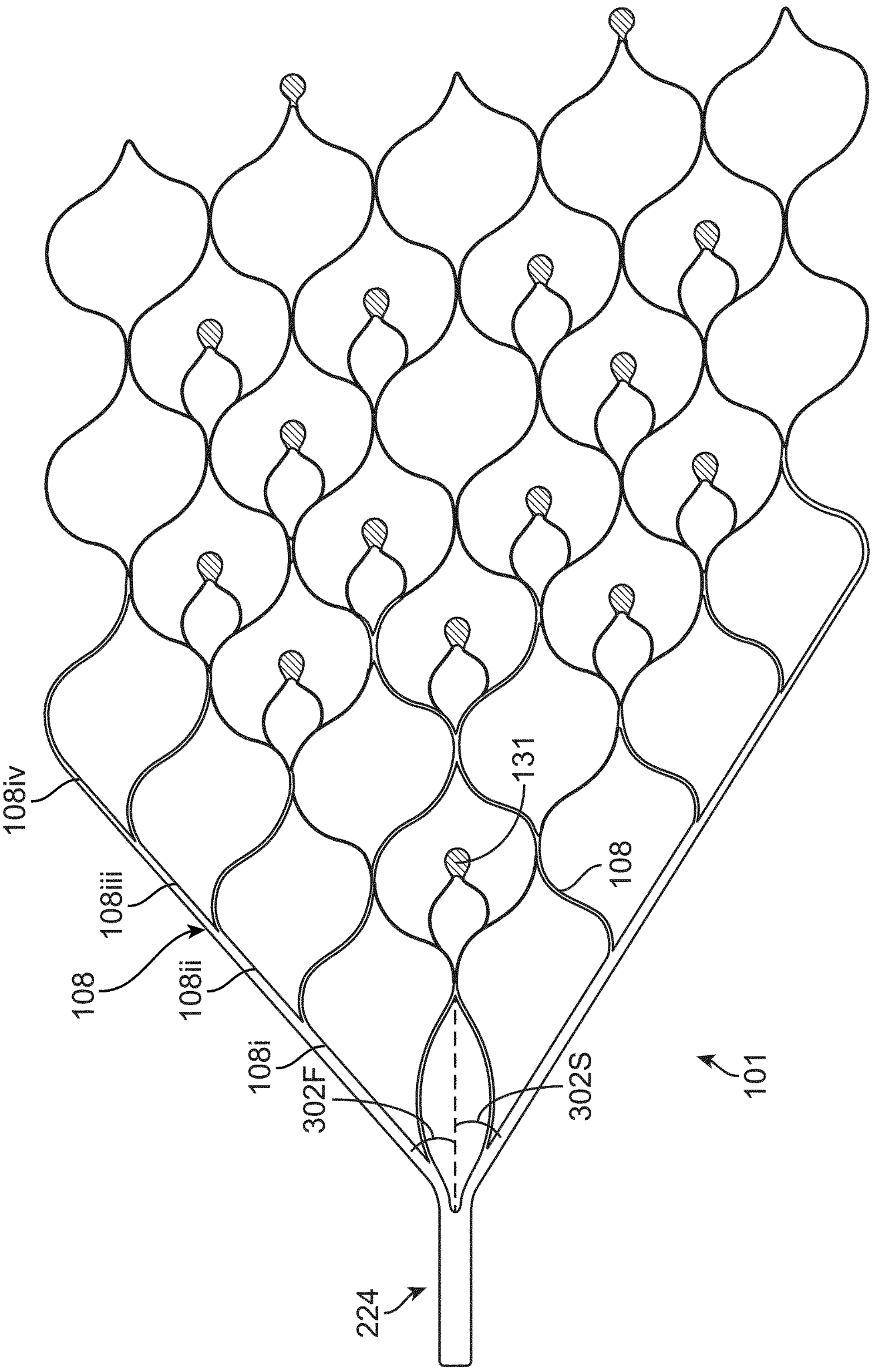
Figure 56D:
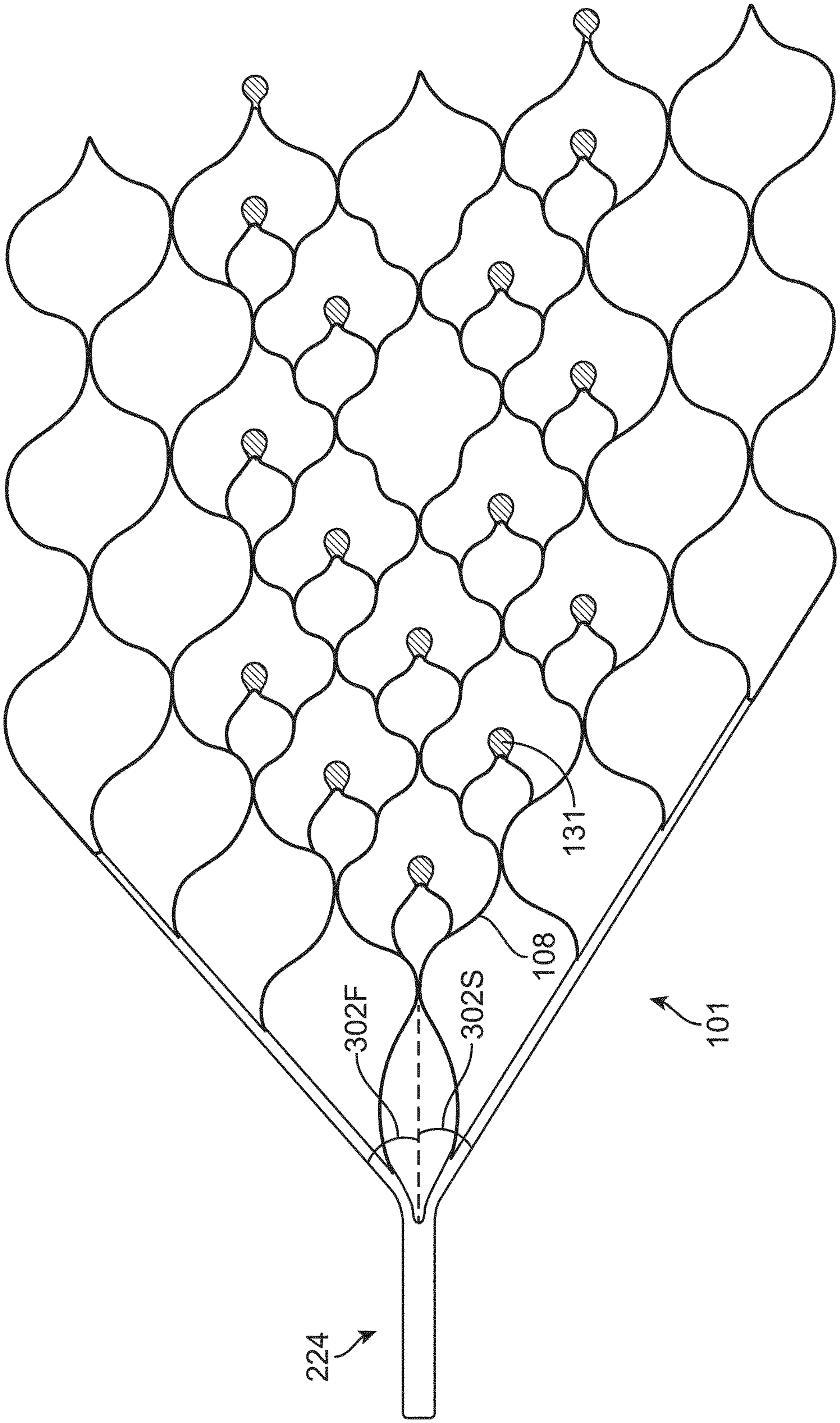

FIGS. 56A-56D illustrate various variations of stents 101 without electrode tracks. The stents 101 can have electrodes 131 arranged as shown. Other numbers of electrodes, more or less, are also appreciated. FIG. 56C illustrates that the struts 108 can have first, second, third and fourth portions 108*i*, 108*ii*, 108*iii*, and 108*iv*, respectively, where the thickness of the strut first portion 108*i* is greater than the strut second portion 108*ii*, where the thickness of the strut second portion 108*ii* is greater than the strut third portion 108*iii*, where the thickness of the strut third portion 108*iii* is greater than the strut fourth portion 108*iv*, or any combination thereof where the strut 108 has more or less portions. For example, the first, second third and fourth portions 108*i*, 108*ii*, 108*iii* and 108*iv* can have thicknesses, for example, of about 0.33 mm, about 0.29 mm, about 0.21 mm, about 0.13 mm, respectively.

Figure 57:
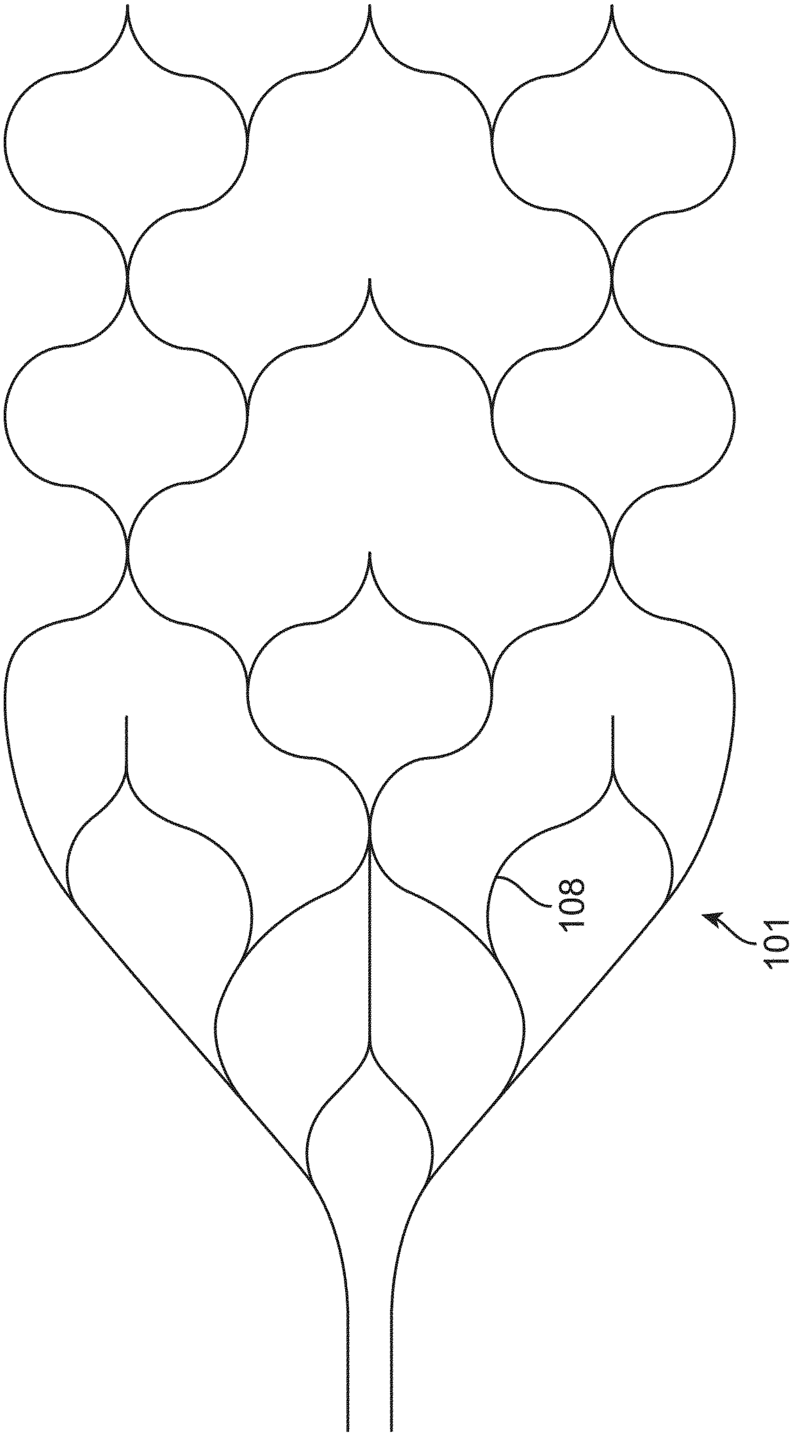
FIG. 57 illustrates a variation of a stent lattice structure.

FIG. 57 illustrates a variation of a lattice structure for a stent 101.

Figure 58C:
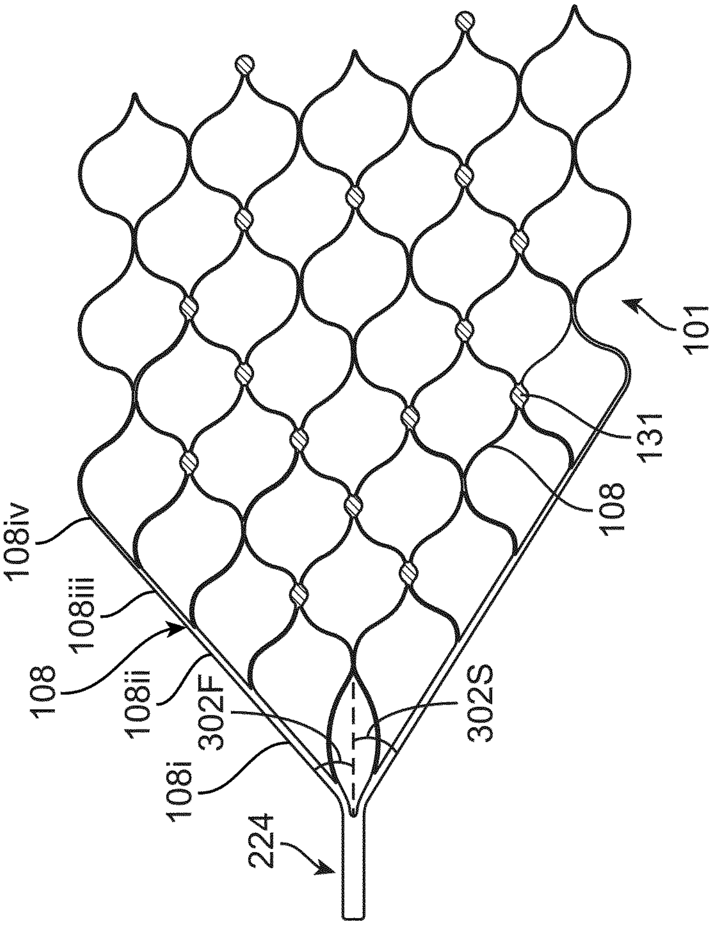
FIGS. 58A-58D illustrate a variation of a stent.
Figure 58D:
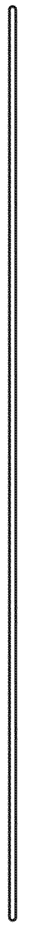
Figure 58A:
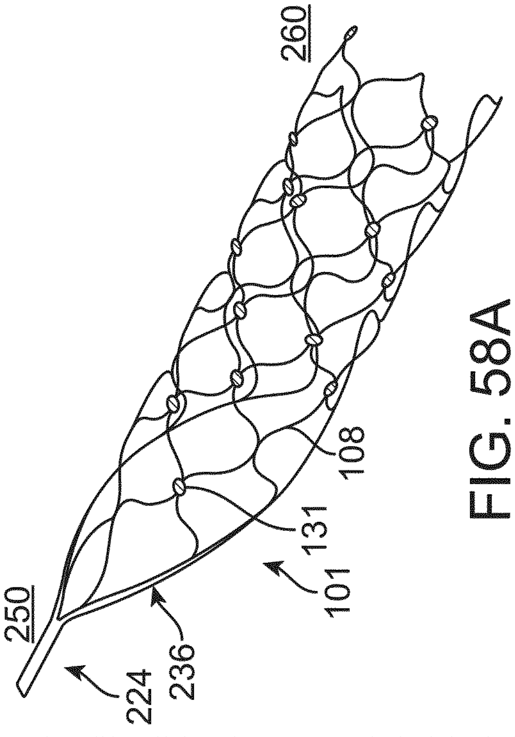
Figure 58B:
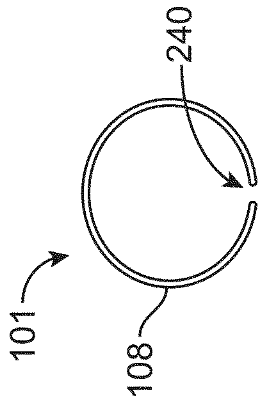

FIGS. 58A-58C illustrate a variation of a stent 101 having sixteen electrodes 131 arranged as shown. The stent 101 of FIGS. 58A-58C is similar to the stent 101 of FIG. 47F. FIGS. 58A and 58B illustrate perspective and side views of the stent 101 having a curved profile in an expanded configuration. The curved profile can have a gap 240. FIG. 58C illustrates the stent 101 in a flat configuration. The stent 101 can have the various dimensions shown (in millimeters) in FIG. 58C.

Any of the stents 101 disclosed and/or contemplated herein can be wireless stents (also referred to as wireless electrode systems). The stents 101 can have one or more wireless transmitters (e.g., the wireless transmitter 1002 of FIG. 31). The wireless transmitters can be attached to or integrated with the stents 101. The wireless transmitters can be a separate device and/or can be an arrangement of one or more electrodes 131 of the stents 101. For example, an arrangement of one or more electrodes 131 can form a wireless antenna that can send and/or receive information. The electrodes 131 can record or pick up neural information and relay this information to a wireless transmitter. This recorded information can be wirelessly transmitted through the skull to a wireless receiver (e.g., the wireless receiver 1004 of FIG. 31). The wireless receiver can decode and transmit the acquired neural information to a device such as a prosthetic limb or a visual prosthesis.

The wireless stents (e.g. stents 101) can be configured for the transmission of both power and data. Power can be wirelessly transmitted to the wireless stents to operate the circuitry of the stents and data can be wireless transmitted from the wireless stents to, for example, a control unit (e.g., control unit 12). In addition to or in lieu of the wireless power, the stents can be powered with a piezoelectric energy power generator that generates energy from blood flow and/or from vascular constriction and dilation.

The wireless stent systems can be fully or partly wireless. Fully wireless means that no portion of the stent (e.g., stents 101), including the electrodes 131 and wireless circuitry, extends beyond a vessel wall after implantation. Semi-wireless means that at least a portion of the stent (e.g., stents 101), electrodes 131 and/or wireless circuitry extends beyond a vessel wall after implantation. The stent 101 of FIG. 31 is an example of a fully wireless stent system. As shown in FIG. 31, the entire device (stent and electronics) can be within the blood vessel, or otherwise become embedded within the blood vessel over time. The stent 101 of FIG. 2A is an example of a semi-wireless system, where the wireless electronics sit outside the vessel in the pectoral region. The system of FIG. 2A is similar to, for example, a pacemaker where the wireless system sits outside of the vessel. Semi wireless systems can have a wire that passes from within a blood vessel to outside a blood vessel.

As described above, the stents 101 can be used to scaffold the electrodes 131 against the vessel wall. Wireless stent systems can have one or more stents (e.g., stents 101), for example, between one and ten stents (e.g., 1, 2, or 3 or more stents 101). Other numbers of stents, more or less, as well as ranges, narrower or wider, are also appreciated. If the wireless electronics cannot be mounted on or integrated with a first stent 101 having electrodes 131 (e.g., due to space or functional requirements), the wireless electronics can be mounted or integrated with a second stent 101 (e.g., which can have the same or a different number of electrodes than the first stent 101, or no electrodes). Such multi-stent systems (e.g., dual-stent systems) can advantageously carry the circuitry away from the center of the vessel where it has a chance of causing occlusion or blockage. The first and second stents of a dual-stent system can advantageously form a dipole antenna, which can improve wireless transmission of the system. The second stent can be under the skull connected directly (but not electrically) to the first stent, or can be placed in the neck, tethered to the first stent. Other arrangements are also appreciated (e.g., the first and second stents can be electrically connected to one another). A benefit of placing the second stent in the neck includes a reduction in distance to the body surface. Placement in the neck is also expected to cause less interference to the acquisition and amplification of the neural signals.

The system (e.g., system 10) can have one or more stents 101 in wired and/or wireless communication with a telemetry unit (e.g., control unit 12). For example, the system can be an endovascular telemetry and closed loop cortical recording and/or stimulation system for the diagnosis, prediction and treatment of epilepsy. Endovascular telemetry systems for epilepsy (also referred to as epilepsy care systems) can advantageously record brain activity 24 hours/day 7 days/week. This 24/7 monitoring offers a critical advantage to doctors and patients alike, as traditionally the ability of the treating physician to determine the number of seizures a patient is suffering depends on the patient recording a seizure diary, which can be, and are notoriously, inaccurate. Knowing how many and the nature of seizures occurring in a patient can be critical in determining the correct dosing for anti-seizure treatment by the physician, which the endovascular telemetry system provides. The epilepsy care systems can receive inputs that can modulate treatment doses of medications/drugs.

For recording telemetry, a stent 101 can be implanted in cortical venous targets (including the transverse sinus) to achieve proximity to cortical regions of interest for seizure detection (including the temporal lobe). The stent 101 can be or can be part of an implantable telemetry unit (ITU). The ITU can house a data unit that can collect brain recordings 24/7. The ITU can be accessed wirelessly by the user or physician to review the neural information over a time period of interest. The ITU can be accessed wirelessly for real-time assessment of the neural information. For example, in periods of higher-risk (including when the patient is unwell, or having to make modifications to their treatment regimen) the physician is able to assess neural signal in real time. The neural data collected by the ITU can be streamed into a range of apps that allow various real time functions. For example, the neural data collected can be communicated to third party applications that apply software analysis of the neural data (including for seizure prediction). In this way, the collected data can be made available to third party users to generate information or modulation information to the patients upon use of the collected data. The epilepsy care systems can have closed loop feedback. For example, the collected data can be utilized in an input loop into a treatment-delivery system to enable precise dosage determinations based upon data containing real-time seizure detection (including vagal nerve stimulator, drug delivery systems). The epilepsy care systems can perform neuromodulation. For example, responsive neural stimulation can be achieved by the endovascular systems described herein having stents 101. This can advantageously enable a closed loop system by utilizing the stent system to record and deliver treatment by stimulating across the vessel wall (e.g., from one or more electrodes 131 of one or more stents 101) to achieve seizure termination.

Figures 59A, 59B, 59C:
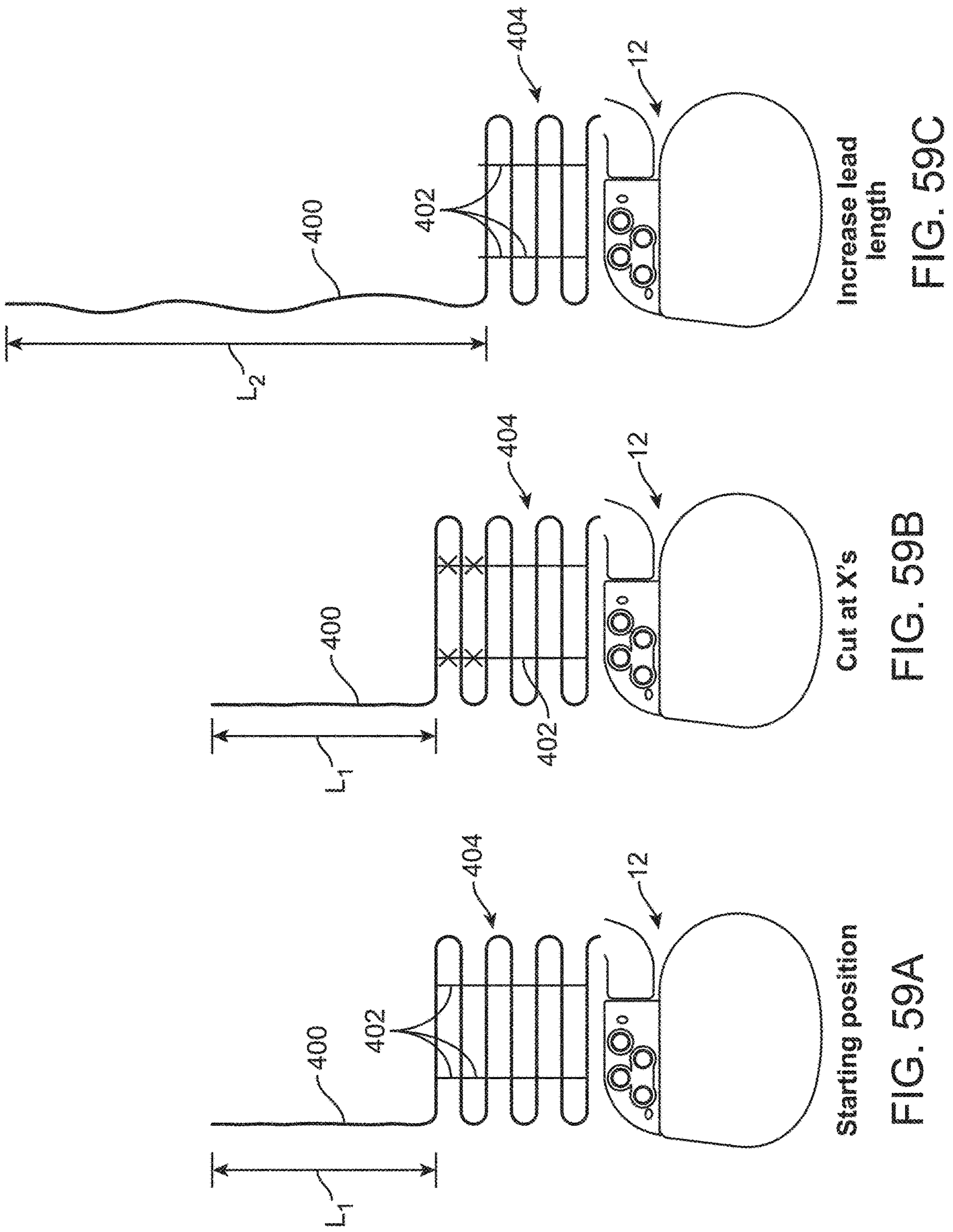
FIGS. 59A-59C illustrate a telemetry unit lead having a snake and rung configuration.

FIGS. 59A-59C illustrate a telemetry unit lead 400 having a snake and rung design connected to a telemetry device 12. The snake and rung design can advantageously reduce the surgical manipulation required to shorten the lead 400, for example, if the lead is too long. Typically, leads are shortened by winding the lead on itself; however, such winding can cause fatigue as the lead rubs on itself and wears away and/or can require a larger incision into muscles during surgery. The snake and rung design prevents/avoids these risks. As shown in FIGS. 59A-59C, the telemetry unit lead 400 can be a set overall size (e.g., overall length) that is curled into a snake form 404 connected by one or more rungs 402. The rungs 402 can be made of silicone or other biocompatible material that has some flex. If a longer lead is required, one or more of the rungs 402 can be detached (e.g., through surgical cutting or otherwise) so that the lead length can be increased. In this way, the length of a generic telemetry unit lead 400 can be tailored/customized to a patient and to the surgical placement of the telemetry device 12 during surgery. For example, FIGS. 59A-59C illustrate that the lead length can be increased from $L_1$ to $L_2$ by detaching four rungs 402, for example, during surgery. One or more rungs 402 (e.g., one, two, or three or more) can be placed centrally or on the left and/or right edges of the snaked portion 404 of lead 400, or somewhere in between.

As described above, the telemetry unit (e.g., control unit 12) can communicate information (using wires or wirelessly) to and/or from an external apparatus 16, which can include (but is not limited to) one or more of the following: (a) an exoskeleton; (b) wheelchair; (c) computer; and/or (d) other electrical or electro-mechanical device.

Figures 60A, 60B, 60C, 60D:
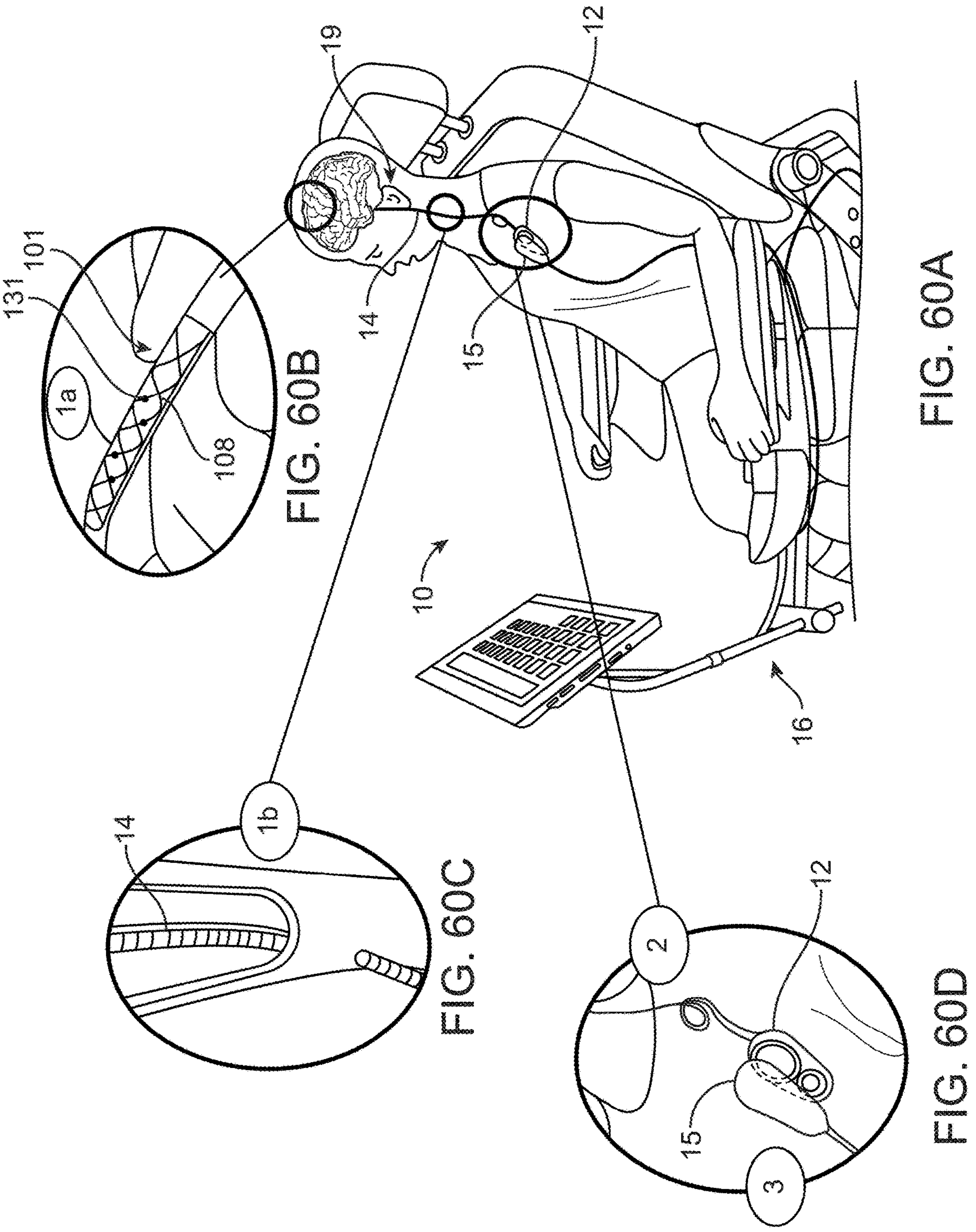
FIGS. 60A-60D illustrate a variation of a system having a stent in communication with an external apparatus.

For example, FIGS. 60*a*-60*d* illustrate a variation of a system 10 having a stent 101 implanted in the vascular of a person's brain, for example, a vessel traversing the person's superior sagittal sinus. FIG. 60*a* illustrates the system 10 and FIGS. 60*b*-60*c* illustrate three magnified views of the system 10 as shown. The stent 101 can be implanted for example, via the jugular vein, into the superior sagittal sinus (SSS) overlying the primary motor cortex to passively record brain signals and/or stimulate tissue. The stent 101 can record and interpret brain signals that are associated with intentions to move, so that people who are paralyzed due to neurological injury or disease, can communicate, improve mobility and potentially achieve independent through direct brain control of assistive technologies such as computer software and/or apparatuses 16 (e.g., robotic upper limb prostheses, motorized wheelchairs, and the like). Other applications for the stent 101 as described throughout this disclosure are also appreciated.

The system 10 can have one or multiple telemetry units. The system 10 can have one or multiple internal and/or external telemetry units. FIGS. 60*a* and 60*d* illustrate that the system can have an internal telemetry unit (e.g., control unit 12) in wired or wireless communication with an external telemetry unit 15. For example, the external telemetry unit 15 can be wirelessly connected to the internal telemetry unit 12 across the user's skin. The internal telemetry unit 12 can be in wireless or wired communication with the stent 101. For example, FIGS. 60*a*-60*d* illustrate that the stent 101 can be electrically connected to the internal control unit 12 via a communication conduit 14. The communication conduit 14 can be a stent lead. As shown in FIG. 60*c*, the stent lead can extend from the stent 101, pass through a wall of the jugular, and tunnel under the skin to a subclavian pocket. In this way, the communication conduit 14 can facilitate communications between the stent 101 and the internal control unit 12.

As shown in FIGS. 60*a*-60*d* (as well as FIGS. 1-2B), the one or multiple telemetry units can be located/implanted in and/or on the chest of a user. However, the telemetry unit can be located in any suitable location. For example, the telemetry unit can be located/implanted behind the ear of a user. For example, one or multiple telemetry units can be located/implanted behind the ear of the user at, or otherwise proximate to, location 19 shown in FIG. 60*a*. Relative to placement in and/or on the chest, positioning the control unit behind a user's ear can advantageously reduce artifacts and noise due to neck and muscle movement, for example, because the communication conduit 14 (e.g., stent lead) would not need to be located in the neck of a user.

The internal telemetry unit 12 can be connected to one or multiple external apparatuses 16. The internal telemetry unit 12 can be connected to one or multiple internal apparatuses (not shown), for example, visual prosthetics and other controllable devices implanted partially or completely within or on a person's body. The external telemetry unit 15 can be connected to one or multiple external apparatuses 16. The external telemetry unit 15 can be connected to one or multiple internal apparatuses (not shown), for example, visual prosthetics and other controllable devices implanted partially or completely within or on a person's body.

As described above, the system (e.g., system 10) can have one or more stents 101. The stents 101 can be in wired and/or wireless communication with a telemetry unit (e.g., control unit 12). The stents 101 can record and or stimulate areas of the cortex associated with vision. For example, the system can be an endovascular visual prosthesis neural interface having one or more stents 101. The stent 101 can be used to access deep, folded areas of cortex in the occipital lobe (e.g., the primary visual cortex) that are not reachable via open brain surgery, and which cannot be targeted by current technology (i.e., technology that is implanted directly onto the cortical surface of the occipital lobe). FIG. 34 shows a method for stimulation and the recording neural information or the stimulation of neurons from the visual cortex of a patient using the device 100, including the steps of: (a) implanting the device in a vessel in the visual cortex of the patient; and (b) recording neural information associated with the vessel or stimulating neurons in accordance with received stimulation data. The stents 101 can be implanted in the superior sagittal sinus and/or the transverse sinus to advantageously achieve transvascular stimulation of the occipital region of interest, although any implant location is appreciated. Information from the visual world can be captured in a video capture. The information can be translated into a stimulation algorithm. The translated information can be delivered into the occipital lobe via stimulation via one or more stents 101. The visual prosthetic system can contain a large number of electrodes embedded into the wall of the transverse and superior sagittal sinus via the one or more stents 101.

The one or more stents 101 can be used for an endovascular neural interface system for deep brain stimulation treatment. Current deep brain stimulation requires a craniotomy for implantation of the leads. Craniotomy procedures are associated with myriad complications and risks including hemorrhage. The stents 101 can eliminate the need for craniotomies. The stents 101 can access to deep structures suitable as targets for deep brain stimulation is viable through deep venous and arterial vessels in the brain. A catheter can be used to access the deep blood vessels. The stents 101 can enable stimulation of targeted brain tissue.

Implantation of an endovascular lead into a deep structure can enable stimulation of the brain tissue. The stents 101 and systems disclosed herein can treat a range of conditions with deep brain stimulation, including Parkinson's disease, dystonia, obsessive compulsive disorder, depression, among others. Many modifications will be apparent to those skilled in the art without departing from the scope of the present invention.

Electrode Array Nerve Cuff

Another variation of the electrode systems disclosed and contemplated herein includes nerve cuff electrode systems. Additionally or alternatively, the systems described and contemplated herein can also function as nerve cuff electrode systems. For example, for nerve cuff electrode systems, the electrodes of the stents 101 can be on the internal side of the stent such that they are configured to face toward the nerve or nerve bundle for the stimulation and/or recording of energy when the stents 101 are deployed to function in a nerve cuff capacity (e.g., one or all of the electrodes can face or be directed in the opposite direction as the direction shown in the above-described stent configurations). The nerve can be in the wall of a blood vessel anywhere in the body. The nerve can be unaffiliated with a blood vessel. In practice, nerve cuff electrodes can be used to record and/or stimulate accessible nerves directly, and can be used to stimulate nerves for movement restoration and tactile feedback, as well as stimulation of internal nerve bundles (e.g., vagus nerve) for gut and parasympathetic interactions and pain, and measurement of internal neurons to assess neuronal and organ health. Nerves can be exposed and the cuff electrodes can be wrapped around them. Existing nerve cuff electrodes are difficult to attach and secure, and require buckle or attachment systems to strap the electrodes around the nerve. These buckle and attachment systems induce artefacts when the cuff electrodes move and can produce unreliable signals (e.g., when recording) or loss of current and subsequent sub-threshold activation when stimulating. Advantageously, the stents 101 do not require buckles or separate attachment systems, but can include them.

Figure 61A:
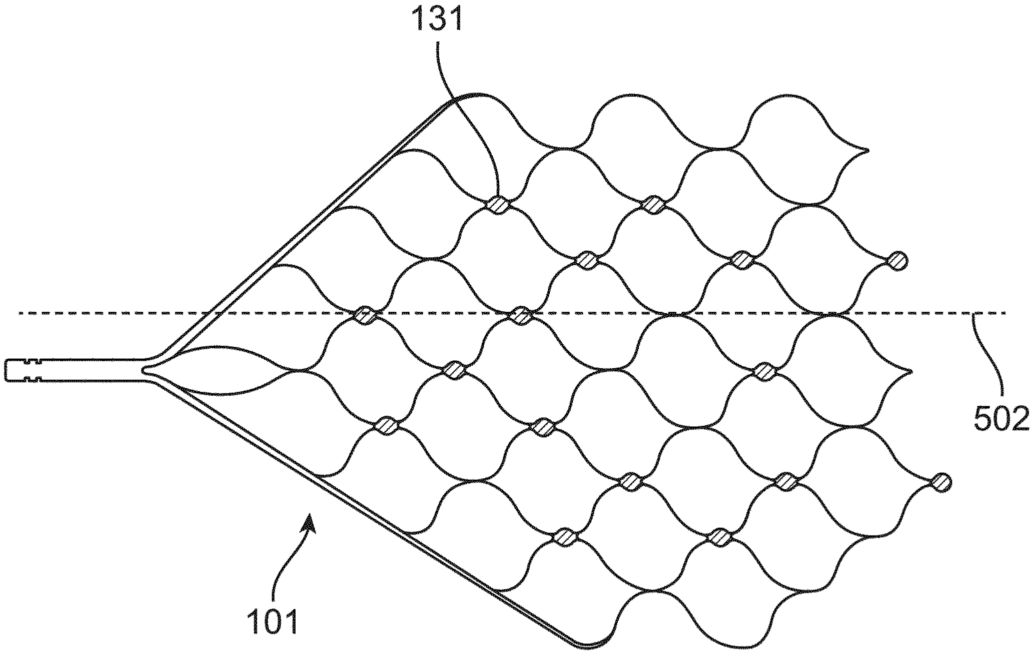
FIG. 61A illustrates a variation of a nerve cuff.
Figure 61B:
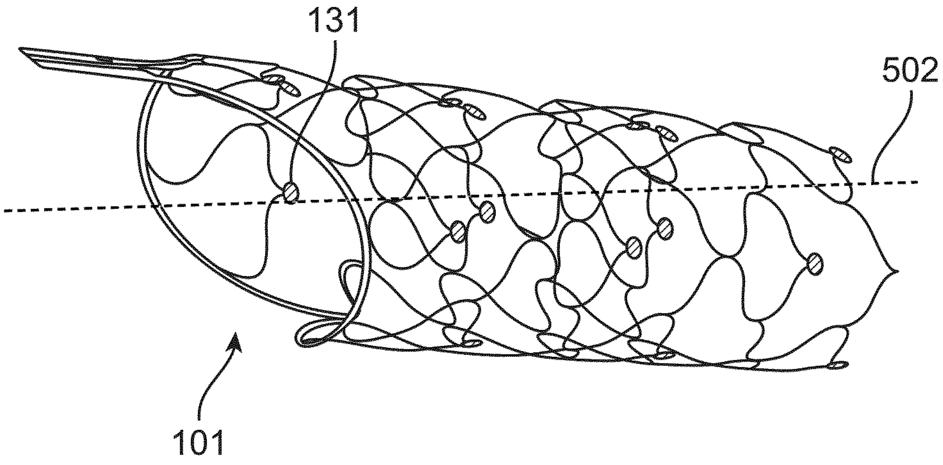
FIG. 61B illustrates the nerve cuff of FIG. 61A deployed around a nerve.

The nerve cuff electrode arrays can be stent electrode arrays (e.g., stents 101 having the electrodes pointed in the opposite direction, for example, toward a center axis of the stents). The nerve cuff stents 101 can be biased to deploy partially or entirely around one or multiple nerves. For example, the nerve cuff stents 101 can be biased to collapse or self-collapse around a nerve or nerve bundle. FIGS. 61A and 61B illustrate a variation of a method of implanting a nerve cuff electrode array 101 having electrodes (e.g., electrodes 131 and/or 138). FIG. 61A illustrates that the stent 101 can be positioned over a nerve and/or vessel 502 in an open (e.g., flattened) configuration. Once the stent 101 is in the desired location, FIG. 61B illustrates that the stent 101 can be allowed to compress and curl over (e.g., partially or completely around) the nerve and/or vessel 502. The electrodes can be energized to activate the nerve. Using a self-collapsing stent (e.g., stent 101) as a nerve cuff advantageously improves the ability to have a larger number of electrodes as part of the nerve cuff and allows for the removal of manual buckles or straps to maintain position. The nerve cuffs 101 can be manufactured with thin-film technology, so can have very accurate electrode sizes and locations. The electrodes can be attached to, integrated with, or built on miniature shafts or spikes so that the electrodes on the inside of the stent have a pillar or pyramidal shape and can be pressed into the nerve directly to access and record or stimulate fibres that are located centrally to the nerve bundle. This gives increased ease of implantation, increased reliability and manufacturing repeatability and enhanced performance and ability of the electrode to access and interact with surface and deeper nerve fibres. Additionally or alternatively, any of the stents and stent-like structures described herein can have electrodes on the inside and the outside of the device.

Electrode Wires/Tracks

The electrode lead wires can be made using thin film technology, which can advantageously reduce the thickness of the electrical pathways in the blood vessels or other locations in the body. The electrical pathways can be wires, conductive tracks (e.g., manufactured using thin film technology), or both. The electrical pathways can be implanted in the lumen of blood vessels, in the wall of blood vessels, outside of blood vessels, or any combination thereof. Conductive tracks leading to and from the electrodes can desirably take up less space than wires by virtue of having a smaller cross-sectional size than wires. Since blood vessel lumens have a finite size, decreasing the cross-sectional size of the lead wires (e.g., by using thin film electrode tracks) can increase the amount of the lumen space that is available for blood flow as compared to when conventional wires are used. Using conductive electrode tracks can desirably result in thinner electrical pathways to and from any of the electrode arrays described and contemplated herein (e.g., the stents 101), for example, as compared to wires. Also, although electrode lead wires and electrode thin film tracks each have disadvantages, this disclosure is not teaching against implementing either, as each technique, alone or in combination with the other, can be used to directly or indirectly connect the electrodes of the arrays disclosed herein to a controller, whether that controller is positioned in the brain, neck, chest, or elsewhere in or on the body, or on the stent itself. For example, when wires are used, each electrode wire has a thickness, and this thickness can limit the number of electrode wires that can be implanted within a vessel of set diameter. This can be effectively managed by choosing the appropriate number and size of wires and/or by using electrode tracks in addition to wires. As another example, when electrode tracks are used, the tracks can have an increased electrical resistance, fragility, risk of breakage, and fatigue as compared to conventional wires. However, this can be successfully managed by choosing the appropriate thickness and number of electrode tracks and/or by using wires in addition to the use of non-wire electrode tracks.

Additionally or alternatively, the electrode wires and/or tracks can be arranged in a coil that defines an internal lumen where the internal lumen can allow fluid (e.g., blood) to flow through. The coil can have a spiral arrangement such as a helix. The coil lumen can be smaller than, larger than, or approximately the same size as the blood vessel lumen. The coil can have one or multiple lumens. An axial center of the coil lumen can align with or be offset from the blood vessel lumen. The coil can be attached to, integrated with, absorbed into the blood vessel wall, or any combination thereof. The coil can be coated with bioabsorbable coating. The coil can have anchors configured to attach to and/or extend through the vessel wall.

Having a coil of wires and/or electrode tracks can desirably reduce the amount of space needed for the electrical pathways inside the vessel, leaving more of the blood vessel lumen available for blood flow or other devices (e.g., blood pressure sensors). The coil of electrical pathways can thereby block less of the vessel lumens as compared to conventional techniques. For example, a large coiled wire bundle with a central lumen that allows for the passage of blood can be implanted. This cable, like the stents 101, can be incorporated into the vessel wall. By using thin film technology, these cables can be made very thin, although generic ribbon cables (or bunched wires) can also be shape set to the dimensions of the vessel to allow for both deployment and incorporation. The cables can be custom shape set to match a person's unique vessel tortuosity. The method by which the cable is coiled can ensure the force is sufficient to push the device for deployment (which can be but need not be included for a device with a magnetic tip), whilst also allowing the coils to be compressed in smaller diameter regions of vessel. During deployment, the coil can have a constant diameter or can have multiple diameters across the length of the coil, for example, depending on the external environment, the vessel tortuosity, the vessel size, the vessel lumen size, or any combination of these factors. After implantation, the coil can have a constant diameter or can have multiple diameters across the length of the coil, for example, depending on the external environment, the vessel tortuosity, the vessel size, the vessel lumen size, or any combination of these factors.

Electrode Track Arrangement

The struts 108 of the stentrodes (e.g., stents 101) disclosed and contemplated herein can carry the electrical tracks to and from the electrodes. The number of tracks (and hence number of electrodes) can be increased by having multiple layers of conductive material. However, with each increase in conductor, there also needs to be an increase in insulation (and thicker insulation to prevent electrical cross talk and capacitive interference). As another example, the number of tracks can be increased by decreasing the track thickness to have more tracks per strut. Each strut can have one or multiple electrode tracks. Each strut can have one or multiple layers of conductive material. Additional or alternatively, the number of tracks can be increased by overlaying multiple thin film electrodes on top of each other. This can allow the separate thin film designs to retain the thick electrode tracks required for durability and electrical resistance reduction, and also allows for many more electrodes to be implanted. In this way, multiple thin film conductive pathways can be overlaid to form layered pathways, layered electrodes, or both. Such overlaid designs can desirably overcome the issue faced with current limitations of printing multiple track layers, and can also ensure that each individual stent is thin, assisting with incorporation and also assisting with flexibility (e.g., two of set thickness can be more flexible than one of double thickness).

Stent Length

The entire device or the part implanted within the blood vessel can be a stent (e.g., stents 101), for example, a tubular stent. In such variations, the cable can be removed from the device but need not be. The electrode tracks can traverse on or through the struts the entire length of the stent 101. The stents 101 can have a length from about 5 mm to about 750 mm or more, including every 1 mm increment within this range (e.g., 5 mm, 30 mm, 100 mm, 200 mm, 300 mm, 400 mm, 500 mm, 600 mm, 700 mm) and every 10 mm range within this range (e.g., 5 mm-15 mm, 30 mm-40 mm, 100 mm-110 mm, 200 mm-210 mm, 300 mm-310 mm, 400 mm-410 mm, 500 mm-510 mm, 600 mm-610 mm, 700 mm-710 mm) The stent can be implanted in one or multiple blood vessels. When implanted, the stent can be implanted at a junction between a first blood vessel and a second blood vessel and in one or both of the first and second blood vessels. The stent can have a length such that a first portion is in the brain, a second portion is in the neck, a third portion is in the body below the neck (e.g., chest), or any combination thereof. One or more sections of the stent can be energized or record signals independently from one or more other sections of the stent. The stent length can refer to the length of the stent when the stent is in an unexpanded configuration, a partially expanded configuration, or a fully expanded configuration. The stent 101 can be made in one or multiple pieces. For example, the stent 101 can made from a single wafer. Stents 101 having long lengths can have the ability to be implanted in one or multiple vessels, for example, from the same entry point. Stents 101 having long lengths can desirably remove the errors between connections, for example, with a stent lead.

Stents 101 without lead wires and cables can be used. For example, long stents 101 can eliminate the need for lead wires and cables. Removing the cable can advantageously reduce this risk of vascular blockage by reducing or eliminating eddy currents that can form at the transition between the stent (e.g., incorporated into the vessel wall) and the cable (e.g., positioned and incorporated into one side of the vessel wall) since eddy currents can contribute to the formation of thrombus or occlusion. Removing the cable can also desirably eliminate the electrical connection needed between the tracks and the cable, which can have a risk of fatigue, and thereby improve the connection reliability, connection diameter and geometry and lead incorporation.

Stent and Cable Connection

The electrodes mounted or embedded within the stents 101 can be connected to a cable to relay the information recorded by the electrodes (e.g., in the brain) to equipment or connectors outside the blood vessel and body. The electrode tracks and the cable can be connected in various ways.

Figure 62A:
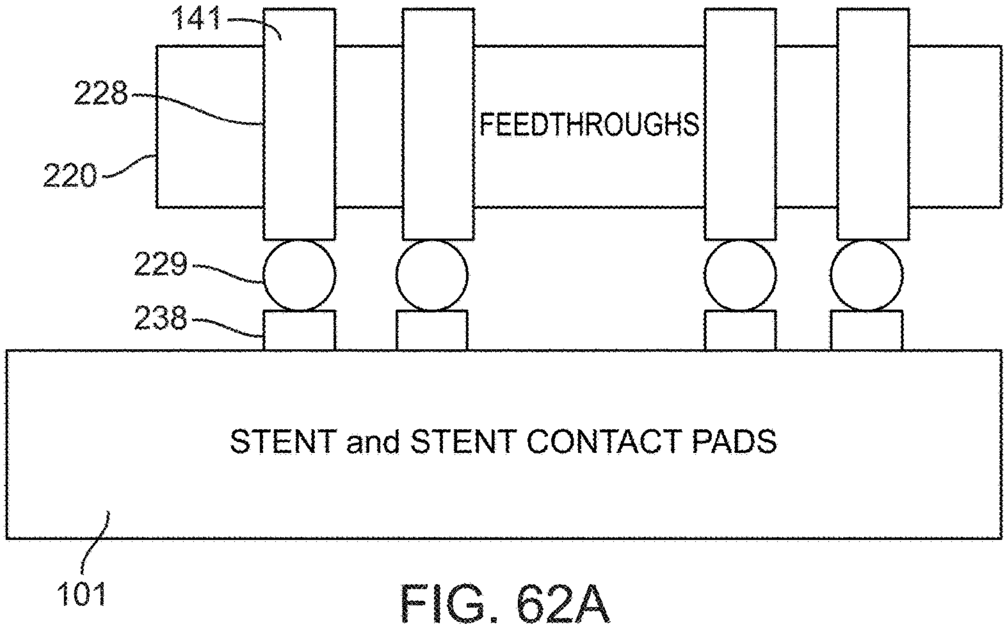
FIG. 62A illustrates a variation of a stent and cable connection.

For example, FIG. 62A illustrates a variation of a connection in which bump bonds 229 can connect the electrode pads 238 on the stent 101 to the lead wires 141 directly. The lead wires 141 can pass though the openings 228 (also referred to as through holes) in the connection panel 220. Additionally or alternatively, the wires 141 in FIG. 62A can be feedthroughs ultimately connected to the wires 141 where bump bonding from the pads on the stent to feedthroughs on an interposer (e.g., connection panel 220) are connected to wires 141 that form the lead or cable. The wires 141 and feedthroughs can be flat. The wires 141 and feedthroughs can be made of soft materials that can be flattened during the process and connected to, for example, metals including platinum and aluminum oxide. The connections shown in FIG. 62A can be included for stents having any length but are not required, for example, for stents having a long length (e.g., about 40 mm or greater). As another example, an intermediate can be used to allow MP35N (or other material) wires to be connected to small (e.g., 100×200 um) pads. In this example, the pads can be gold (or otherwise) bump bonded to platinum wires, and the wires can then be crimped to the cables. As yet another example, an interposer can also be used to connect the cables to the pads. In this case, a replica of the pads is cut out of an insulating substance, and holes are drilled overlying the locations of the pads. These holes can be backfilled with conductive material, which can be attached (e.g., through laser welding, soldering or other methods) to the cables. Additionally or alternatively, the cables can be fed directly into the holes prior to filling. The filled holes can be ground and the interposer can then be flip-chip bonded to the stent pads. The flip-chip bonding can be conducted prior to the connection of the cables to increase the reliability of the robotically automated alignment.

Figure 62B:
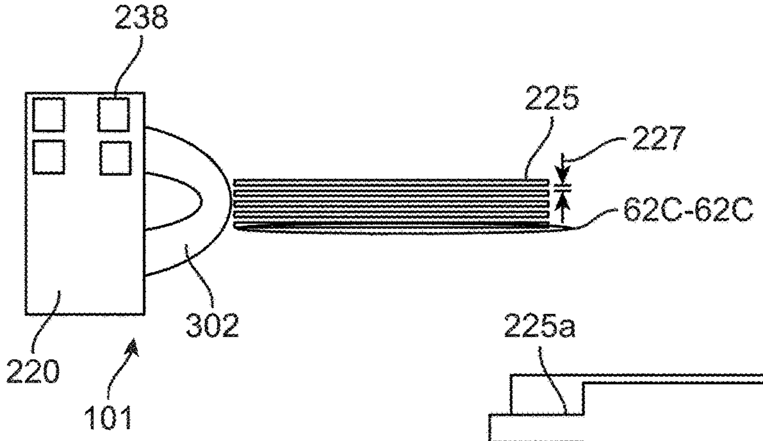
FIG. 62B illustrates a variation of a stent and cable connection.

FIG. 62B illustrates a variation of manufacturing stentrodes (e.g., stents 101) that have long, comb-like fingers 225 for each of the contacts that allow for wire wrapping or other connection method to the pads 238 (which are also elongated) on the stent 101. Each finger 225 can have one long contact, with more area to attach to. Wire wrapping can be performed around each of the fingers 225, as they will be thin enough and separated such that they are flexible and can be attached to independently. The fingers 225 coming from the back of the stent fork 302 would allow for easier manipulation and can allow for cable wire wrapping to be used to connect the stent to the cable (e.g., to connect the stent 101 to the wires 141). FIG. 62B further illustrates that the separation 227 between adjacent fingers can be about 5 μm to about 50 μm, including every 5 μm increment within this range (e.g., 10 μm).

Figure 62C:
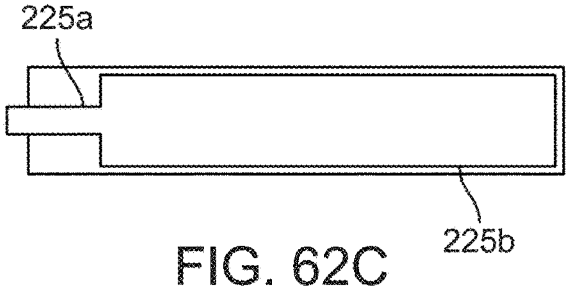
FIG. 62C illustrates a variation of a close-up of section 62C-62C of FIG. 62B.

FIG. 62C illustrates a close-up of a finger 225, showing that the finger 225 can include a track 225*a* and contact 225*b*. The track 225*a* can be about a 50 μm track and can connect the fingers 225 to the stent pads (e.g., pads 238). The contact 225*b* can be, for example, 100 μm wide and 3 mm long, or as long as the length of the stent 10.

Figure 62D:
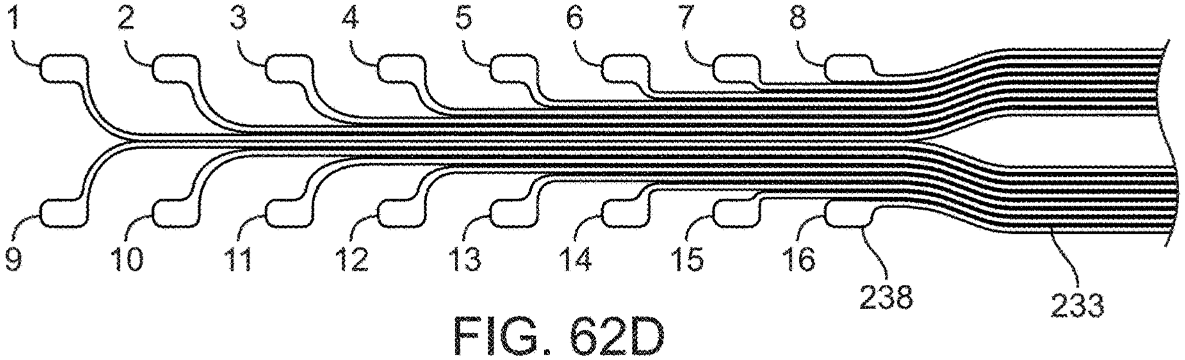
FIG. 62D illustrates a variation of a stent and cable connection.

FIG. 62D illustrates another variation to improve the connection between the stent 101 and the wires 141. As shown, the electrode pads (e.g., pads 238, pads 226) can be set into grooves 233, such that the wires 141 used to connect to the pads can be easily handled and attached. For example, the wires can be placed in the groves and then welded, with the grooves used to position and hold the wires in place prior to bonding. FIG. 62D illustrates 16 grooves and 16 corresponding pads, numbered from 1 to 16. However, any number is possible.

Figure 62E:
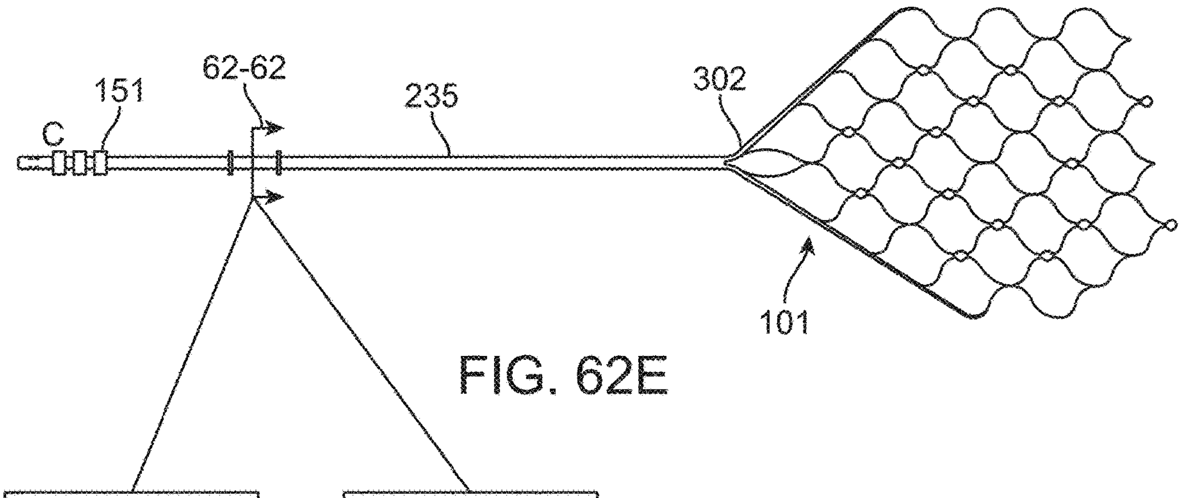
FIG. 62E illustrates a variation of a stent and cable connection.

FIG. 62E illustrates a variation where the stent 101 is printed such that connection between the stent and the cable is not required. Here, the stent itself can form the basis of the cable. In one example, the stent could be printed with the same geometry, although much longer (ie, 10 cm-30 cm or long stents are envisioned as well. In another example, the stent scaffold can finish or terminate at the apex of the fork 302, and only the electrode tracks can be printed the additional distance. Using 3D printing technology, these tracks can be printed as a helical cable around a mandrel smaller than that used for the stent (e.g., the stent 101 can be made using an 8 mm diameter mandrel, and the lead can be printed over a <1 mm diameter mandrel). In this way, the connection between the stent and the cable would not be required. As shown in FIG. 62E, the stent end 235 proximal to the stent fork 302 can be increased without altering the stent lattice 101, with the extended part 235 forming the lead (without the need to re-connect to a lead). In such variations, the lead can be thinner than the stent. The lead can be manufactured to enable connection and insertion into the stack. The stent 101 and the stent end 235 can be made in one or multiple pieces. For example, the stent 101 and the stent end 235 can made from a single wafer. The stent end 235 can be flat, curve, or both. The stent end 235 can be a helical coil. The stent 101 and the stent end 235 can be monolithically formed or separately formed. For example, the device shown in FIG. 62E can be a single long stent. The device shown in FIG. 62E has the ability to be implanted in one or multiple vessels, for example, from the same entry point. FIG. 62E further illustrates that the contacts 151 (e.g., rings) can be incorporated into this design, such that the entire manufacture of the stentrode 101 is automated. Additionally or alternatively, the tracks can be exposed at the surface in different locations, with cylinders (e.g., platinum cylinders) weld to them directly.

Figure 62F:
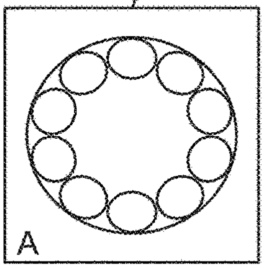
FIG. 62F illustrates a variation of the cross section 62-62 of FIG. 62E.

FIG. 62F illustrates a variation of the cross-section 62-62. As shown, the lead can be printed in 3D, with each electrode track woven around a central mandrel. This can give the lead flexibility and reliability. Multiple layers can be manufactured (e.g., 8 cables on the outer, 8 cables on the inner—same as the dual octofilar approach used for the lead described above in relation to FIGS. 41A-42).

Figure 62G:
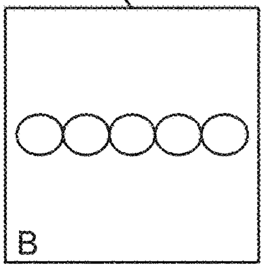
FIG. 62G illustrates a variation of the cross section 62-62 of FIG. 62E.

FIG. 62G illustrates another variation of the cross-section 62-62. As shown, the lead can be planar (2D) with wires next to each other or on top of each other, for example, pending manufacturing process.

Figure 62H:
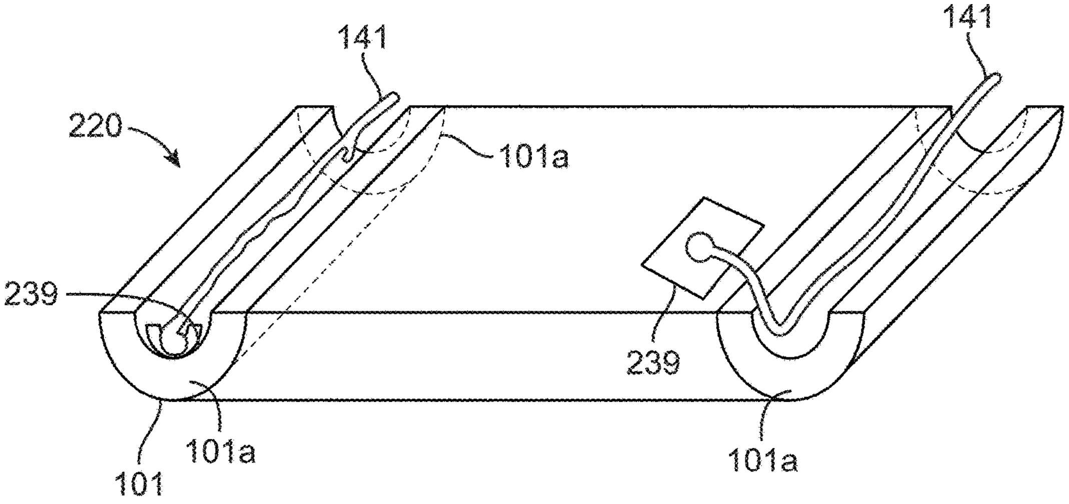
FIG. 62H illustrates a variation of a stent and cable connection.

FIG. 62H illustrates that the stent 101 can have valleys 239 in the pads (e.g., pads 238, pads 226) such that the wires 141 can be laid in the valleys 239. The stent surface 101*a* can have stent valleys 101*b*. The pad valleys 239 can be in the stent valleys 101*b*. At the end of the valleys, the wires 141 can terminate, and can be welded to the pads that are in the valleys, beside the valleys, or both. For example, FIG. 62H illustrates a variation of a stent connection panel 220, showing two valleys (cut into the surface 101*a* of the stent 101) with two wires 141 laid into the valleys which assist in aligning the wires to either a contact pad within the valley or a contact pad on the stent surface next to the valley.

More Stent Designs

FIGS. 63A-63K illustrate variations of stents 101 having the lattice and electrode arrangements shown.

Figure 63A:
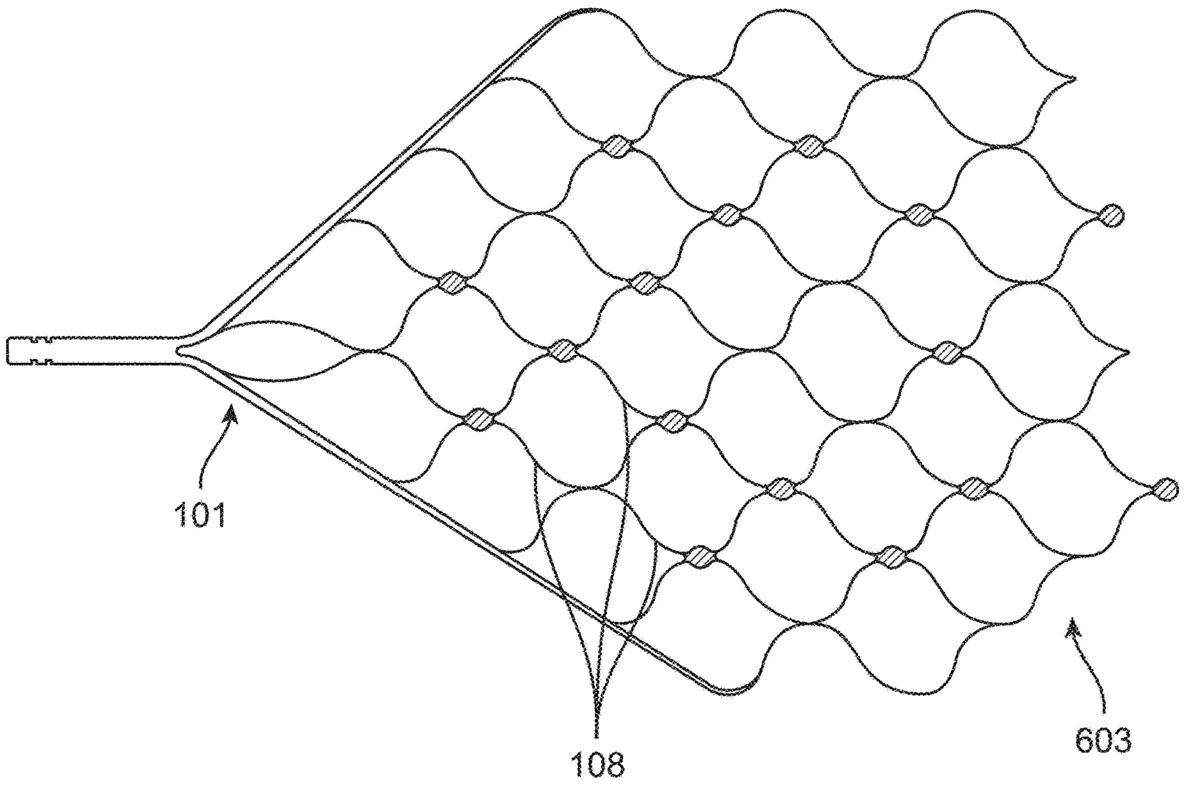
FIGS. 63A-63K illustrate variations of stents having various stent, electrode and electrode track configurations.

FIG. 63A illustrates that the struts can have a strut thickness of about 30 μm to about 90 μm, including every 5 μm within this range (e.g., 50 μm, 70 μm). Increasing the width of the struts 108 from, for example, 50 μm to 70 μm can assist with alignment of the track layers 236 that are placed on top of the struts 108. A larger width will give a larger margin of error in placement of the platinum tracks, and consequently, there will be a significant reduction in tracks that are not printed on top of the struts (e.g., are printed with some of the track outside the borders of the nitinol struts which will result in shorts or broken tracks). As described above, the cell geometry and fork angle can be chosen specifically to accommodate the deployment of electrodes 131. FIG. 63A illustrates that all cells can be identical in shape (with the exception of the cells joining the fork) such that there is a known and consistent electrode separation.

FIG. 63A further illustrates that the cell in the lower right of FIG. 47F can be removed, which is depicted by empty space 603 in FIG. 63A. This can desirably prevent the top right electrode 131 (e.g., in FIGS. 47F and 63A) from becoming entangled with this cell during deployment.

Figure 63B:
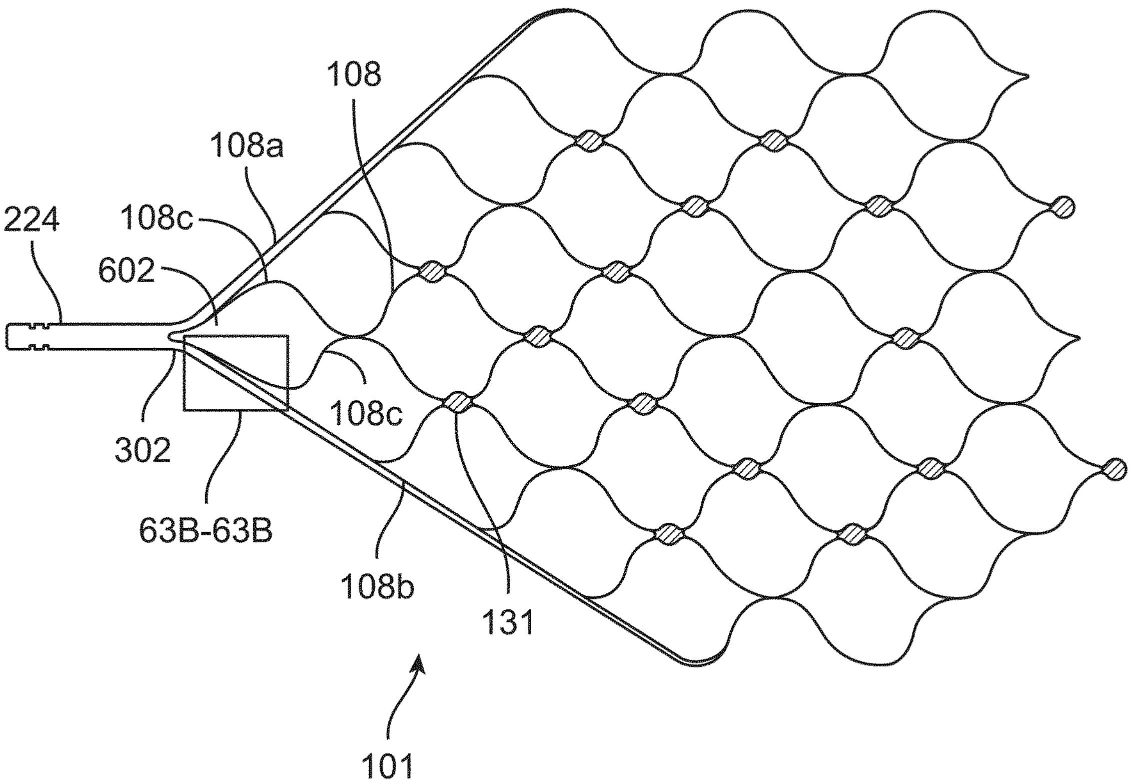

FIG. 63B illustrates that the fork 302 can be defined by a first strut 108*a*, a second strut 108*b*, one or multiple third struts 108*c*, or any combination thereof. The first and second struts 108*a*, 108*b* can decrease in thickness distally away from the fork 302. The first and second struts 108*a*, 108*b* can increase in thickness proximally toward the fork 302, for example, to accommodate more electrode tracks. The first and second struts can be outer struts and the one or multiple third struts 108*c* can be inner struts. FIG. 63B illustrates that the fork 302 can have an inner fork and an outer fork. For example, the two third struts 108_c_ can define the inner fork and the outer struts 108_a_ and 108_b_ can define the outer fork.

FIG. 63B further illustrates that the struts 108_c_ can have an increased length to increase the size (e.g., length) of the initial cell 602. This ensures that the length between the fork 302 and the first electrode 131 (or if this cell is removed as is the case in other designs, between the fork 302 and the initial cell junction) is of the same length. Having these lengths the same length helps prevent a length mismatch when the stent is retracted. This can be desirable because such mismatches can cause excessive force on the strut junctions which can cause device damage or breakage.

Figure 63C:
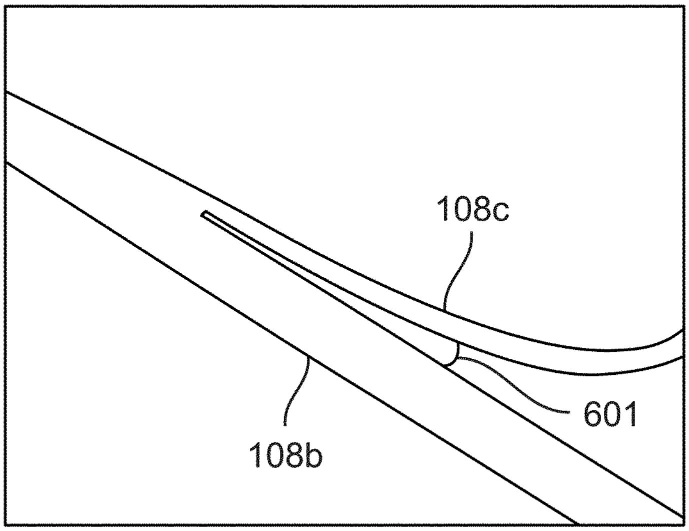

FIG. 63C illustrates that the initial inner branches 108_c_ can each have a portion parallel or nearly parallel with the adjacent first or second outer branches 108_a_ and 108_b_. For example, the branch angle 601 can be from about 1 degree to about 15 degrees, including every 1 degree increment within this range. The branches 108_c_ come off close to parallel (rather than a less parallel angle, for example, shown in FIGS. 46A-46F) which enables the stent scaffold to collapse (and when it collapses during retraction into the catheter, these struts are now aligned with the catheter not at a larger angle to the catheter).

Figure 63D:
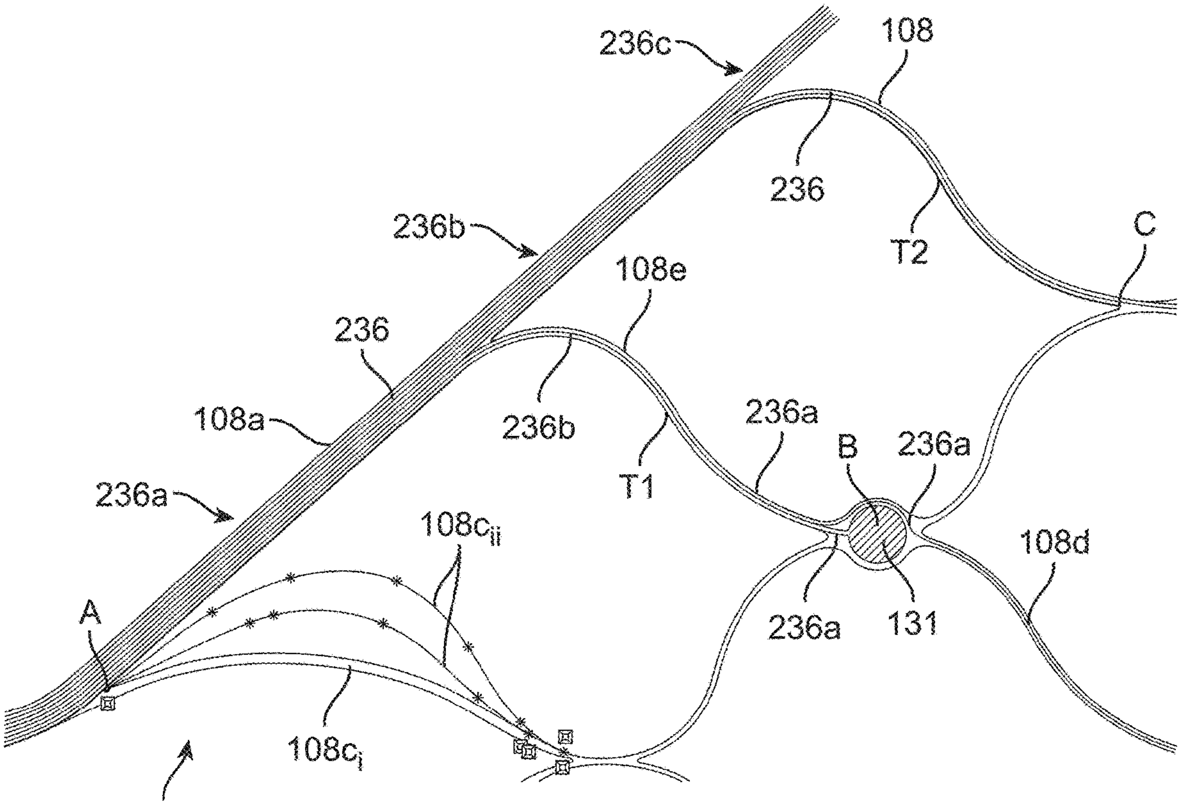
Figure 63E:
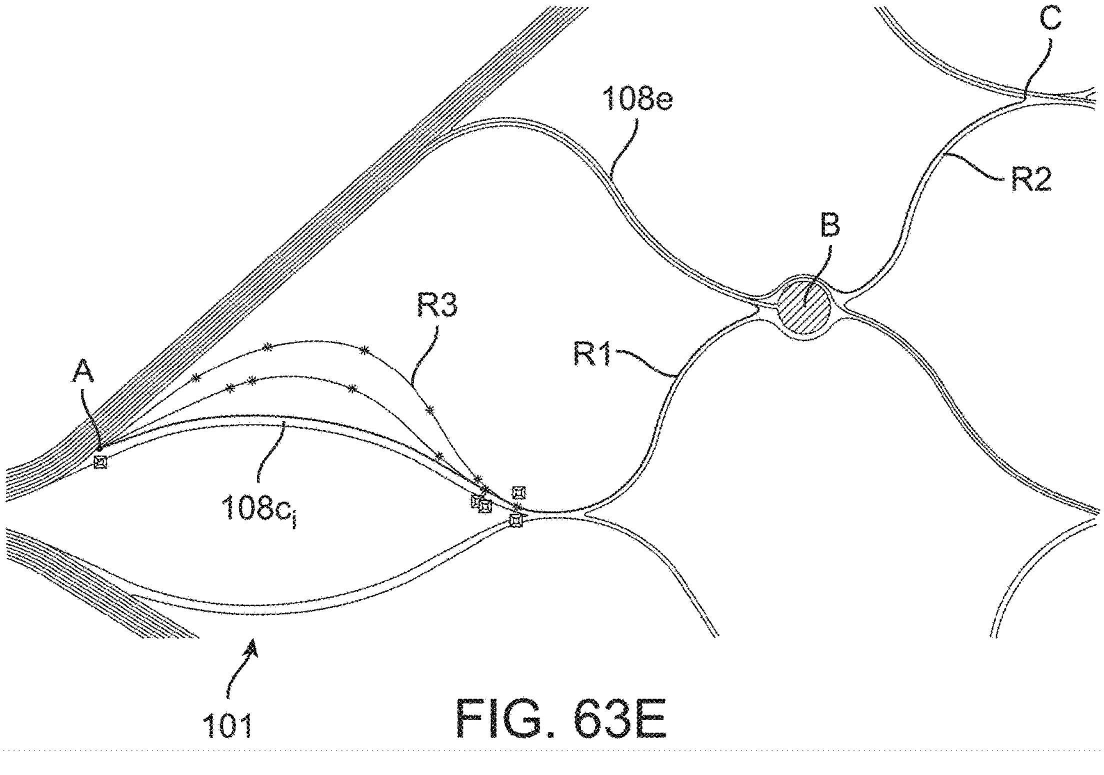

FIGS. 63D and 63E illustrate the increase in length referred to in relation to FIG. 63A, for example, in comparison to the stent 101 of FIG. 47F. For example, FIGS. 63D and 63E illustrate that increasing the length of the initial struts 108_c_, to the lengths of initial struts 108$c_{ii}$ matches the distance from point A to point B of strut T1 compared with strut R1, and matches the distance from point A to point C comparing strut T2 with strut R2. The struts T1, T2, R1, R2, R3 can have lengths of about 9.51 mm, 13.82 mm, 8.82 mm, 3.29 mm and 9.65 mm, respectively.

FIG. 63D further illustrates that first and second struts 108_a_, 108_b_ can increase in thickness proximally toward the fork 302, for example, to accommodate more electrode tracks 236. For example, the strut 108_a_ can have first, second and third strut regions having 8, 7 and 6 electrode tracks 236, respectively. FIG. 63D further illustrates that the strut 108_d_ can have the electrode track 236_a_, that the electrode track 236_a_ can meaner around the electrode 131, and that the strut 108_e_ can have the electrode tracks 236_a_ and 236_b_.

Figure 63F:
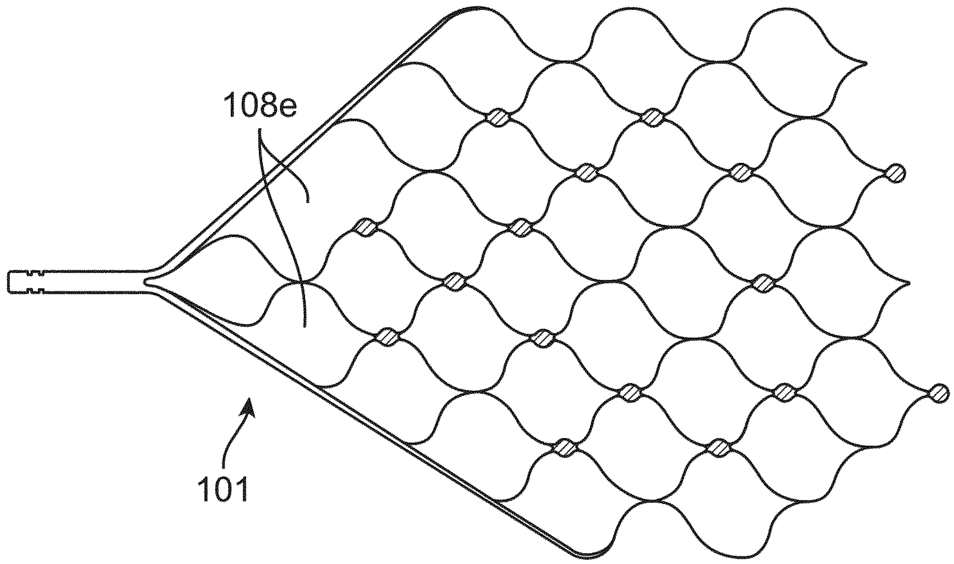

FIG. 63F illustrates that the struts 108_e_ illustrated in FIG. 63D can be removed from the stent 101 (also compare to the stent 101 illustrated in FIG. 47F). This can desirably prevent mismatch of lengths occurring. Removal of the struts 108_e_ does not detrimentally effect the deployment, retraction, or electrode and electrode track placement. In addition, the removal is does not negatively impact the radial force of the stentrode, as while the electrodes need to be placed on the wall of the vessel, they do not need additional force to open up through plaques (e.g., as balloon expanding stents do) or need to catch and pull blood clots (e.g., as retrievers do), but may use additional force (e.g., as balloon expanding stents do) and may catch and pull blood clots (e.g., as retrievers do). The conductive paths 236 in these struts have been rerouted through the fork 302.

Figure 63G:
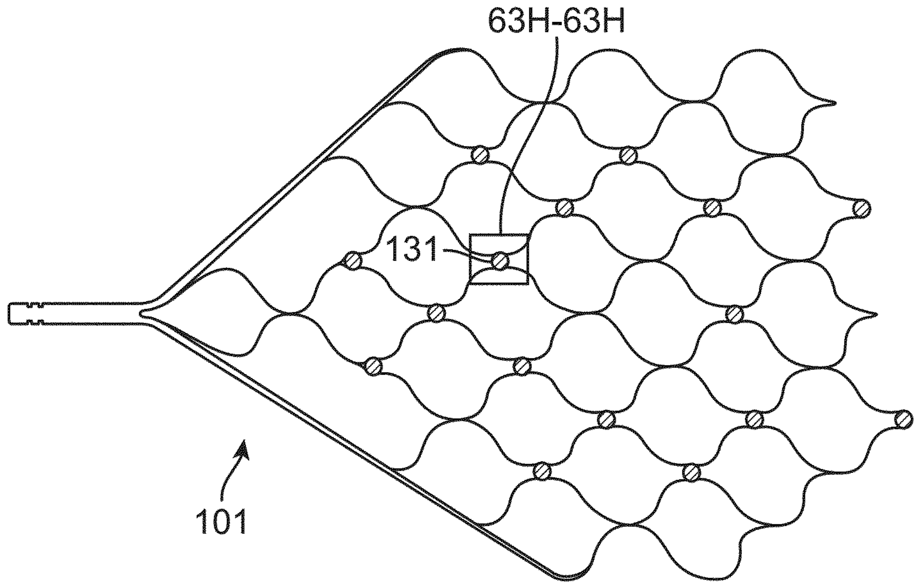

FIG. 63G illustrates that the struts 108 that attach to electrodes can be attached to or integrated with the outside of the electrodes 131 (as opposed to joining at the centre as shown in FIGS. 47F and 63A-63E). This can significantly reduce the force at the junction, as there is less bending required for the struts 108 to be horizontal (e.g., parallel to the catheter when deployed). Consequently, this can desirably reduce the delivery force of the catheter.

Figure 63H:
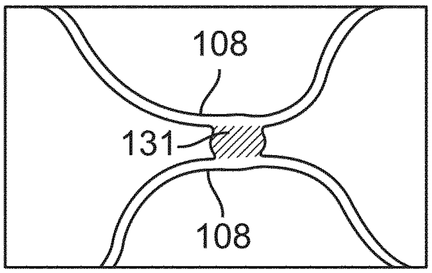

FIG. 63H illustrates a close-up view of the struts 108 attached to an outer surface of the electrodes 131.

Figure 63I:
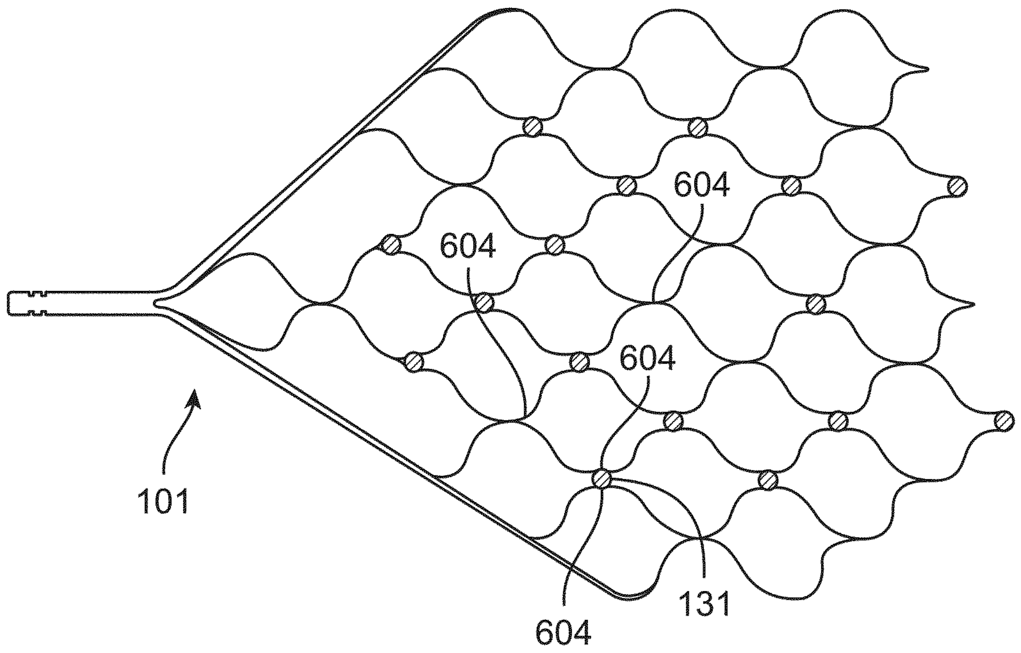

FIG. 63I illustrates that all the connections on the stent 101 (e.g., both the electrode and non-electrode connections) can have a parallel section 604. This can improve the junction between the struts 108 and between the struts and electrodes 108, 131, for example, by reducing the force on these links, and consequently reduce the force of the device during deployment and retraction. There can be a slightly larger curvature for each of the cells as the width and length (of the entire device) remains unchanged.

Figure 63J:
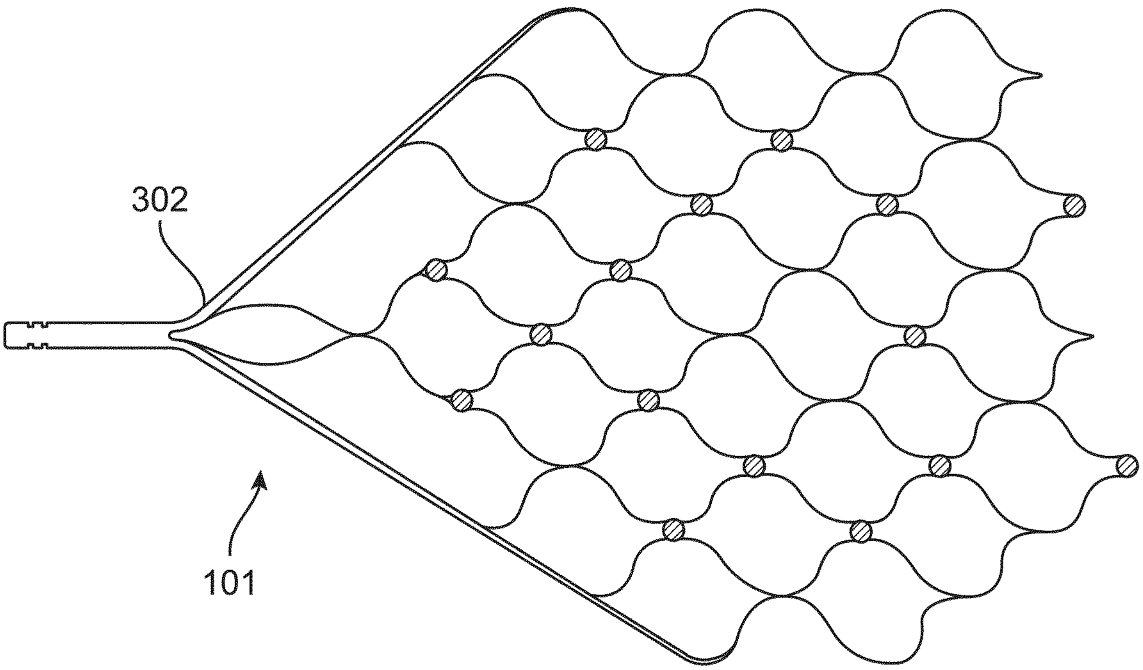

FIG. 63J illustrates that the stent of FIG. 63H can have the fork 302 of FIG. 47F.

Figure 63K:
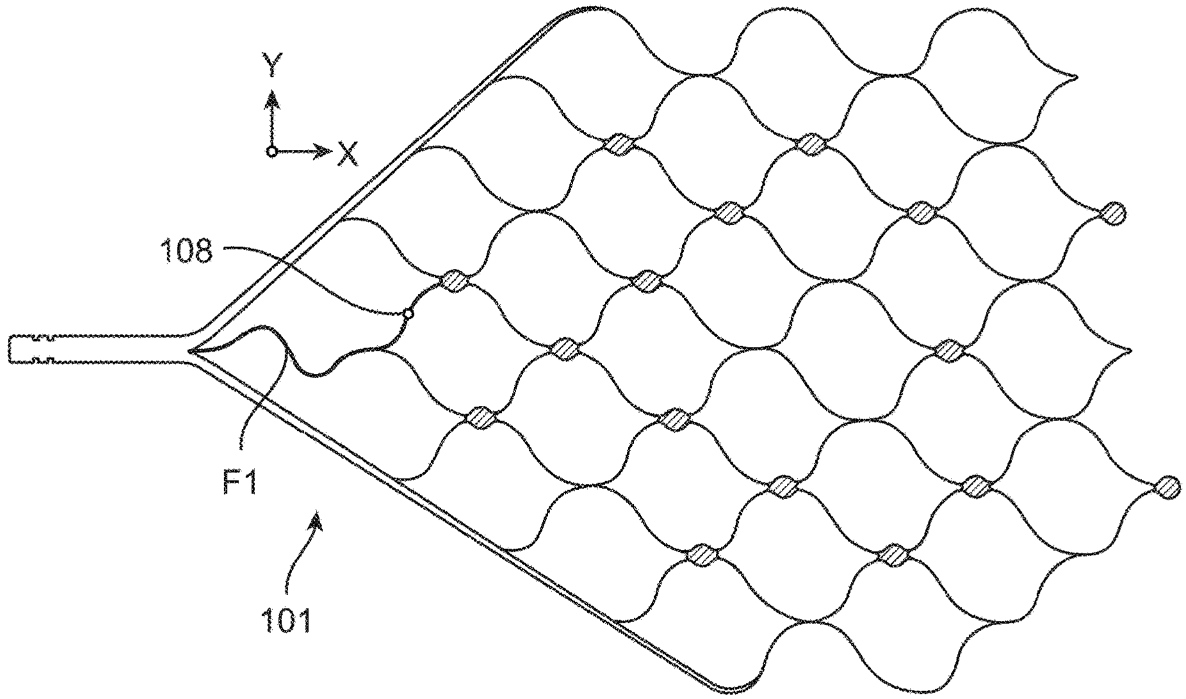

FIG. 63K illustrates that the initial struts 108_c_ of FIGS. 63A-63I can be reduced to a single strut F1. The strut F1 can have a sinusoidal curve (e.g., can have an S-shape). This 30 curve can hold electrode tracks. The length of strut F1 can be chosen to match the length of the top and base fork struts 108_a_ and 108_b_, as described previously. For example, strut F1 can have a length of about 11.01 mm.

For purposes of illustration, the stents 101 in FIGS. 63A-63K described above and are shown flat so that the cells, struts 108, electrodes 131, and/or electrode tracks 236 can be easily seen. However, the stents 101 are curved in practice (e.g., when in the compressed and/or expanded configuration) as described above with the other figures.

Any of the electrodes 131 described and illustrated can be electrodes 138, and vice versa.

Any of the wires 141 described and illustrated can be tracks 236, and vice versa.

All the dimensions in the drawings are exemplary.

The scales shown in the drawings can be indicate relative dimensions without units, or can correspond to millimeters.

The reference to any prior art in this specification is not, and should not be taken as, an acknowledgment or any form of suggestion that the prior art forms part of the common general knowledge in Australia In this specification and the claims that follow, unless stated otherwise, the word "comprise" and its variations, such as "comprises" and "comprising", imply the inclusion of a stated integer, step, or group of integers or steps, but not the exclusion of any other integer or step or group of integers or steps.

References in this specification to any prior publication, information derived from any said prior publication, or any known matter are not and should not be taken as an acknowledgement, admission or suggestion that said prior publication, or any information derived from this prior publication or known matter forms part of the common general knowledge in the field of endeavor to which the specification relates.

Any elements described herein as singular can be pluralized (i.e., anything described as "one" can be more than one). Like reference numerals in the drawings indicate identical or functionally similar features/elements. Any species element of a genus element can have the characteristics or elements of any other species element of that genus. Some elements may be absent from individual figures for reasons of illustrative clarity. The above-described configurations, elements or complete assemblies and methods and their elements for carrying out the disclosure, and variations of aspects of the disclosure can be combined and modified with each other in any combination.

We claim:

1. A method of transmitting neural activity of a patient outside a blood vessel, the method comprising:

advancing an implantable neural interface device through a vasculature, wherein the implantable neural interface device comprises an expandable frame advanceable through the vasculature in a delivery configuration, wherein the expandable frame comprises a plurality of struts defining a lattice;

deploying the expandable frame to a deployed configuration;

measuring neural activity outside the blood vessel using a plurality of electrode sites distributed along the expandable frame, wherein the plurality of electrode sites are each defined by openings through an insulating layer on the expandable frame, and wherein the openings expose portions of a conductive layer extending along the expandable frame; and communicating electrical signals between the plurality of electrode sites and a control circuitry coupled to the expandable frame via a lead assembly, wherein the lead assembly is coupled to the expandable frame and comprises a plurality of conductors and a connector region comprising a plurality of contact elements electrically coupled to each of the plurality of conductors.

2. The method of claim 1, wherein the conductive layer comprises a plurality of conductive paths extending along respective struts, wherein the plurality of conductive paths are electrically isolated from blood via the insulating layer when the implantable neural interface device is deployed.

3. The method of claim 1, wherein the plurality of contact elements are longitudinally separated by a plurality of insulators.

4. The method of claim 1, wherein the plurality of conductors comprise a plurality of wires.

5. The method of claim 4, wherein the plurality of wires form a wire bundle, wherein the wire bundle is covered by a tubular member, wherein the wire bundle couples to the plurality of contact elements at an exposed section of the wire bundle.

6. The method of claim 1, wherein deploying the expandable frame comprises positioning the expandable frame at a target site, and further comprising routing the lead assembly along a vasculature pathway from the expandable frame toward an extracranial access location when the implantable neural interface device is deployed.

7. A method of transmitting neural activity of a patient outside a blood vessel, the method comprising:

advancing an implantable neural interface device through a vasculature, wherein the implantable neural interface device comprises an expandable frame advanceable through the vasculature in a delivery configuration, wherein the expandable frame comprises a plurality of struts defining a lattice;

deploying the expandable frame to a deployed configuration;

measuring neural activity outside the blood vessel using a plurality of electrode sites distributed along the expandable frame;

communicating electrical signals between the plurality of electrode sites and a control circuitry coupled to the expandable frame via a lead assembly, wherein the lead assembly is coupled to the expandable frame and comprises a plurality of conductors and a connector region comprising a plurality of contact elements electrically coupled to each of the plurality of conductors; and electrically coupling the plurality of conductors to conductive paths of the expandable frame using a connection panel of the connector region, wherein the connection panel comprises a first set of pads and a second set of pads electrically coupled to the plurality of conductors, and wherein the first set of pads and the second set of pads are electrically coupled via at least one jumper.

8. The method of claim 7, wherein the plurality of contact elements are longitudinally separated by a plurality of insulators.

9. The method of claim 7, wherein the plurality of conductors comprise a plurality of wires.

10. The method of claim 9, wherein the plurality of wires form a wire bundle, wherein the wire bundle is covered by a tubular member, wherein the wire bundle couples to the plurality of contact elements at an exposed section of the wire bundle.

11. The method of claim 7, wherein deploying the expandable frame comprises positioning the expandable frame at a target site, and further comprising routing the lead assembly along a vasculature pathway from the expandable frame toward an extracranial access location when the implantable neural interface device is deployed.

12. A method of transmitting neural activity of a patient outside a blood vessel, the method comprising:

advancing an implantable neural interface device through a vasculature, wherein the implantable neural interface device comprises an expandable frame advanceable through the vasculature in a delivery configuration, wherein the expandable frame comprises a plurality of struts defining a lattice;

deploying the expandable frame to a deployed configuration;

measuring neural activity outside the blood vessel using a plurality of electrode sites distributed along the expandable frame; and communicating electrical signals between the plurality of electrode sites and a control circuitry coupled to the expandable frame via a lead assembly, wherein the lead assembly is coupled to the expandable frame and comprises a plurality of conductors and a connector region comprising a plurality of contact elements electrically coupled to each of the plurality of conductors, wherein the plurality of conductors comprises a first helical coil defining a lumen and a second helical coil disposed radially outward of the first helical coil.

13. The method of claim 12, wherein the first helical coil carries eight conductors and the second helical coil carries eight conductors.

14. The method of claim 12, further comprising passing a portion of the lead assembly through a wall of a blood vessel to an extravascular region.

15. The method of claim 14, further comprising positioning an implantable telemetry control unit in the extravascular region and electrically coupling the lead assembly to the implantable telemetry control unit.

16. The method of claim 15, further comprising transmitting signals representative of the measured neural activity from the implantable telemetry control unit to an external device using telemetry circuitry of the implantable telemetry control unit.

17. The method of claim 15, wherein routing the lead assembly comprises snaking the lead assembly through vasculature from the expandable frame to a location proximate the extravascular region prior to passing a portion of the lead assembly through a wall of the blood vessel.

* * * * *